US012310746B2

(12) United States Patent
Hershtik et al.

(10) Patent No.: US 12,310,746 B2
(45) Date of Patent: May 27, 2025

(54) METHODS AND SYSTEM FOR ASSOCIATING BETWEEN DISCHARGE OF CHEMICALS, AND CORRESPONDING GENETIC, MEDICAL AND/OR PATHOLOGICAL CONDITIONS

(71) Applicant: Scent Medical Technologies LTD, Tel Aviv (IL)

(72) Inventors: Harel Hershtik, Rehovot (IL); Drew Morris, North Potomac, MD (US); Ehud Cantor, Kfar Saba (IL)

(73) Assignee: SCENT MEDICAL TECHNOLOGIES LTD, Tel Aviv (IL)

( * ) Notice: Subject to any disclaimer, the term of this patent is extended or adjusted under 35 U.S.C. 154(b) by 1006 days.

(21) Appl. No.: 17/291,269

(22) PCT Filed: Nov. 4, 2019

(86) PCT No.: PCT/IL2019/051208
§ 371 (c)(1),
(2) Date: May 4, 2021

(87) PCT Pub. No.: WO2020/089923
PCT Pub. Date: May 7, 2020

(65) Prior Publication Data
US 2022/0003746 A1    Jan. 6, 2022

Related U.S. Application Data

(60) Provisional application No. 62/929,882, filed on Nov. 3, 2019, provisional application No. 62/772,645, filed on Nov. 29, 2018.

(30) Foreign Application Priority Data

Nov. 4, 2018  (IL) .......................... 262771

(51) Int. Cl.
*A61B 5/00* (2006.01)
*G01N 33/497* (2006.01)

(52) U.S. Cl.
CPC ........ *A61B 5/4848* (2013.01); *G01N 33/4975* (2024.05); *G01N 33/4977* (2024.05); *G01N 2800/52* (2013.01)

(58) Field of Classification Search
None
See application file for complete search history.

(56) References Cited

U.S. PATENT DOCUMENTS 9,315,848 B2    4/2016 Haick et al.
2011/0059476 A1    3/2011 Shin et al.
(Continued)

FOREIGN PATENT DOCUMENTS

CN    107787492 A    3/2018
EP    3 143 930    3/2017
(Continued)

OTHER PUBLICATIONS

Search Report dated May 8, 2024, issued in United Arab Emirates Application No. P6000728/2021.
(Continued)

*Primary Examiner* — Xiaoyun R Xu
(74) *Attorney, Agent, or Firm* — Knobbe, Martens, Olson & Bear, LLP

(57) ABSTRACT

A method is for determining the effect of a selected treatment administered to a patient. The method includes acquiring VOC-emission-data of pre-treatment-target-cells-cultures and producing a pre-treatment-target cells-VOC-profile from the VOC-emission of the pre-treatment-target-cells-cultures. An MCD-target-cells-VOC-profile can be produced by inducing MCD on non-treated target-cells-cultures thereby producing post-MCD-target-cells-cultures and acquiring VOC-emission-data of the post-MCD-target-cells-cultures. The selected treatment is applied to target-cells-cultures and VOC-emission-data of post-treatment-target-cells-cultures is acquired. The treatment is determined as effective when concentration values from VOC-emission- (Continued)

data of pre-treatment-target-cells-cultures, of VOCs associated with the pre-treatment-target-cells-VOC-profile, are greater than concentration values from the VOC-emission-data of post-treatment-target-cells-cultures, of VOCs associated with the pre-treatment-target-cells-VOC profile and (b) concentration values from VOC-emission-data of post-treatment-target-cells-cultures, of VOCs associated with the MCD-target-cells-VOC-profile, emitted by the post-treatment-target-cell-cultures, are greater than concentration values from the VOC-emission-data of pre-treatment-target-cells-cultures, of VOCs associated with the MCD-target-cells-VOC-profile, emitted by the pre-treatment-target-cell cultures.

10 Claims, 40 Drawing Sheets

(56) References Cited

U.S. PATENT DOCUMENTS

| | | |
|---|---|---|
| 2015/0301021 A1 | 10/2015 | Haick et al. |
| 2016/0282352 A1 | 9/2016 | Martino et al. |
| 2017/0045495 A1 | 2/2017 | Trowell et al. |
| 2017/0227429 A1 | 8/2017 | Koo et al. |

FOREIGN PATENT DOCUMENTS

| | | |
|---|---|---|
| WO | WO 03/034992 A2 | 5/2003 |
| WO | WO2012023138 | 2/2012 |
| WO | WO 2014/132077 A1 | 9/2014 |
| WO | WO 2014180974 | 11/2014 |

OTHER PUBLICATIONS

Nardi-Agmon et al., "Exhaled Breath Analysis for Monitoring Response to Treatment in Advance Lung Cancer", Journal of Thoracic Oncology, 2016, 11(6): 827-837.

Office Action issued in Chinese Application No. 201980087788.5, dated Jan. 25, 2024.

Pyo et al., "Determination of volatile biomarkers for apoptosis and necrosis by solid-phase microextraction-gas chromatography/mass spectrometry: A pharmacometabolomic approach to cisplatin's cytotoxicity to human lung cancer cell lines", Journal of Chromatography B, 2008, 876: 170-174.

Esther M. Arkin, et al "An Efficiently Computable Metric for Comparing Polygonal Shapes", IEEE Transactions on Pattern Analysis and Machine Intelligence, vol. 13, No. 3, Mar. 1991.

D. F. Altomare et al, "Exhaled volatile organic compounds identify patients with colorectal cancer", British Journal of Surgery 2013; 100: 144-150 Published by John Wiley & Sons Ltd.

Summary of Safety and Probable Benefit, Menssana Research, Inc. Hearts breath Test for Grade 3 Heart Transplant Rejection, Humanitarian Device Exemption (HOE) No. H030004 Date of Humanitarian Use Device Designation: Oct. 23, 2002.

B de Lacy Costello1 et al, "A review of the volatiles from the healthy human body", J. Breath Res. 8 (2014) 014001 (29pp).

Agnieszka Ulanowska1 et al., "The application of statistical methods using VOCs to identify patients with lung cancer", J. Breath Res. 5 (2011) 046008 (11pp).

Agnes W Boots at el. "The versatile use of exhaled volatile organic compounds in human health and disease", doi:10.1088/1752-7155/6/2/027108, Published May 23, 2012 (22pp).

Bogdan Calenic et al. "Oxidative stress and volatile organic compounds: interplay in pulmonary, cardio-vascular, digestive tract systems and cancer" Open Chem., 2015; 13: 1-11 Bogdan Calenic et al., licensee De Gruyter Open. (12pp).

Frank S. Cikach Jr. and Raed A. Dweik "Cardiovascular Biomarkers In Exhaled Breath", Prog Cardiovasc Dis. 2012 ; 55(1): 34-43. doi:10.1016/j.pcad.2012.05.005. (20pp.).

Wojciech Filipiak, Andreas Sponring, Tomas Mikoviny, Clemens Ager, Jochen Schubert, Wolfram Miekisch, Anton Amann and Jakob Troppmair "Release of volatile organic compounds (VOCs) from the lung cancer cell line CALU-1 in vitro", Published: Nov. 24, 2008 Cancer Cell International 2008, 8:17 doi:10.1186/1475-2867-8-17 http://www.cancerci.com/content/8/1/17 (11pp).

Extended European Search Report issued in EP Application No. 19878017.3, dated Sep. 30, 2022.

FROM PROCEDURE 274
FIGURE 5B

FROM PROCEDURE 276
FIGURE 5B

DETERMINING PREDICTED TARGET VOC PROFILE IS DETERMINED BY PREDICTING THE CONCENTRATION LEVELS IN THE BREATH AND BODY FLUIDS FROM THE PRE-MCD TARGET VOC PROFILE AND THE POST-MCD TARGET VOC PROFILE AND DETERMINING A PREDICTED HEALTHY VOC PROFILE IS DETERMINED BY PREDICTING THE CONCENTRATION LEVELS IN THE BREATH AND BODY FLUIDS FROM THE PRE-MCD AND THE POST-MCD HEALTHY VOC PROFILE.

— 278

FROM PROCEDURE 258
FIGURE 5A

PRODUCING ABNORMAL RESPONSE VOC PROFILE AND NORMAL RESPONSE VOC PROFILE, RELATED TO THE RESPONSE OF THE PATIENTS TO THE TARGET CELLS, RELATED TO THE RESPONSE OF THE PATIENTS TO THE TARGET CELLS BY COMPARING THE BREATH AND/OR BODY FLUIDS VOC EMISSION DATA FROM A PLURALITY OF PATIENTS WITH ABNORMAL LEVELS OF TARGET CELLS, WITH THE BREATH AND/OR BODY FLUIDS VOC EMISSION DATA FROM A PLURALITY OF PATIENTS WITH NORMAL LEVELS OF TARGET CELLS, THE PREDICTED TARGET VOC PROFILE AND THE PREDICTED HEALTHY VOC PROFILE

— 280

FROM PROCEDURE 258
FIGURE 5A

PRODUCING A DYNAMIC DIFFERENTIAL VOC PROFILE FROM THE PREDICTED TARGET VOC PROFILE, THE PREDICTED HEALTHY VOC PROFILE, ABNORMAL RESPONSE VOC PROFILE, ABNORMAL RESPONSE VOC PROFILE, THE BREATH AND/OR BODY FLUIDS VOC EMISSION DATA FROM A PLURALITY OF PATIENTS WITH ABNORMAL LEVELS OF TARGET CELLS AND THE BREATH AND/OR BODY FLUIDS VOC EMISSION DATA FROM A PLURALITY OF PATIENTS WITH NORMAL LEVELS OF TARGET CELLS.

— 282

STORING THE VOC PROFILES IN A DATABASE

FROM PROCEDURE 314
FIGURE 6A → APPLYING GENE ACTIVATION TREATMENT TO THE CELLS IN THE HEALTHY CELL CULTURE ~320 → ACQUIRING POST-TREATMENT HEALTHY CELLS CULTURES VOC EMISSION DATA RELATING TO THE HEALTHY CELLS CULTURES SETS AFTER THE SELECTED MMR GENE ACTIVATION TREATMENT ~326

FROM PROCEDURE 310
FIGURE 6A → PRODUCING AN MMR GENE ACTIVATION HEALTHY CELLS VOC PROFILE BY COMPARING THE PRE-TREATMENT HEALTHY CELLS CULTURES VOC EMISSION DATA, WITH THE POST-TREATMENT VOC EMISSION DATA ~332 → DETERMINING A PREDICTED TREATMENT INDUCED HEALTHY VOC PROFILE ~338 → TO PROCEDURE 340 FIGURE 6D

FIG. 6C

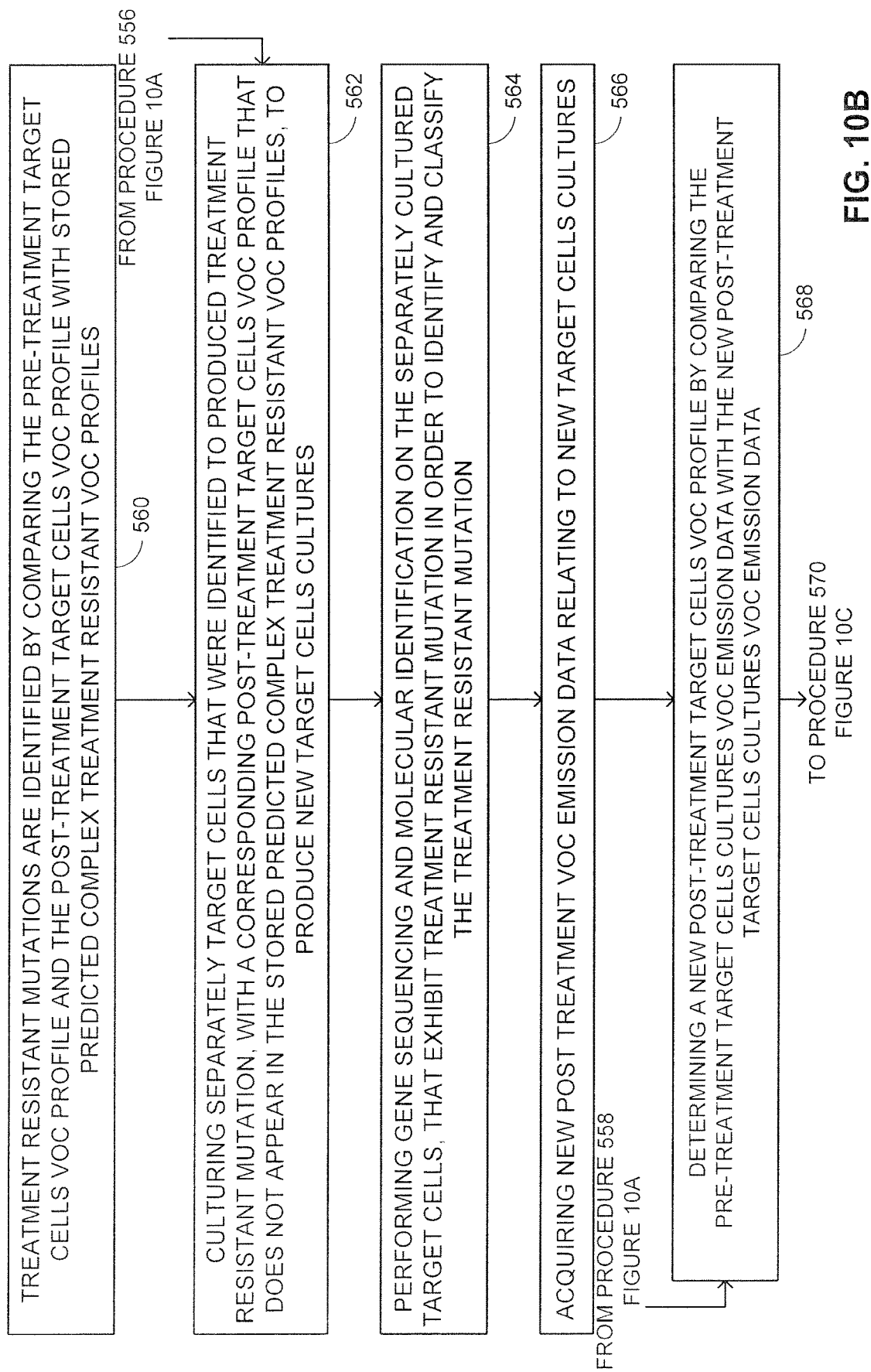

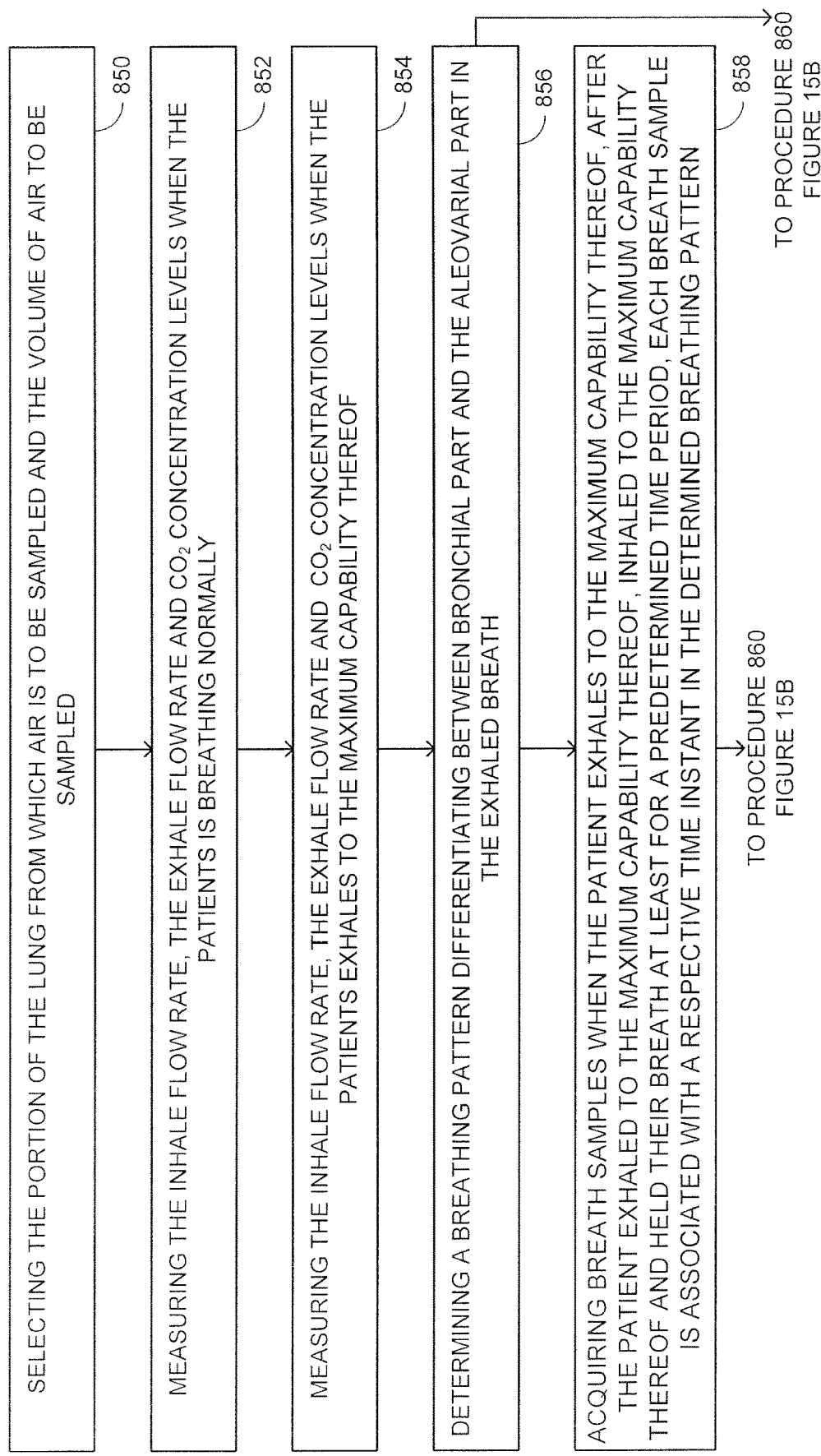

METHODS AND SYSTEM FOR ASSOCIATING BETWEEN DISCHARGE OF CHEMICALS, AND CORRESPONDING GENETIC, MEDICAL AND/OR PATHOLOGICAL CONDITIONS

FIELD OF THE DISCLOSED TECHNIQUE

The disclosed technique relates to identifying discharge of chemicals in a person's body and/or cultures, in general, and to methods and system for associating between discharge of chemicals in a person's body and/or cultures, and corresponding genetic, medical and/or pathological conditions in particular.

BACKGROUND OF THE DISCLOSED TECHNIQUE

Metabolic, anabolic and/or catabolic processes produce chemical compounds. Some of the compounds belong to three groups of compounds, namely, Volatile Organic Compounds (VOCs), Semi Volatile Organic Compounds (SVOCs) and Volatile Sulfur-Containing Compounds (VSCs). The compounds in these groups typically maintain a gaseous state at room temperature. Monitoring gases related to metabolic, anabolic and/or catabolic processes is known in the art. For example, monitoring Oxygen ($O_2$) saturation levels is employed for monitoring a patient's condition. Similarly Carbon Dioxide ($CO_2$) is employed as an indicator for a broad range of lung related diseases.

The publication "Summary of Safety and Probable Benefit, Menssana Research, Inc. Hearts Breath Test for Grade 3 Heart Transplant Rejection" directs to monitoring the VOCs in the breath of heart transplant recipients, in order to aid in the diagnosis of grade 3 heart transplant rejection.

The publication "A Review of the Volatiles From the Healthy Human Body" to de Lacy Costello et al, directs to compendium of VOCs reported from the healthy human body. In the compendium, a total of 1840 VOCs are identified in breath, saliva, urine, milk, blood, skin secretions, and feces. 872 were found in breath, 359 were found in saliva, 154 were found in blood, 256 were found in milk, 532 were found in skin secretions, 279 were found in urine and 381 were found in feces. The publication "The Application of Statistical Methods Using VOCs to Identify Patients with Lung Cancer", to Ulanowska et al, directs to an attempt to determine a group of lung cancer biomarkers. To that end, breath samples were acquired from 137 patients with confirmed lung cancer. These samples were analyzed employing the SPME-GC/MS method. Exhaled air was also acquired from 143 healthy volunteers with different smoking habits (active smokers, passive smokers and nonsmokers) as a reference group. Statistical methods such as discriminant analysis (DA) and the CHAID model tree were used for data processing and evaluation. Ulanowska suggested that chemotherapy treatment for lung cancer might be controlled by employing molecular biomarkers, such as amino acid, peptide, lipid and carbohydrate, and it is defined as a molecule which reflects the pathological state of the organ and can be a characteristic pharmacological response to a therapeutic intervention.

Altomare in 2012 described that breath analysis, using a triple quadrupole Gas Chromatograph Mass Spectrometer (hereinafter "GC-MS/MS") may, detect VOCs which are characteristic of particular conditions, such as colorectal cancer and melanoma.

P.C.T. Patent Application Publication WO 2014/180974 to Domingues Ortega, entitled "VOC-Based, Narcolepsy Diagnostic Method", directs to detecting narcolepsy in a patient by obtaining a sample from a subject and detecting the levels of at least one VOC in the sample in order to obtain a VOC profile of the sample. Thereafter, the VOC profile of the sample is compared with a reference VOC profile to determine if the patient has narcolepsy.

SUMMARY OF THE PRESENT DISCLOSED TECHNIQUE

It is an object of the disclosed technique to provide a novel method and system for associating between discharge of chemicals in at least one of a person's breath, body fluids, cell cultures, and corresponding representations of genetic or medical conditions, and employing these associations for diagnosis, and/or determining treatment efficacy and/or determining treatment selection.

In accordance with an embodiment of the disclosed technique, there is thus provided a method for determining the effect of at least one selected treatment of a metabolic, anabolic, catabolic, genetic and/or medical condition administered to a patient. The method includes the procedures of acquiring VOC emission data of pre-treatment target cells cultures and producing a pre-treatment target cells VOC profile from the VOC emission of the pre-treatment target cells cultures. The method further includes the procedure of producing an MCD target cells VOC profile by:

(a) inducing massive cell death on non-treated target cells cultures thereby producing post-MCD target cells cultures; and (b) acquiring VOC emission data of the post-MCD target cells cultures.

The method also includes the procedures of applying the at least one selected treatment at least to target cells cultures, acquiring VOC emission data of post-treatment target cells cultures for each selected treatment and determining the effect of the selected treatment. The treatment is determine as effective when:

(a) concentration values from the VOC emission data of pre-treatment target cells cultures, of VOCs associated with the pre-treatment target cells VOC profile, are greater than concentration values from the VOC emission data of post-treatment target cells cultures, of VOCs associated with the pre-treatment target cells VOC profile; and (b) concentration values from the VOC emission data of post-treatment target cells cultures, of VOCs associated with the MCD VOC profile, emitted by the post-treatment target cell cultures, are greater than concentration values from the VOC emission data of pre-treatment target cells cultures, of VOCs associated with the MCD VOC profile, emitted by the pre-treatment target cell cultures.

In accordance with another aspect of the disclosed technique, there is thus provided a method for determining the efficacy of a treatment of a metabolic, anabolic, catabolic, genetic and/or medical condition administered to a patient. The method includes the procedures of acquiring pre-treatment patient VOC emission data of the VOCs emitted from at least one of breath samples and body fluid samples prior to at least one selected phase of the treatment and acquiring VOC emission data of pre-treatment target cells cultures. The method further includes the procedure producing a predicted MCD target cells VOC profile by:

(a) inducing massive cell death on non-treated target cells cultures thereby producing post-MCD target cells cultures;
(b) acquiring VOC emission data of the post-MCD target cells cultures; and
(c) predicting the concentration levels of the VOCs in the breath and/or body fluids employing a diffusion model;

The method also includes the procedures of applying the selected treatment to the patient, acquiring post-treatment patient VOC emission data of the VOCs emitted from at least one of breath samples and body fluid samples that were acquired during and/or after at least one selected phase of the treatment, and determining an the efficacy of the selected treatment. The treatment is determined as effective when concentration values of the VOCs in the predicted MCD target cells VOC profile during and/or after the selected phase of the treatment from the post-treatment patient VOC emission data associated with at least one of breath samples and body fluid samples is greater than concentration values of the VOCs in the predicted MCD target cells VOC profile before the selected phase of the treatment from the pre-treatment patient VOC emission data associated with at least one of breath samples and body fluid samples.

In accordance with a further aspect of the disclosed technique, there is thus provided a method for determining the efficacy of a treatment administered to a patient. The method includes the procedures of acquiring at least one of breath and body fluid samples prior to at least one phase of the treatment, acquiring VOC emission data of the VOCs emitted by the at least one of breath samples and body fluid samples acquired prior to the at least one phase of the treatment and identifying a stored Dynamic Differential VOC profile which corresponds to the acquired VOC emission data, thereby associating a pathological condition with the VOC emissions data. The method further includes the procedure of acquiring at least one of breath and body fluid samples during and/or after the at least one phase of the treatment, acquiring VOC emission data of the VOCs emitted in the at least one of breath samples and body fluid samples acquired during and/or after the at least one phase of the treatment and classifying the efficacy of the treatment at least by comparing the concentration values of the VOCs in the identified Dynamic Differential VOC profile acquired before the at least one phase of the treatment with concentration values of the VOCs in the identified Dynamic Differential VOC profile acquired during and/or after the at least one phase of the treatment. The at least one phase of the treatment is classified as successful when the concentration levels of the VOCs related to the target cells VOC profile in the Dynamic Differential VOC profile during and/or after the selected phase of the treatment are reduced relative to the concentration values of the VOCs in the identified dynamic differential VOC profile before the treatment.

BRIEF DESCRIPTION OF THE DRAWINGS

The disclosed technique will be understood and appreciated more fully from the following detailed description taken in conjunction with the drawings in which:

FIGS. 5A, 5B and 5C are a schematic illustration of a method for associating VOC profiles with pathological conditions, which results from pathogens, operative in accordance with a further embodiment of the disclosed technique;

FIGS. 6A-6D are a schematic illustration of a method for determining a Dynamic Differential VOC profile for a selected MisMatch Repair (MMR) gene activation therapy, in accordance with another embodiment of the disclosed technique;

FIGS. 10A, 10B and 10C are a schematic illustration of a method for identifying a personal treatment resistant VOC profile of an individual for a selected treatment, operative in accordance with another embodiment of the disclosed technique;

FIGS. 17A and 17B are a schematic illustration of a method for increasing the VOCs concentration prior to sampling and sampling a quantified amount of air from a selected portion of the lungs, operative in accordance with another embodiment of the disclosed technique.

DETAILED DESCRIPTION OF THE EMBODIMENTS

Figure 1:
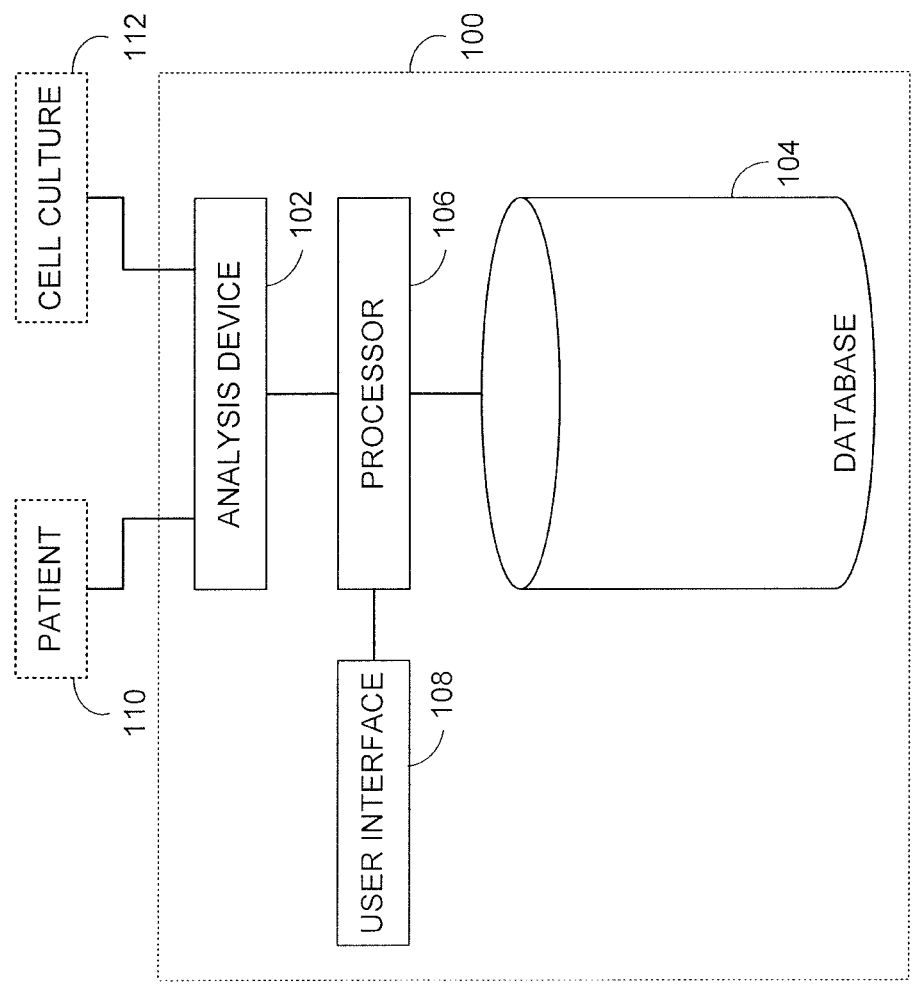
FIG. 1 is a schematic illustration of a system for associating between discharge of chemicals in at least one of a person's breath, body fluids, cell cultures, and corresponding representations of genetic or medical conditions, and employing these associations for diagnosis, and/or determining treatment efficacy and/or determining treatment selection, constructed and operative in accordance with an embodiment of the disclosed technique.

The disclosed technique overcomes the disadvantages of the prior art by providing methods and system for associating between discharge of chemicals such as VOCs, SVOCs and/or VSCs in at least one of a person's breath, body fluids, or cell cultures, and corresponding representations of genetic, medical or pathological conditions. This association may then be employed for diagnosis, determining treatment efficacy or for selecting a treatment, either for an individual patient or generally for a selected population. The genetic and/or medical and/or pathological conditions may include carcinogenic processes at various stages thereof, as well as conditions caused by pathogens (e.g., bacteria, viruses, fungi and the like).

In general, associating the VOC emission data with corresponding genetic, medical and/or pathological conditions includes acquiring the VOC emission data (e.g., with a mass-spectrometer), either in-vivo (e.g., exhaled breath), in-vitro (e.g., cultured cells) or both, of both healthy and un-healthy patients and determining a VOC profile associated with the genetic, medical and/or pathological conditions. The VOC profile may then be stored in a database and employed at a later time for various purposes discussed further herein below. The terms 'VOC', 'VOC emission data' and 'VOC profile' shall also be further elaborated below.

Further herein, the term 'target cells' relates herein to any cells of interest which may exhibit a genetic, medical and/or pathological condition, which cause a genetic, medical and/or pathological condition (e.g., Cancer cells, Alzheimer infected cells, germs or viruses), or are related to a genetic, medical and/or pathological condition (e.g., Papilloma virus may cause cervical cancer, hence it is of interest in relation to cervical cancer), originating from either within the body or outside the body. Target cells may also be mutations of other target cells. For example, carcinogenic cells are target cells. Also, bacteria, viruses and fungi may also be target cells. Infected tissue cells may also be target cells.

The term 'cell type' relates herein to the type or arc type from which the target cell originated. For example, breast cancer cells originate from cells only found in the breast. Another example is the drug resistant bacteria string Klebsiella Pneumonia Carbapenemase (KPC), that originate from the drug susceptible origin bacteria (arc type)—Klebsiella Pneumonia (KP).

The term 'culture' relates to at least one culture. The term 'culture' may also relate to a plurality cultures and may further refer to multiple cell cultures grown using different broth mediums and broth conditions. For example, KPC can be cultured in Mueller Hinton Broth (MB) or Tryptic Soy Broth (TSB).

The term 'VOC' relates to any chemical compound or compounds found in vivo and/or in vitro samples (e.g., breath samples, urine samples, blood samples and/or culture samples). For example, the term 'VOC' may relate to Volatile Organic Compound such as hydrocarbon, esters, aldehydes and ketones, and may further refer to Volatile Sulfur-Containing Compound such as dimethylsulfide. The term 'VOC' may further relate to complex molecules metabolites and/or biological elements. For example, proteins, antibodies, enzymes, RNA and DNA.

The term 'VOC emission data' relates at least to the presence or absence of a selected VOC or selected VOCs. The VOC emission data may further refer to the concentration levels of all or selected VOCs in a sample. VOC emission data may further relate to the mass spectra, ion mobility, and/or retention time (i.e., elution time from a GC column) of a selected VOC or multiple selected VOCs in the sample. VOC emission data may also relate to a full mass spectra (molecular ion and fragments), ion mobility, and/or retention time separately or combined of all the VOCs in the sample. For example, an analytical device such as a Gas Chromatograph Field Asymmetric Ion Mobility Spectrometer Mass Spectrometer (GC-FAIMS-MS) provides GC retention time separation information, mass spectra, and ion mobility information for each VOC detected. The VOC emission data may be provided in units of parts per million (ppm), parts per billion (ppb), parts per trillion (ppt) and the like. VOC emission data may further be provided in the count rate, for example, parts per second, ppm per second and the like. VOC emission data may be represented, for example, in vector or matrix form.

The term 'VOC profile' relates to VOC emission data associated with a corresponding metabolic, anabolic, catabolic, genetic and/or medical condition (e.g., healthy person, non-healthy person, carcinogenic processes, metabolic processes, a cancer type, bacteria, virus or fungus). VOCs profiles may relate to VOCs concentration levels and may alternatively or additionally relate to the ratio between selected VOCs concentration levels, or patterns generated by some or all the VOCs appearing in the VOC emission data, as further explained below. A VOC profile may serve as a template of the VOCs emission associated with a corresponding metabolic, anabolic, catabolic, genetic and/or medical condition. Herein the term 'healthy VOC profile' relates to the weighted average of the VOC emission data relating to healthy patients (i.e., from at least one of the following: breath, bodily fluids or cell cultures). Similarly, the term 'target cells VOC profile' relates to the weighted average of the VOC emission data relating to target (i.e., from at least one of the following: breath, bodily fluids or cell cultures). The term 'dynamic differential VOC profile' relates to the range of VOC emission data of each profile (i.e., healthy profile, target profile), and/or the range between healthy and target VOC profiles. Herein, the terms VOC emission data, healthy VOC profile, target VOC profile and differential VOC profile may follow an adjective describing the pertinent term, for example, 'pre-MCD target cells VOC profile'.

Reference is now made to FIG. 1, which is a schematic illustration of a system, generally referenced 100, for associating between discharge of chemicals in at least one of a person's breath, body fluids, cell cultures, and corresponding representations of genetic or medical conditions, and employing these associations for diagnosis, and/or determining treatment efficacy and/or determining treatment selection, constructed and operative in accordance with an embodiment of the disclosed technique. The system includes an analysis device 102, a database 104 and a processor 106. The system may further include a user interface 108. Processor 106 is coupled to analysis device 102, to database 104 and to user interface 108.

Analysis device 102 may be a mass-spectrometer (MS), an ion mobility spectrometer (IMS), a gas chromatograph (GC), various combinations MS, GC, IMS, or any other device which provides identification and/or quantification of VOC analytes within a sample. Analysis device 102 is, for example, a triple quadrupole gas chromatograph mass-spectrometer (GC-MS/MS), which may include a thermal dissolver and which operates in a selected ion monitoring MS mode. Alternatively, analysis device 102 may be a calibrated Proton Transfer Reaction Time of Flight Mass-Spectrometer (PTR-TOFMS) or a calibrated Selected Ion Flow Tube Mass-Spectrometer (SIFT-MS), field asymmetric ion mobility spectrometer (FAIMS), gas chromatograph photon ionization detector, or field asymmetric ion mobility spectrometer Time of Flight Mass-Spectrometer (FAIMS-TOFMS), or Gas Chromatograph Quadrupole Time of Flight (GC-QTOF), or Gas Chromatograph Orbitrap (e.g., GC-exactive), or Gas Chromatograph Quadrupole Mass Spectrometer Orbitrap (GC-Q exactive) analysis device. Analysis device 102 is employed to acquire a measurement of various chemicals, and specifically VOCs, within the breath or body fluids of a patient 110. Analysis device 102 is further employed to acquire a measurement of various chemicals, in cell cultures 112. Analysis device 102 provides processor 106 with raw measurements.

Processor 106 associates between discharge of chemicals, and corresponding metabolic processes, anabolic processes, catabolic processes, genetic conditions and/or medical conditions and/or pathological conditions as further elaborated below. Processor 106 further employs these associations for diagnosis, for determining treatment efficacy and for selecting suitable treatment, also as elaborated below in the description which follows.

Figure 2A:
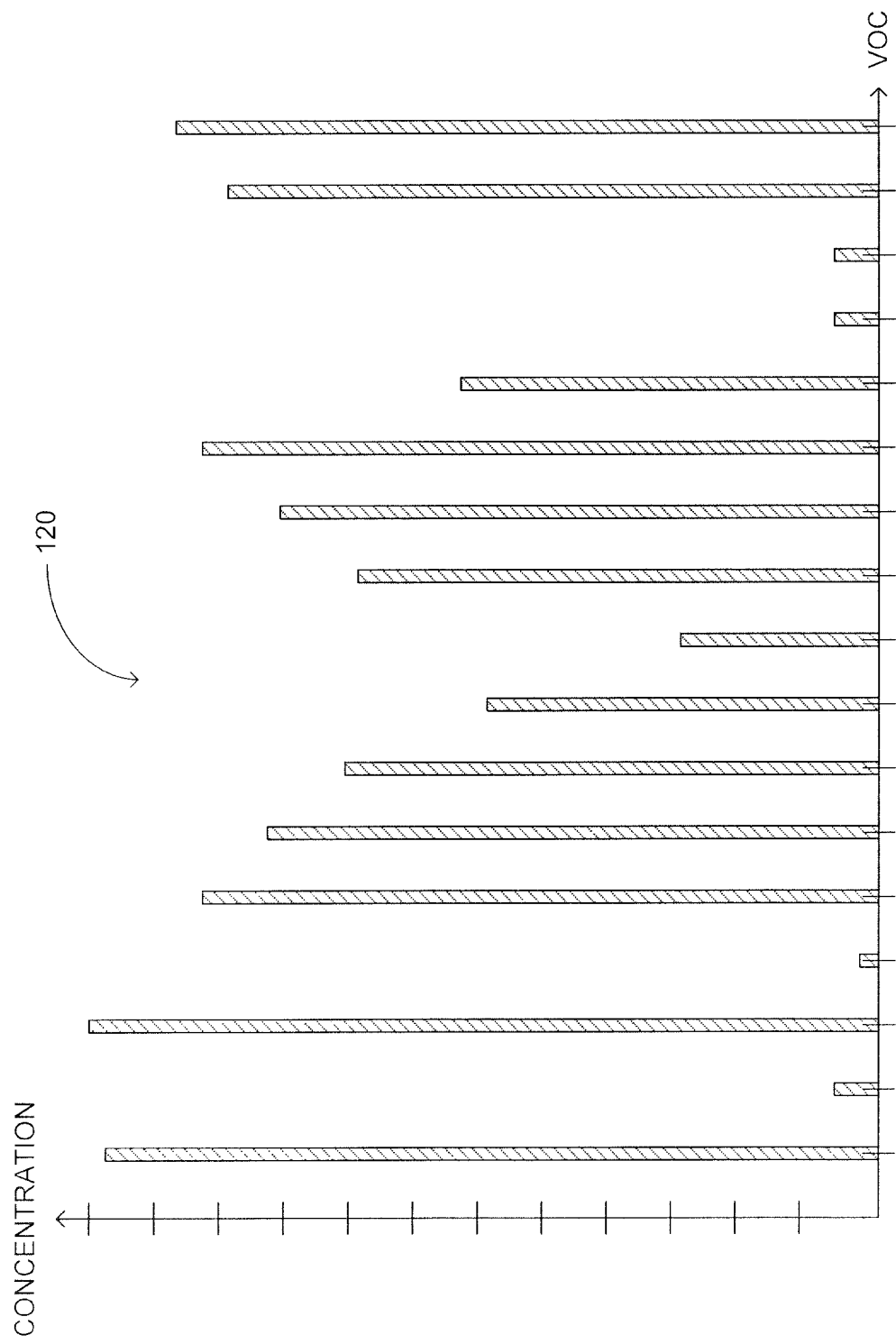
FIGS. 2A and 2B are, respectively, schematic illustrations of VOC emission data and a differential VOC profile, in accordance with another embodiment of the disclosed technique.
Figure 2B:
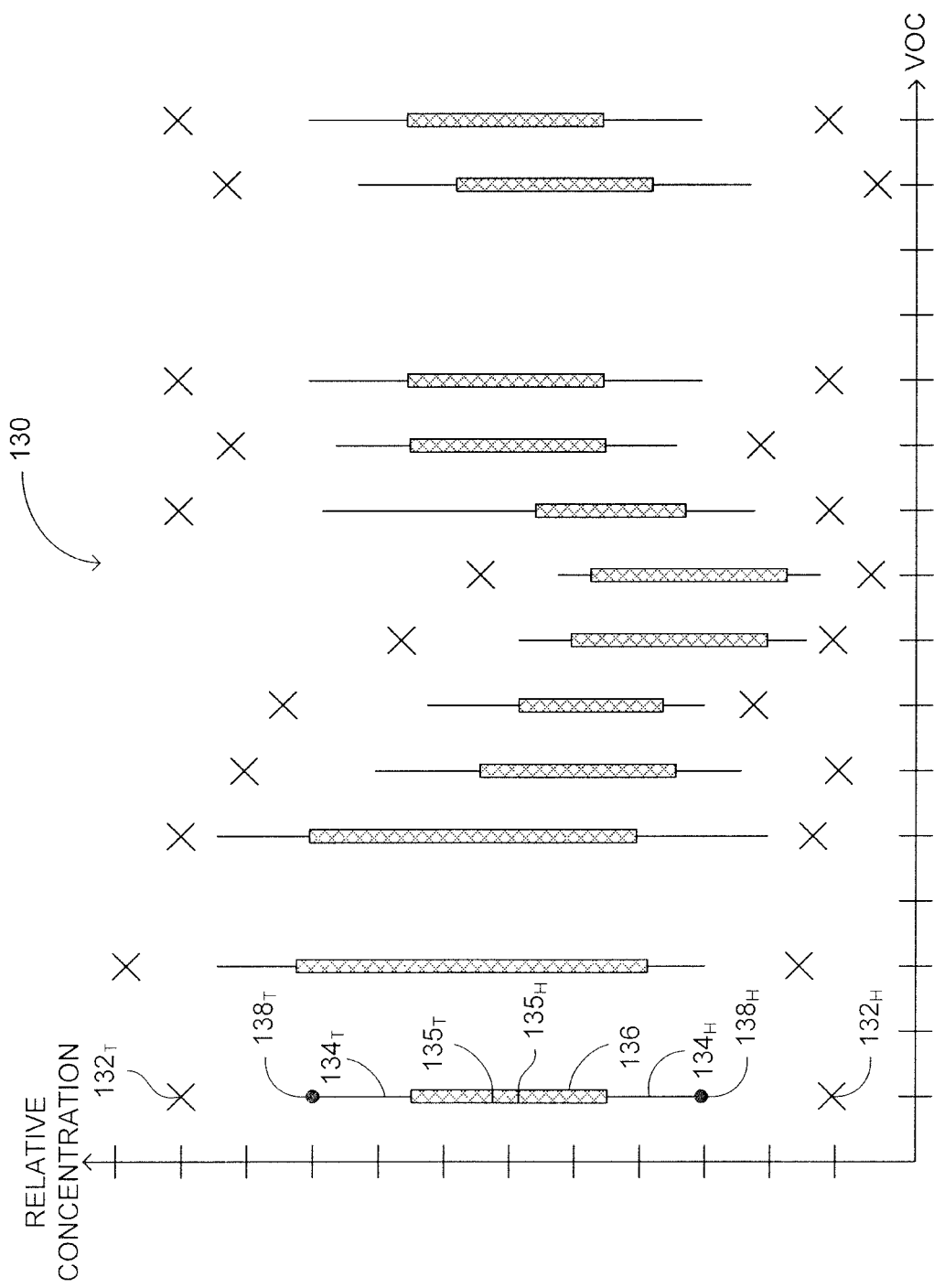

Reference is now made to FIGS. 2A and 2B, which are, respectively, schematic illustrations of VOC emission data, generally referenced 120, and a differential VOC profile, generally referenced 130, in accordance with another embodiment of the disclosed technique. With reference to FIG. 2A, the horizontal axis represents the selected VOCs which are being measured and the vertical axis represents the concentration levels. As mentioned above, the concentration levels may be measured in parts-per notation (e.g., ppm's, ppb's, ppt's) or as count rates of the VOC molecules. In general, there are over 1800 different VOCs that are excreted or found in a typical person's breath and body fluids. However, not all these VOCs are necessarily measured.

With reference to FIG. 2B, dynamic differential VOC profile 130 is defined by healthy and target VOC profiles determined from VOC emission data of healthy and target cells culture, from VOC concentration levels predicted to exists in the breath and/or body fluids and the measured VOC concentration levels in the breath and/or body fluids. In FIG. 2B, the symbol 'X' $132_T$, represents the relative VOC concentration levels measured from target cells culture relative to the symbol 'X' $132_H$, that represents the VOC concentration levels measured from healthy cells culture. Line $134_T$, and the part of the square 136 above the line $135_H$, represents the target VOC concentration levels predicted to be observed in the breath and/or body fluids and/or cells culture in patients with an expression or overexpression of target cells. Line $134_H$, and the part of the square 136 under line $135_T$, represents the healthy VOC concentration levels predicted to be observed in the breath and/or body fluids and/or cell cultures of patients without the expression or overexpression of the target cells. The predicted VOC concentration levels are determined by applying a diffusion model (e.g., Farhi's equation or a modified Farhi's model, both further explained below) and cell growth equation to the VOC concentration levels measured from the healthy and target cells cultures. Square 136 represents the range of VOC emission data measured from the breath and/or body fluids in healthy patients and patients with an expression or overexpression of the target cells. The line $135_T$ represents the highest concentration level measured in the healthy patient group. The line $135_H$ represents the lowest concentration level of the VOC measured in the patient group with an expression or overexpression of the target cells. The range between line $135_T$ and $135_H$ represents the threshold between maximum normal VOC representation, and target cell VOC representation of the VOCs in breath, bodily fluids or cell cultures. The range between point $138_H$ and $138_T$ is dynamic range of the VOC emitted in the breath and/or body fluids. As depicted in FIG. 2A, not all measured VOCs are included in VOC profile 130, for example, when the measured concentration level is below a threshold.

Building VOC Profiles Database

Figure 3A:
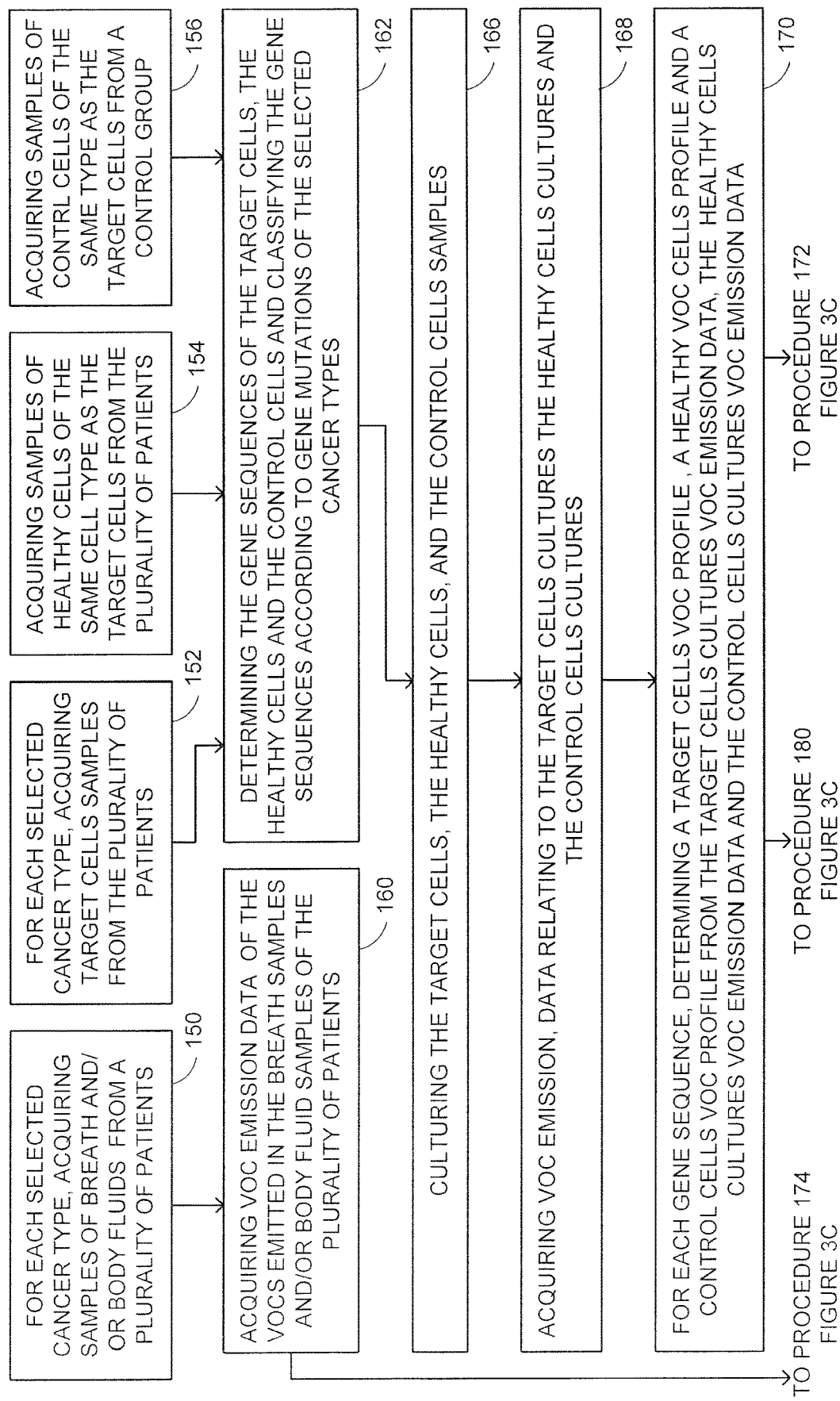
FIGS. 3A, 3B and 3C are a schematic illustration of an exemplary method for associating VOC emissions with a corresponding cancer type in a selected population, operative in accordance with a further embodiment of the disclosed technique.
Figure 3B:
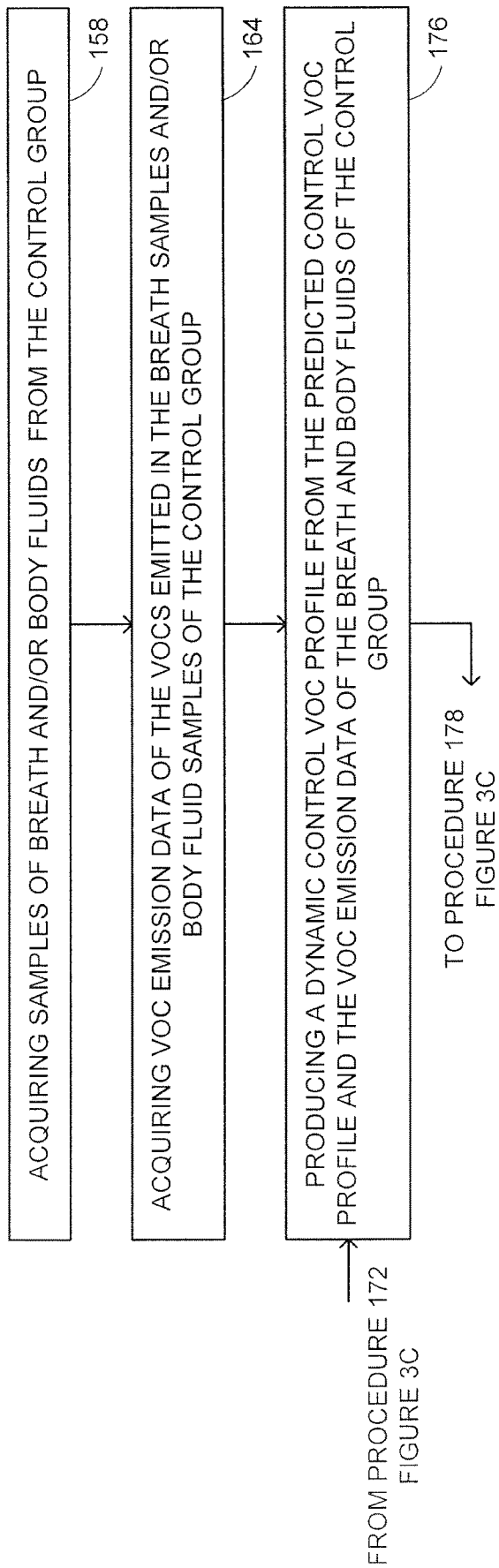
Figure 3C:
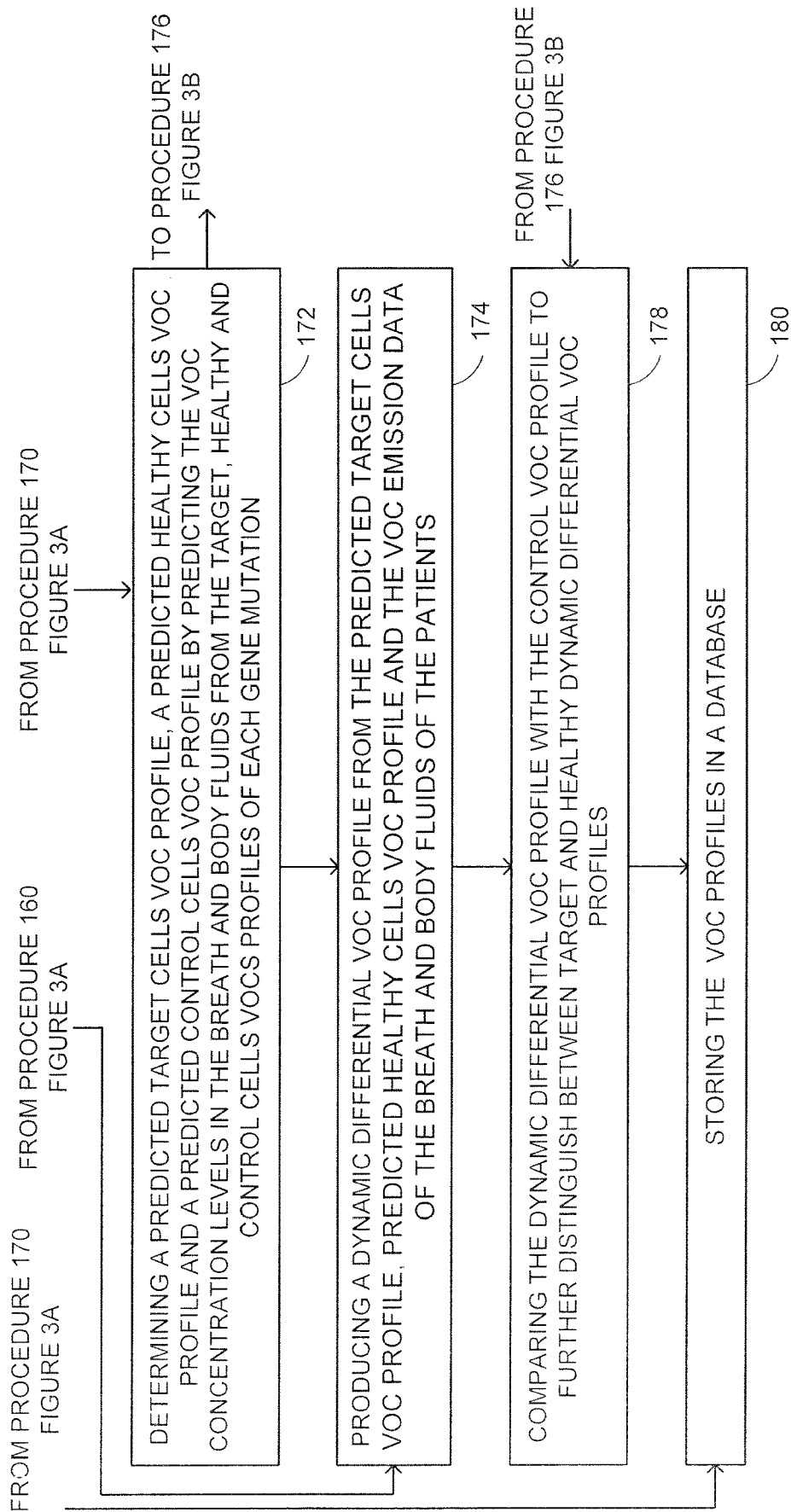
Figure 4A:
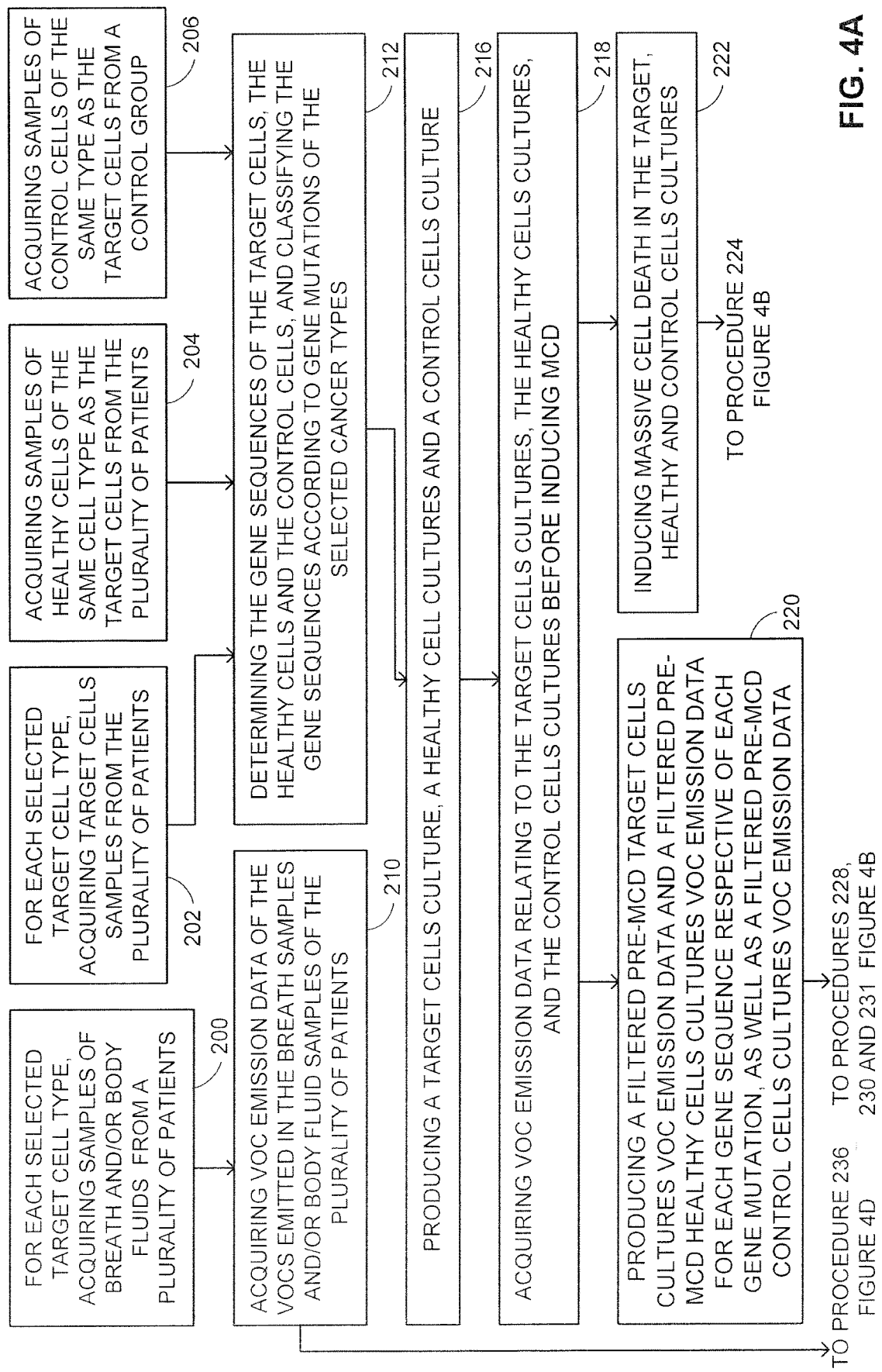
FIGS. 4A, 4B, 4C and 4D are a schematic illustration of a method for associating VOC emissions with target cells before and after treatment in a selected population, operative in accordance with another embodiment of the disclosed technique.
Figure 4B:
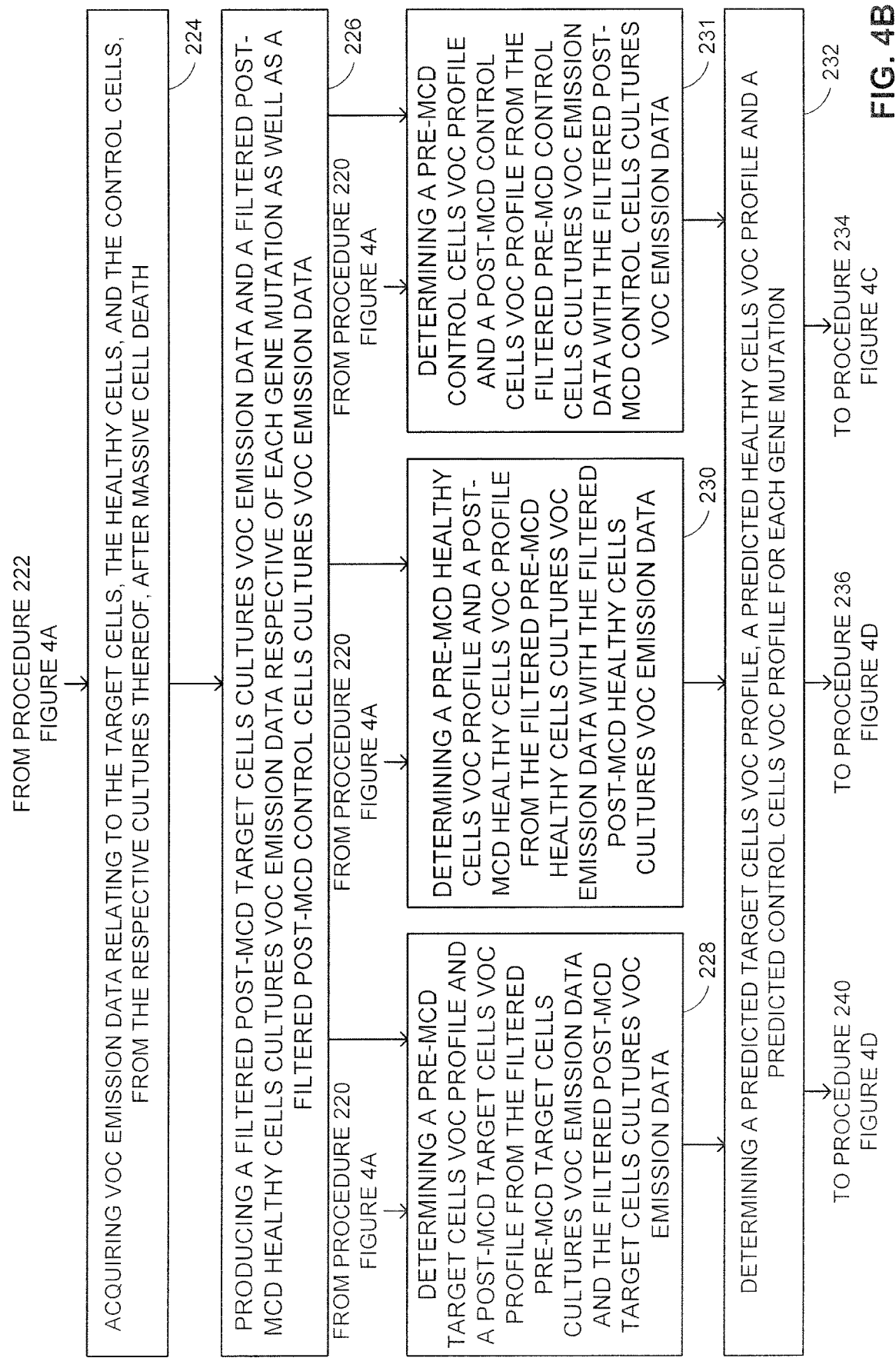
Figure 4C:
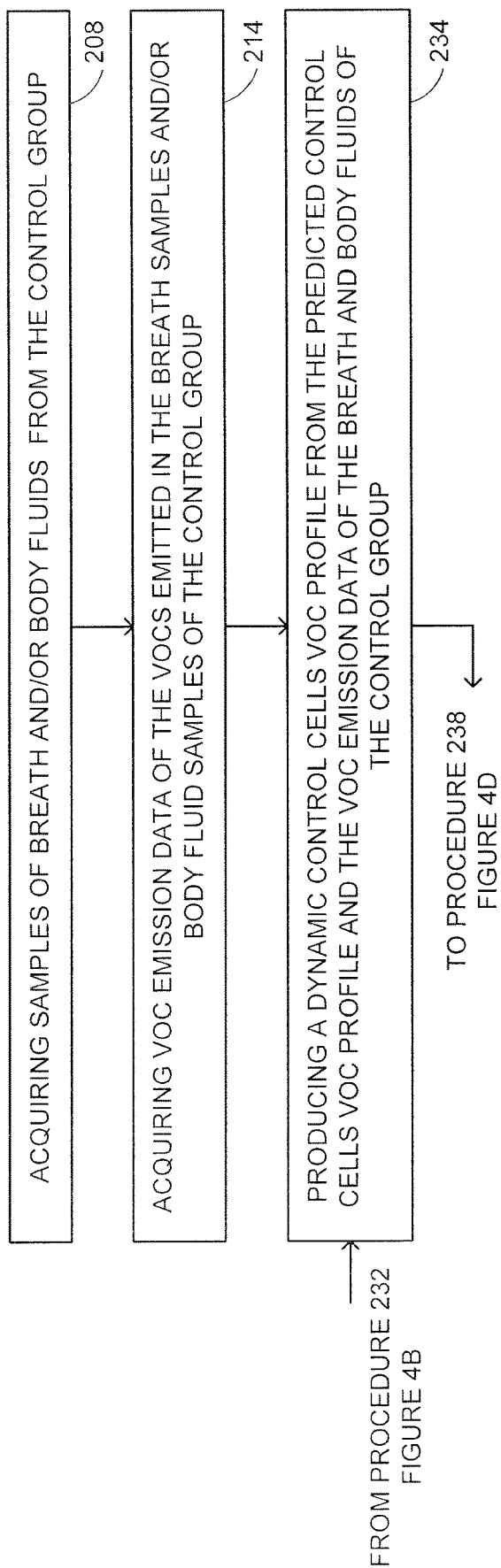
Figure 4D:
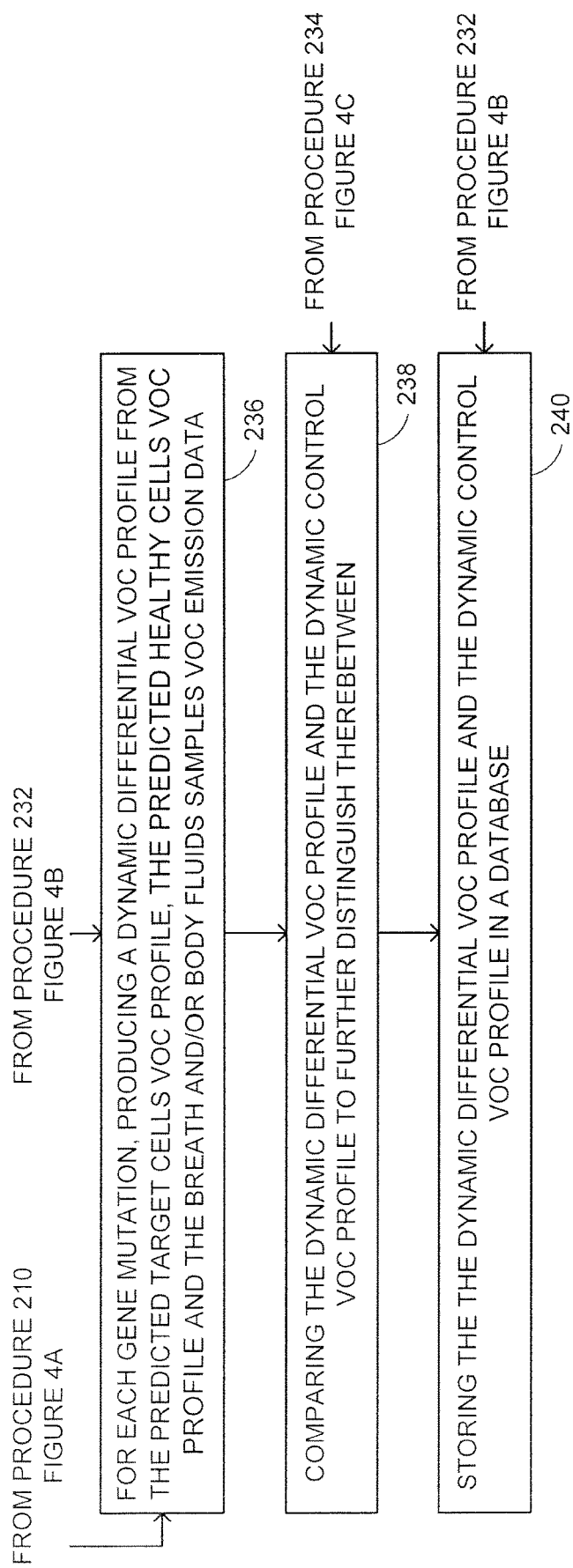

Reference is now made to FIGS. 3A, 3B and 3C, which are a schematic illustration of an exemplary method for associating VOC emissions with a corresponding cancer type in a selected population, operative in accordance with a further embodiment of the disclosed technique. In procedure 150, at least one of breath and body fluid (e.g., blood, urine or sweat) samples are acquired for each selected cancer type, from a plurality of patients. The term 'cancer type' relates to the type of cancer (e.g., ovarian, breast, bladder, skin, colon, etc.) as well as to the genetic subtype of the cancer (e.g., HER2+, HER triple negative, etc.). Since the cancer type is known before the samples are acquired, each breath and body fluid sample is associated with a corresponding cancer type. After procedure 150, the method proceeds to procedure 160.

In procedure 152, for each selected cancer type, target cells samples are acquired from the plurality of patients. In the example brought forth in FIGS. 3A-3C, the target cells are carcinogenic cells of a respective cell type. These target cells samples are acquired, for example, by a biopsy procedure. After procedure 152, the method proceeds to procedure 162.

In procedure 154, samples of healthy cells, of the same cell type as the target cells, are acquired from the plurality of patients. These healthy cells samples may also be acquired, for example, by a biopsy procedure. After procedure 154, the method proceeds to procedure 162.

In procedure 156, samples of control cells of the same type of the target cells are acquired from a control group. Control cells are healthy cells acquired from a control group. The control cells may also be acquired, for example, by a biopsy procedure. After procedure 156, the method proceeds to procedure 162.

In procedure 158, samples of breath and/or body fluids are acquired from the control group. After procedure 158, the method proceeds to procedure 164.

In procedure 160, VOC emission data of at least one of the breath and body fluid samples of the patients is acquired. With reference to FIG. 1, analysis device 102 acquires emission data of at least one of the breath and body fluids. After procedure 160, the method proceeds to procedure 174.

In procedure 162, gene sequences of the target cells, the healthy cells, and the control cells are determined. These gene sequences are then classified according to known carcinogenic gene mutations of the selected cancer types. For example, there are currently over 315 known cancer causing mutations. This procedure is also referred to as molecular classification. After procedure 162, the method proceeds to procedure 166.

In procedure 164, VOC emission data of the VOCs emitted in the breath samples and/or body fluid samples of the control group is acquired. With reference to FIG. 1, analysis device 102 acquires emission data of at least one of the breath and body fluids of the control group. After procedure 164, the method proceeds to procedure 176.

In procedure 166, the target cells, the healthy cells, and the control cells samples are cultured. After procedure 166, the method proceeds to procedure 168.

In procedure 168, VOC emission data, relating to the target cells cultures, the healthy cells cultures and the control cells cultures is acquired is acquired from the respective cultures. With reference to FIG. 1, analysis device 102 acquires emission data relating to the target cells cultures the healthy cells cultures and the control cells cultures is acquired form the respective cultures. After procedure 168, the method proceeds to procedure 170.

In procedure 170, for each gene sequence, a target cells VOC profile, a healthy cells VOC profile and a control cells VOC profile, from the target cells cultures VOC emission data, the healthy cells cultures VOC emission data and the control cells cultures VOC emission data respective of each gene mutation are determined. Initially, the target cells cultures VOC emission data, the healthy cells cultures VOC emission data and the control cells cultures VOC emission data are filtered. In general, the target and healthy cells may produce VOC artifacts which are not related to the gene mutation. Comparing the target cells cultures VOC emission data and the healthy cells cultures VOC emission data with each other and with the control cells VOC emission data is employed to alleviate the effects of unrelated VOC artifacts, to better distinguish VOCs related to the selected gene mutations. For example, in some cases of breast cancer, a healthy cell may still have a cancerous gene and/or might be in the middle of the process of becoming a target cell. In some of such cases, the cancer may still not be fully active. Nevertheless, the expression of this gene shall be VOCs which would not be present in the control cells cultures VOC emission data and the breath and body fluids samples VOC emission data acquired from the control group. Thus, the expression of this gene in the healthy cells may be identified. The filtered target cells cultures VOC emission data is produced by comparing the target cells cultures VOC emission data with both the healthy cells cultures VOC emission data and the control cells cultures VOC emission data. Then, the filtered healthy cells cultures VOC emission data is produced by comparing the healthy cells cultures VOC emission data with both the filtered target cells cultures VOC emission data and the control cells cultures VOC emission data. Thereafter, the filtered control cells cultures VOC emission data is produced by comparing the control cells cultures VOC emission data with the filtered healthy cells cultures VOC emission data. Then, the target cells VOC profile is determined by comparing the filtered target cells cultures VOC emission data with both the filtered healthy cells cultures VOC emission data and with the filtered control cells cultures VOC emission data. The healthy cells VOC profile is determined by comparing the filtered healthy cells cultures VOC emission data with both the filtered target cells cultures VOC emission data and with the filtered control cells cultures VOC emission data. The control cells VOC profile is determined by comparing the filtered control cells cultures VOC emission data with the filtered healthy cells cultures VOC emission data. With reference to FIG. 1, processor 106 determines the target cells VOC profile, the healthy cells VOC profile, and the control cells VOC profile for each gene sequence, from the target cells cultures VOC emission data, the healthy cells cultures VOC emission data and the control cells cultures VOC emission data respective of each gene mutation. After procedure 170, the method proceeds to procedures 172 and 180.

In procedure 172, a predicted target cells VOC profile, a predicted healthy cells VOC profile and a predicted control cells VOC profile are determined by predicting the VOC concentration levels in the breath and body fluids from the target cells VOC profiles, healthy cells VOC profiles and control cells VOC profiles of each gene mutation. The VOC concentration levels are predicted by using a diffusion model such as the Farhi equation or a modified Farhi model, both further elaborated below. Since VOC profiles are associated with corresponding gene mutations, the predicted VOC profiles are also associated with corresponding gene mutations. With reference to FIG. 1, processor 106 determines a predicted target cells VOC profile, a predicted healthy cells VOC profile and a predicted control cells VOC profile. After procedure 172, the method proceeds to procedures 174 and 176.

In procedure 174, a Dynamic Differential VOC profile is produced from the predicted target cells VOC profile, predicted healthy cells VOC profile and the VOC emission data of the breath and body fluids of the patients. This Dynamic Differential VOC profile is produced by minimizing the error between the predicted target cells VOC profile, predicted healthy cells VOC profile and the VOC emission data of the breath and body fluid samples. Since each predicted target cells VOC profile and predicted healthy cells VOC profile are associated with corresponding gene mutations, each Dynamic Differential VOC profile is also associated with corresponding gene mutations. With reference to FIG. 1, processor 106 determines a Dynamic Differential VOC profile for each gene mutation. From procedure 174 the method proceeds to procedure 178.

In procedure 176, a dynamic control VOC profile is produced from the predicted control cells VOC profile and the VOC emission data of the breath and body fluids of the control group. Similar to the dynamic differential VOC profile, the dynamic control VOC profile is produced by minimizing the error between the predicted control cells VOC profile and the VOC emission data of the breath and body fluid samples of the control group. With reference to FIG. 1, processor 106 determines a dynamic control VOC profile for each gene mutation. From procedure 176 the method proceeds to procedure 178.

In procedure 178, the Dynamic Differential VOC profile is compared with the dynamic control VOC profile to further distinguish therebetween. With reference to FIG. 1, processor 106 compares the Dynamic Differential VOC profile with the dynamic control VOC profile to further distinguish therebetween. From procedure 178 the method proceeds to procedure 180.

In procedure 180, the VOC profiles are stored in a database. With reference to FIG. 1, processor 106 stores the Dynamic Differential VOC profile and the Dynamic control VOC profile and the corresponding cancer type in database 104.

In some cases, the VOC emission of target and healthy cells may be different before and after treatment. For example, in carcinogenic target cells, Massive Cell Death (MCD) treatments (e.g., radiation treatment, chemotherapy treatments) are employed and the VOCs emitted by the healthy and target cells may be different before and after the MCD treatment. To determine the influence of MCD on the VOCs emitted by the patient, MCD is induced in cell cultures in such a way that does not generate VOC artifacts (e.g., by employing flash freeze techniques, or Ultra Violet—UV light techniques) and VOC emissions acquired prior to MCD and acquired after MCD are then associated with corresponding target cells for a selected population.

Reference is now made to FIGS. 4A, 4B, 4C and 4D, which are a schematic illustration of a method for associating VOC emissions with target cells before and after treatment in a selected population, operative in accordance with another embodiment of the disclosed technique. In procedure 200, breath and/or body fluids samples are acquired for each selected target cell type from a plurality of patients. After procedure 200, the method proceeds to procedure 210.

In procedure 202, for each selected target cells type, target cells samples are acquired from the plurality of patients. These target cells samples are acquired, for example, by a biopsy procedure. After procedure 202, the method proceeds to procedure 212.

In procedure 204, samples of healthy cells of the same cell type as the target cells are acquired from the plurality of patients. These healthy cells samples may also be acquired by a biopsy procedure. After procedure 204, the method proceeds to procedure 212.

In procedure 206, samples of control cells of the same type as the target cells are acquired from a control group. These control cells samples may also be acquired by a biopsy procedure. After procedure 206, the method proceeds to procedure 212.

In procedure 208, samples of breath and/or body fluids are acquired from the control group. After procedure 208, the method proceeds to procedure 214.

In procedure 210, VOC emission data of the VOCs emitted in the breath samples and/or body fluid samples are acquired from the plurality of patients. With reference to FIG. 1, analysis device 102 acquires emission data of at least one of the breath and body fluids from the plurality of patients. After procedure 210, the method proceeds to procedure 236.

In procedure 212, the gene sequences of the target cells, healthy cells and control cells are determined, and the gene sequences are classified according to molecular classification (genetic classification). After procedure 212, the method proceeds to procedure 216.

In procedure 214, VOC emission data of the VOCs emitted in the breath samples and/or body fluid samples of the control group is acquired. With reference to FIG. 1, analysis device 102 acquires emission data of at least one of the breath and body fluids of the control group. After procedure 214, the method proceeds to procedure 234.

In procedure 216, a target cells cultures, a healthy cell cultures and a control cells cultures are produced by culturing the target cells, the healthy cells, and the control cells samples. From procedure 216, the method proceeds to procedures 218 and 220.

In procedure 218, VOC emission data relating to the target cells cultures, the healthy cells cultures, and the control cells cultures is acquired before inducing MCD. With reference to FIG. 1, analysis device 102 acquires VOC emission data of target cells, healthy cells, and control cells before inducing MCD. After procedure 218, the method proceeds to procedure 220 and 222

In procedure 220, a filtered pre-MCD target cells cultures VOC emission data and a filtered pre-MCD healthy cells cultures VOC emission data for each gene sequence respective of each gene mutation, as well as a filtered pre-MCD control cells cultures VOC emission data are produced, to alleviate the effects of unrelated VOC artifacts and to better distinguish VOCs related to the selected gene mutations before inducing MCD. To that end, initially the filtered pre-MCD target cells cultures VOC emission data is produced by comparing the target cells cultures VOC emission data with both the healthy cells cultures VOC emission data, and with the control cells cultures VOC emission data, all of which were acquired before inducing MCD. Then, the filtered pre-MCD healthy cells cultures VOC emission data is produced by comparing the healthy cells cultures VOC emission data (i.e., which were acquired before inducing MCD) with both the filtered pre-MCD target cells cultures VOC emission data and with the control cells cultures VOC emission data (i.e., which were acquired before inducing MCD) acquired before inducing MCD. Thereafter, the filtered control cells cultures VOC emission data is determined by comparing the control cells cultures VOC emission data acquired before inducing MCD with the filtered pre-MCD healthy cells cultures VOC emission data. With reference to FIG. 1, processor 106 determines the filtered pre-MCD target cells cultures VOC emission data, the filtered pre-MCD healthy cells cultures VOC emission data, and the filtered pre-MCD control cells cultures VOC emission data for each gene sequence respective of each gene mutation. After procedure 220, the method proceeds to procedures 228, 230 and 231.

In procedure 222, massive cell death is induced in the target cells cultures, the healthy cells cultures and the control cells cultures. Preferably the MCD is induced in a manner that does not generate VOC artifacts (e.g., by employing flash freeze techniques or UV light techniques).

In procedure 224, VOC emission data relating to the target cells cultures, the healthy cells cultures, and the control cells cultures is acquired from the respective cultures thereof, after massive cell death. It is noted that the cells cultures employed before and after MCD are the same cultures. With reference to FIG. 1, analysis device 102 acquires VOC emission data of target cells, healthy cells, and control cells after massive cell death. After procedure 222, the method proceeds to procedure 226.

In procedure 226, a filtered post-MCD target cells cultures VOC emission data and a filtered post-MCD healthy cells cultures VOC emission data respective of each gene mutation and a filtered post-MCD control cells cultures VOC emission data are produced to alleviate the effects of unrelated VOC artifacts and to better distinguish VOCs related to the selected gene mutations after inducing MCD. Initially the filtered post-MCD target cells cultures VOC emission data is produced by comparing the target cells cultures VOC emission data acquired after inducing MCD with both the healthy cells cultures VOC emission data acquired after inducing MCD and with the control cells cultures VOC emission data acquired after inducing MCD. Then, the filtered post-MCD healthy cells cultures VOC emission data is produced by comparing the healthy cells cultures VOC emission data (i.e., acquired after inducing MCD) with both the filtered post-MCD target cells cultures VOC emission data and with the control cells cultures VOC emission data (i.e., that was acquired after inducing MCD). Thereafter, the filtered control cells cultures VOC profile is determined by comparing the control cells cultures VOC emission data (i.e., acquired after inducing MCD) with the filtered post-MCD healthy cells cultures VOC emission. With reference to FIG. 1, processor 106 determines the filtered post-MCD target cells cultures VOC emission data, the filtered post-MCD healthy cells cultures VOC emission data, and the filtered post-MCD control cells cultures VOC emission data for each gene sequence respective of each gene mutation. After procedure 226, the method proceeds to procedures 228, 230 and 231.

In procedure 228, a pre-MCD target cells VOC profile and a post-MCD target cells VOC profile are determined from the filtered pre-MCD target cells VOC emission data with the filtered post-MCD target cells VOC emission data. With reference to FIG. 1, processor 106 determines a pre-MCD target cells VOC profile and a post-MCD target cells VOC profile from the filtered pre-MCS target cells VOC emission data and the filtered post-MCD target cells VOC emission data. After procedure 228, the method proceeds to procedure 232.

In procedure 230, a pre-MCD healthy cells VOC profile and a post-MCD healthy cells VOC profile are determined from the filtered pre-MCD healthy cells cultures VOC emission data with the filtered post-MCD healthy cells cultures VOC emission data. With reference to FIG. 1, processor 106 determines a pre-MCD healthy cells VOC profile and a post-MCD healthy cells VOC profile from the filtered pre-MCD healthy cells cultures VOC emission data and the filtered post-MCD healthy cells cultures VOC emission data. After procedure 230, the method proceeds to procedure 232.

In procedure 231, a pre-MCD control cells VOC profile and a post-MCD control cells VOC profile are determined from the filtered pre-MCD control cells cultures VOC emission data with the filtered post-MCD control cells cultures VOC emission data. With reference to FIG. 1, processor 106 determines a pre-MCD control cells VOC profile and a post-MCD control cells VOC profile from the filtered pre-MCD control cells cultures VOC emission data with the filtered post-MCD control cells cultures VOC emission data. After procedure 231, the method proceeds to procedure 232.

In procedure 232, a predicted target cells VOC profile, a predicted healthy VOC profile and a predicted control cells VOC profile are determined for each gene mutation. The predicted target cells VOC profile is determined by predicting the VOC concentration levels in the breath and body fluids from the pre-MCD target cells VOC profile, post-MCD target cells VOC profile. The predicted healthy cells VOC profile is determined by predicting the VOC concentration levels in the breath and body fluids from the pre-MCD healthy cells VOC profile, post-MCD healthy cells VOC profile. The predicted control cells VOC profile is determined by predicting the VOC concentration levels in the breath and body fluids from the pre-MCD control cells VOC profile, post-MCD control cells VOC profile. The VOC concentration levels are predicted by using a diffusion model such as the Farhi's equation or a modified Farhi's model, both further elaborated below. With reference to FIG. 1, processor 106 determines a predicted target cells VOC profile, a predicted healthy cells VOC profile, and a predicted control cells VOC profile. After procedure 232, the method proceeds to procedures 234, 236 and 240.

In procedure 234, a Dynamic control cells VOC profile is produced from the predicted control cells VOC profile and the VOC emission data of the breath and body fluids of the control group. Similar to the Dynamic Differential VOC profile, the Dynamic control VOC profile is produced by minimizing the error between the predicted control cells VOC profile and the VOC emission data of the breath and body fluid samples of the control group. With reference to FIG. 1, processor 106 determines a Dynamic control VOC profile for each gene mutation. After procedure 234, the method proceeds to procedure 238.

In procedure 236, a Dynamic Differential VOC profile is produced from the predicted target cells VOC profile, the predicted healthy cells VOC profile and the VOC emission data of the breath and/or body fluids samples for each gene mutation. With reference to FIG. 1, processor 106 produces a Dynamic Differential VOC profile from the predicted target cells VOC profile, the predicted healthy cells VOC profile and the breath and/or body fluids samples VOC emission data for each gene mutation. After procedure 236, the method proceeds to procedure 238.

In procedure 238, the Dynamic Differential VOC profile is compared with the Dynamic control VOC profile to further distinguish therebetween. With reference to FIG. 1, processor 106 compares the Dynamic Differential VOC profile with the Dynamic control VOC profile to further distinguish therebetween. After procedure 238, the method proceeds to procedure 240.

In procedure 240, the Dynamic Differential VOC profile and the Dynamic control VOC profile are stored in a database. With reference to FIG. 1, processor 106 stores the Dynamic Differential VOC profile and the Dynamic control VOC profile in database 104.

According to another embodiment of the disclosed technique, VOC emissions from the body and/or cultures of a patient or patients can be associated, for example, with known pathological conditions, which results from pathogens (e.g., normal flora or pathological flora) such as bacteria, viruses, fungi and the like. In some case, (e.g., the *E. coli* bacteria), these pathogens may naturally exist in the body and the pathological conditions is characterized by an increased or decreased number of such pathogens. The pathological condition may also exhibit different VOC emission before and after treatment as result of VOC artifacts related to the effect of the treatment on another bacteria or pathogens in the body (e.g., VOCs artifacts related to the antibiotics effect on the normal flora in the intestines).

Figure 5A:
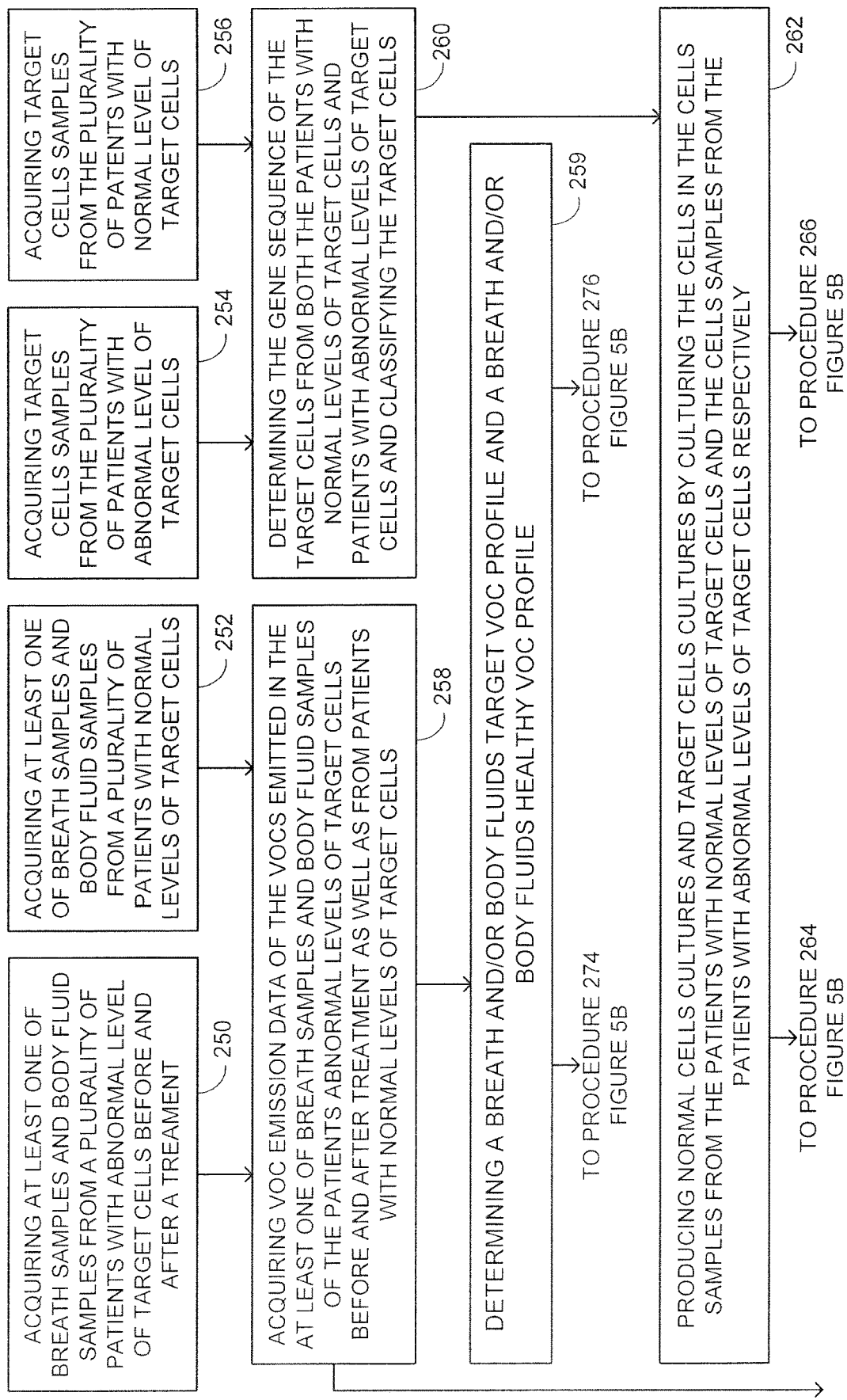
Figure 5B:
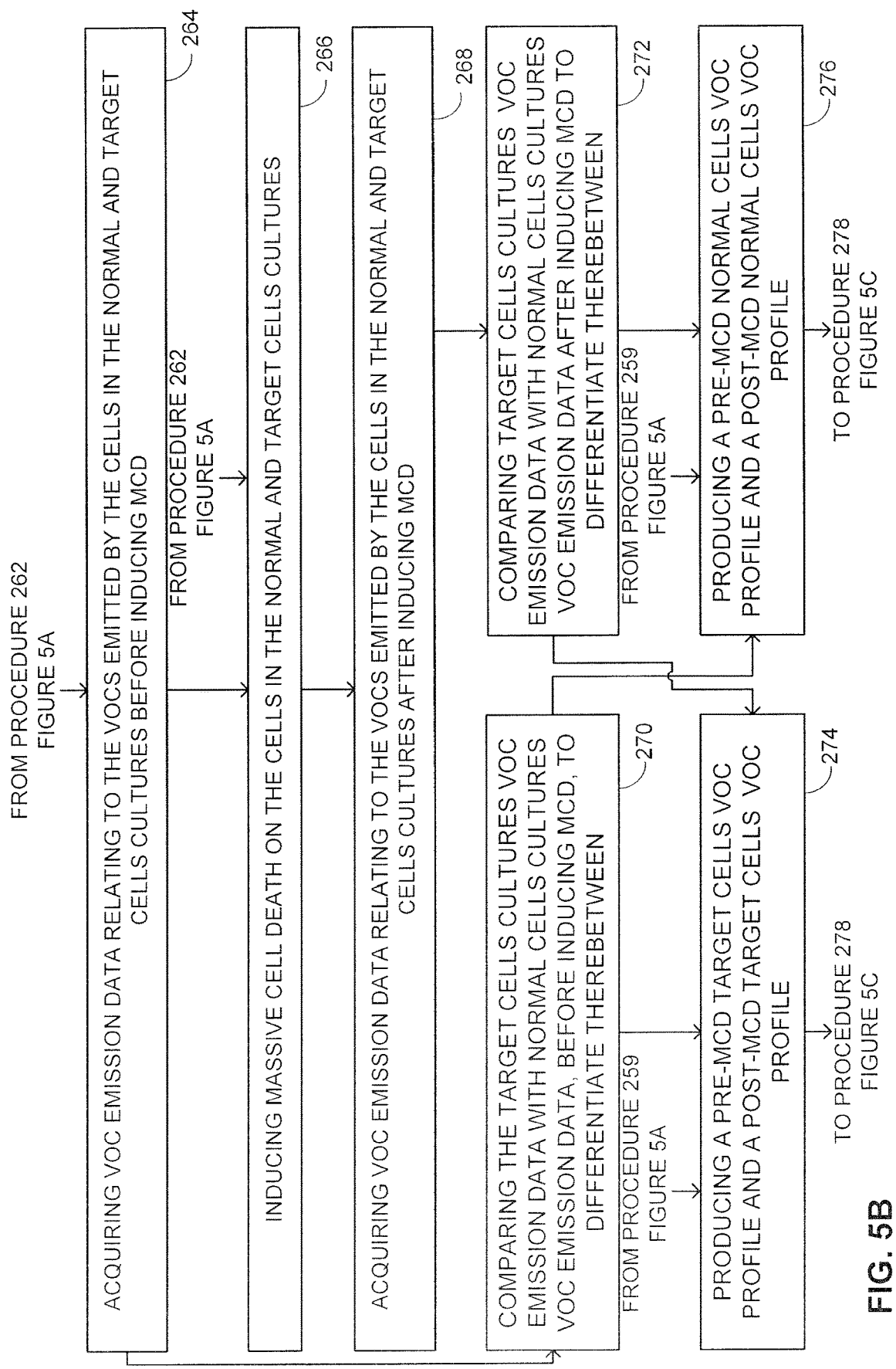
Figure 6A:
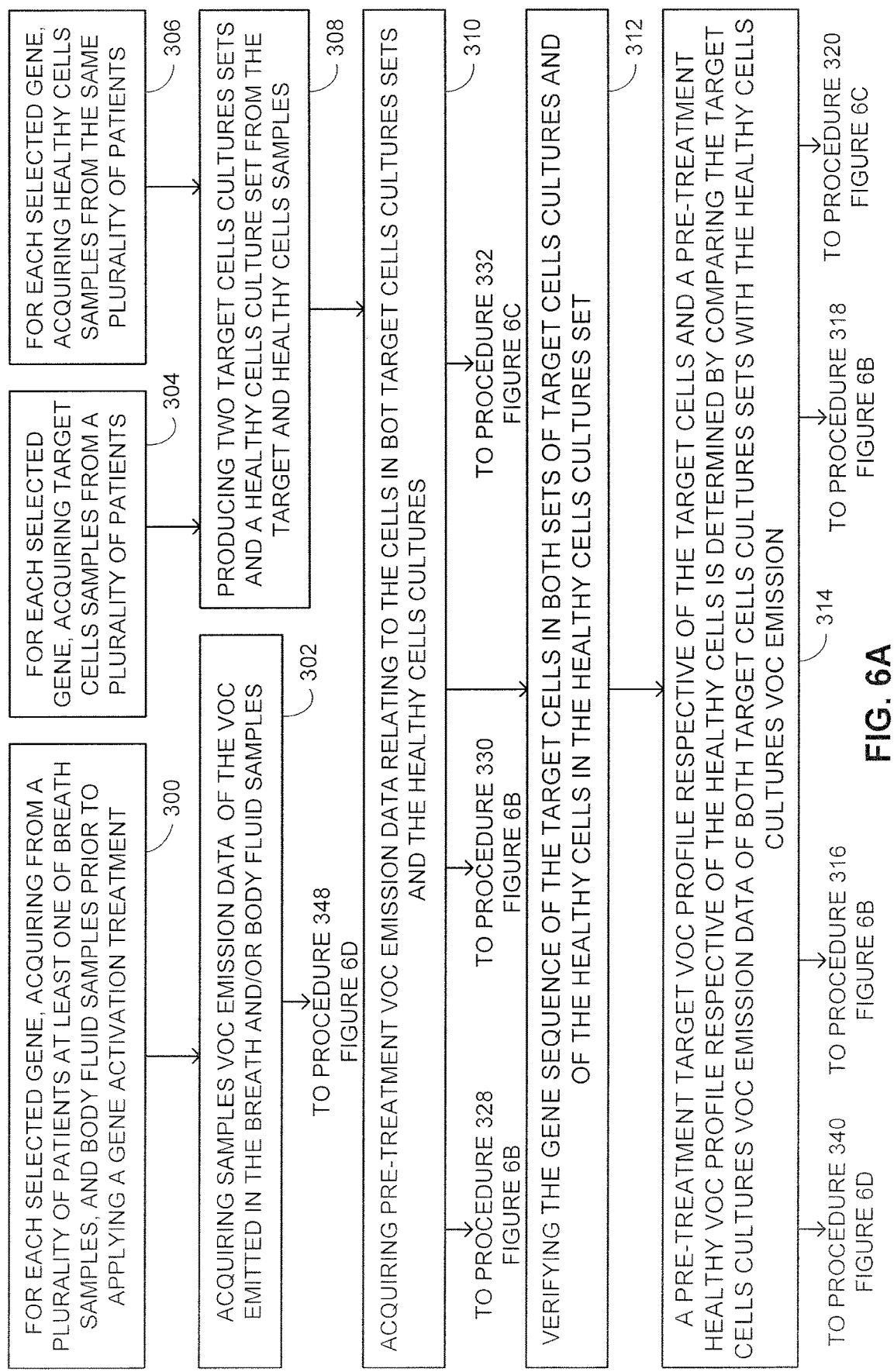
Figure 6B:
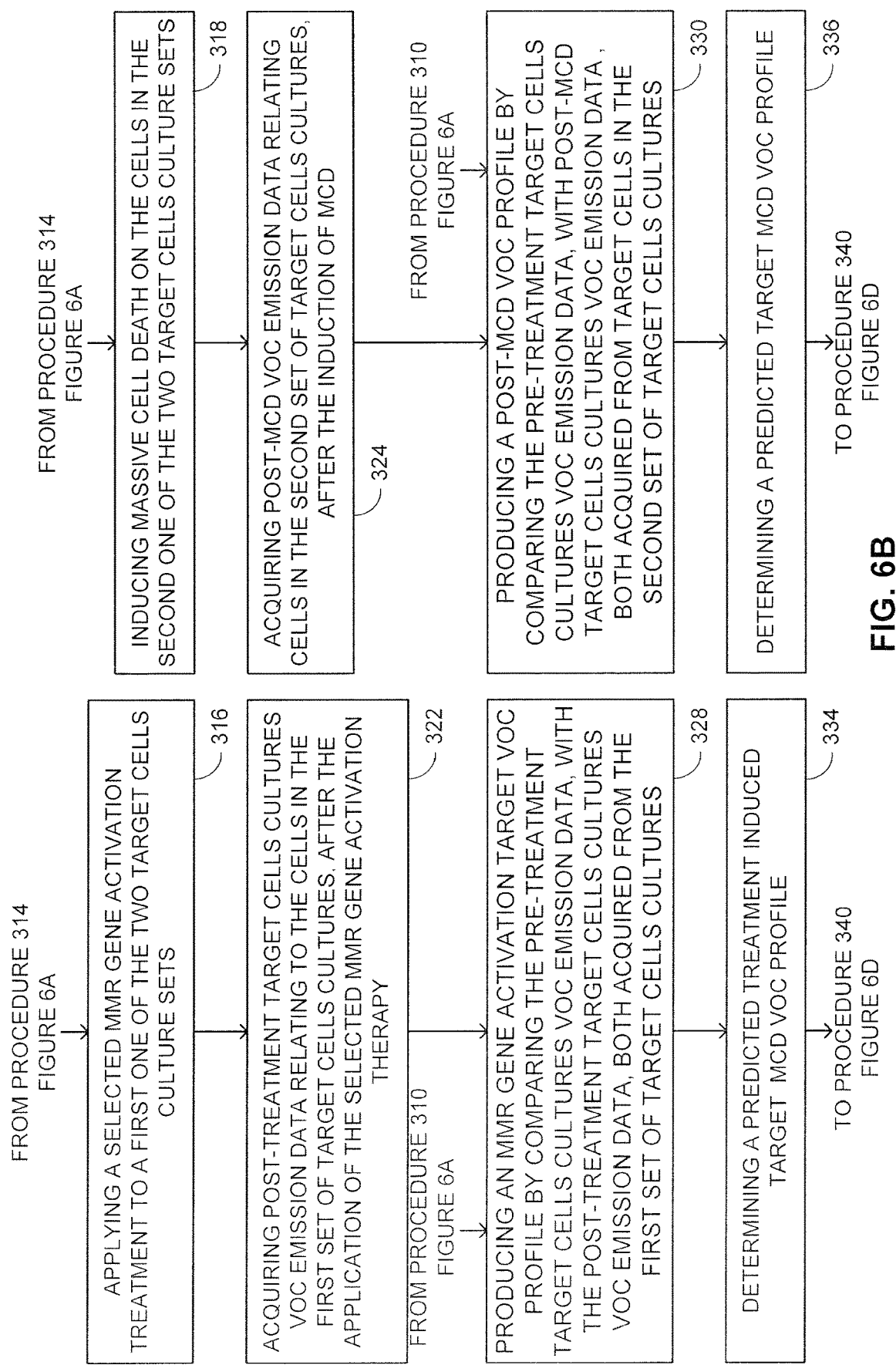
Figure 6D:
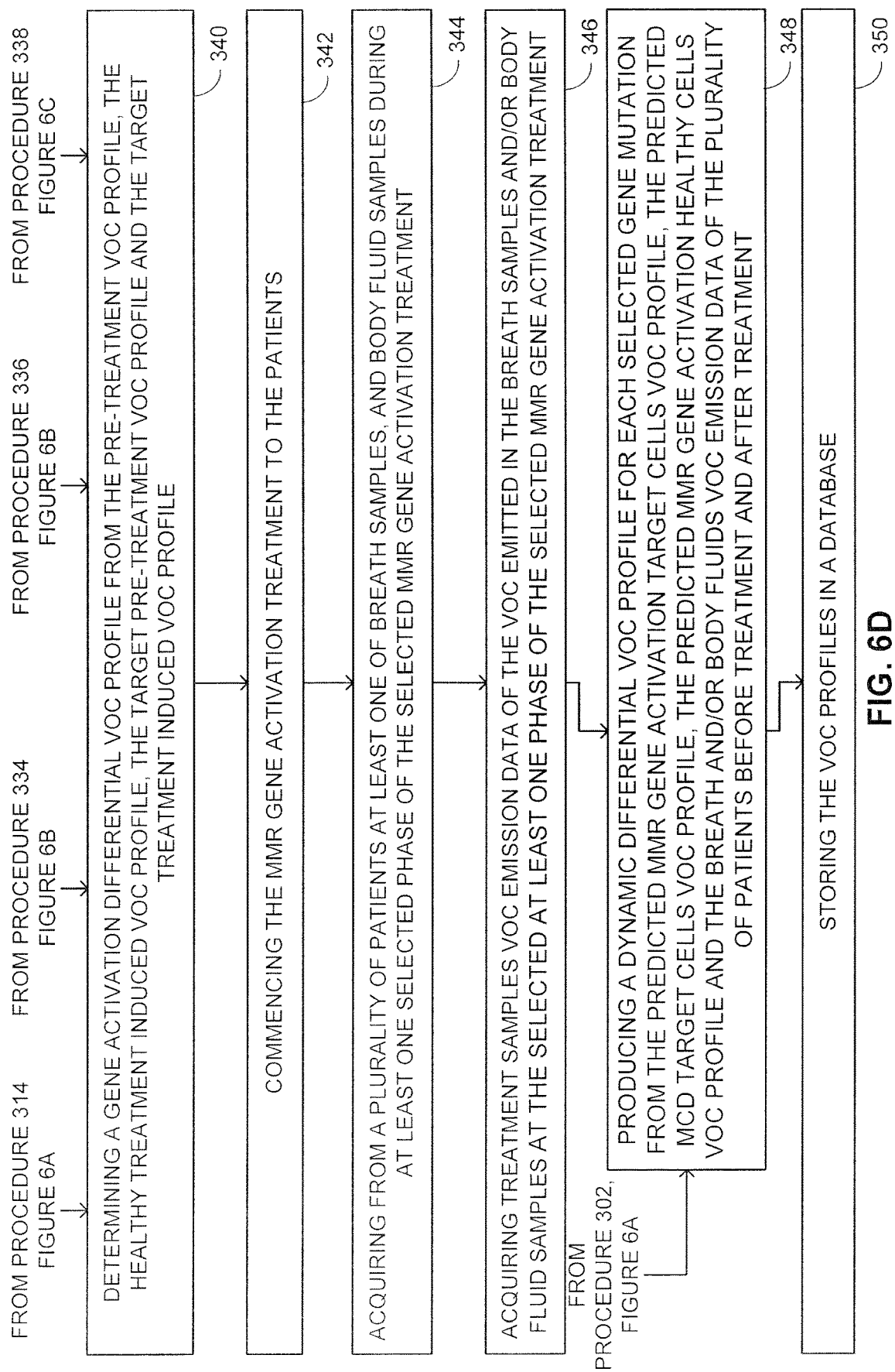

Reference is now made to FIGS. 5A, 5B and 5C, which are a schematic illustration of a method for associating VOC profiles with pathological conditions, which results from pathogens, operative in accordance with a further embodiment of the disclosed technique.

In procedure 250, at least one of breath samples and/or body fluid samples from a plurality of patients with abnormal levels of target cells are acquired before the patient receives any treatment relating to the target cells (e.g., before the patient takes antibiotics in the case of a bacteria pathogen such as Klebsiella pneumoniae), and at least one of breath samples and/or body fluid samples from the same plurality of patients is acquired after the patients has completed a treatment (i.e., the pathogen is no longer symptomatic and/or no longer present in the patient's cultures). It is noted that the samples taken after the successful treatment are taken after a period of time that includes the necessary period of time for the effects of the treatment to completely diminish, so VOC artifacts related to the treatment directly and indirectly are no longer present in the samples. After procedure 250, the method proceeds to procedure 258.

In procedure 252, at least one of breath samples and body fluid samples from a plurality of patients with normal levels of target cells are acquired. After procedure 252, the method proceeds to procedure 258.

In procedure 254, target cells samples from the plurality of patients with abnormal level of target cells are acquired before any treatment. After procedure 254, the method proceeds to procedure 260.

In procedure 256, target cells samples from the plurality of patients with normal level of target cells are acquired. After procedure 256, the method proceeds to procedure 260.

In procedure 258, VOC emission data is acquired, of the VOCs emitted in the at least one of breath samples and/or body fluid samples, from patients with abnormal levels of target cells acquired before and after a treatment (i.e., when the treatment was successful). In addition, VOC emission data of the VOCs emitted in the at least one of breath samples and/or body fluid samples, from patients with normal levels of target cells is also acquired. With reference to FIG. 1, analysis device 102 acquires emission data of the VOCs emitted in the at least one of breath samples and body fluid samples, acquired before any treatment from patients with abnormal levels of target cells and emission data of the VOCs emitted in the at least one of breath samples and body fluid samples acquired after a successful treatment that relates to the target cells (the samples are acquired from the same plurality of patients before and after treatment). Analysis device 102 further acquires the VOC emission data of the VOCs emitted in the at least one of breath samples and/or body fluid samples from a plurality of patients with normal levels of target cells. It is noted that the group of plurality of patients with abnormal levels of target cells and the group of plurality of patients with normal levels of target cells are two different groups. After procedure 258, the method proceeds to procedure 259 and 282.

In procedure 259, a breath and/or body fluids target VOC profile and a breath and/or body fluids healthy VOC profile are determined. The breath and/or body fluids target VOC profile is determine by comparing the VOC emission data acquired from a plurality of patients with abnormal level of target cells before treatment with both the VOC emission data acquired from the same plurality of patients with abnormal levels of target cells after successful treatment and with the VOC emission data acquired from patients with normal levels of the target cells. The a breath and/or body fluids healthy VOC profile is determined by comparing the breath and/or body fluids VOC emission data from a plurality of patients with normal levels of target cells with the breath and/or body fluids target VOC profile. With reference to FIG. 1, processor 106 determines a breath and/or body fluids target VOC profile and breath and/or body fluids healthy VOC profile. After procedure 259, the method proceeds to procedures 274 and 276.

In procedure 260, the gene sequence of the target cells from both the patients with abnormal levels of target cells and patients with normal levels of target cells are determined, and the target cells are classified. The gene sequence of target cells from the patients with abnormal and—normal levels of target cells are determined for molecular classification and to detect if the target cells from the patients with abnormal levels of target cells mutated. After procedure 260 the method proceeds to procedure 262.

In procedure 262, target cells cultures and normal cells cultures are produced by culturing the cells in the cells samples from the patients with abnormal levels of target cells and the cells samples from the patients with—normal levels of target cells respectively. After procedure 262, the method proceeds to procedures 264 and 266.

In procedure 264, VOC emission data relating to the VOCs emitted by the cells in the target and normal cells cultures is acquired before inducing MCD. With reference to FIG. 1, analysis device 102 acquires VOC emission data relating to the VOCs emitted by the—target and normal cell cultures before inducing MCD. After procedure 264, the method proceeds to procedures 266 and 270.

In procedure 266, Massive Cell Death is induced on the cells in the target and normal cells cultures. Similar to as described above, MCD is induced in a manner that does not produce VOC artifacts (e.g., flash freeze, UV light). After procedure 266, the method proceeds to procedure 268.

In procedure 268, VOC emission data relating to the VOCs emitted by the cells in the target and normal cells cultures is acquired after inducing MCD. It is noted that the cell cultures employed to acquire the VOC emission data after MCD are the same cell cultures employed to acquire the VOC before MCD. With reference to FIG. 1, analysis device 102 acquires VOC emission data relating to the VOCs emitted by the cells cultures after inducing MCD. After procedure 268, the method proceeds to procedure 272.

In procedure 270, the target cells cultures VOC emission data acquired before inducing MCD is compared with normal cells cultures VOC emission data acquired before inducing MCD, to differentiate therebetween. Target cells cultures VOC emission data relates to VOC emission data of the cells cultures originating from the patients with abnormal levels of target cells before any treatment. Normal VOC emission data relates to VOC emission data of the cells cultures originating from the patients with Normal levels of target cells. With reference to FIG. 1, processor 106 compares target cells cultures VOC emission data with normal cells cultures VOC emission data before inducing MCD to differentiate therebetween. After procedure 270, the method proceeds to procedure 274.

In procedure 272, target cells cultures VOC emission data acquired after inducing MCD is compared with normal cells cultures VOC emission data after inducing MCD to differentiate therebetween. With reference to FIG. 1, processor 106 compares target cells cultures VOC emission data acquired after inducing MCD with normal cells cultures VOC emission data acquired after inducing MCD to differentiate therebetween. After procedure 272, the method proceeds to procedure 276.

In procedure 274, a pre-MCD target cells VOC profile and a post-MCD target cells VOC profile are produced. These profiles are produced by comparing target cells cultures VOC emission data acquired before inducing MCD with both the target cells cultures VOC emission data acquired after inducing MCD and the breath and/or body fluids target VOC profile. With reference to FIG. 1, processor 106 produces a pre-MCD target cells VOC profile and a post-MCD target cells VOC profile by comparing target cells cultures VOC emission data acquired before inducing MCD with both the target cells cultures VOC emission data acquired after inducing MCD and the breath and/or body fluids target VOC profile. After procedure 274, the method proceeds to procedure 278.

In procedure 276, a pre-MCD normal cells VOC profile and a post-MCD normal cells VOC profile are produced. These profiles are produced by comparing normal cells cultures VOC emission data acquired before inducing MCD is compared with both normal cells cultures VOC emission data acquired after inducing MCD and the breath and/or body fluids healthy VOC profile. With reference to FIG. 1, processor 106 produces a pre-MCD normal cells VOC profile and a post-MCD normal cells VOC profile by comparing normal cells cultures VOC emission data acquired before inducing MCD with both normal cells cultures VOC emission data acquired after inducing MCD and the breath and/or body fluids healthy VOC profile. After procedure 276, the method proceeds to procedure 278.

In procedure 278, a predicted target VOC profile and a predicted target VOC profile are determined. The predicted target VOC profile is determined by predicting the concentration levels in the breath and body fluids from the pre-MCD target cells VOC profile and the post-MCD target cells VOC profile. The predicted healthy VOC profile is determined by predicting the concentration levels in the breath and body fluids from the pre-MCD and the post-MCD healthy VOC profile. The VOC concentration levels are predicted by using a diffusion model such as the Farhi equation or a modified Farhi's model, both further elaborated below. With reference to FIG. 1, processor 106 determines a predicted target VOC profile and a predicted healthy VOC profile. After procedure 278, the method proceeds to procedures 280 and 282.

In procedure 280, producing abnormal response VOC profile and normal response VOC profile, related to the response of the patients to the target cells by comparing the breath and/or body fluids VOC emission data from a plurality of patients with abnormal levels of target cells, with the breath and/or body fluids VOC emission data from a plurality of patients with normal levels of target cells, the predicted target VOC profile and the predicted healthy VOC profile. These response normal and abnormal VOC profiles are related to the response of the patient to the target cells (e.g., immune system, antibody's production). With reference to FIG. 1, processor 106 produces an abnormal response VOC profile and normal response VOC profile, related to the response of the patients to the target cells by comparing the breath and/or body fluids VOC emission data from a plurality of patients with abnormal levels of target cells with the breath and/or body fluids VOC emission data from a plurality of patients with normal levels of target cells, the predicted target VOC profile and the predicted healthy VOC profile. After procedure 280, the method proceeds to procedures 282 and 284.

In procedure 282, a Dynamic Differential VOC profile is produced from the predicted target VOC profile, the predicted healthy VOC profile, abnormal response VOC profile, abnormal response VOC profile, the breath and/or body fluids VOC emission data from a plurality of patients with abnormal levels of target cells and the breath and/or body fluids VOC emission data from a plurality of patients with normal levels of target cells. With reference to FIG. 1, processor 106 produces a Dynamic Differential VOC profile. After procedure 282, the method proceeds to procedure 284.

In procedure 284, the VOC profiles are stored in a database. With reference to FIG. 1, processor 106 stores the VOC profiles in database 104.

According to another embodiment of the disclosed technique, VOC emissions from the body of a patient or patients can be associated with the exposure of the target cells to MisMatch Repair Gene (MMR) activation treatment, by determining a Dynamic Differential VOC profile for each selected MMR gene activation therapy. Reference is now made to FIGS. 6A-6D, which are a schematic illustration of a method for determining a Dynamic Differential VOC profile for a selected MisMatch Repair (MMR) gene activation therapy, in accordance with another embodiment of the disclosed technique.

In procedure 300, for each selected gene, breath samples and/or body fluid samples are acquired from a plurality of patients prior to applying a MMR gene activation treatment. The genes are selected from genes that are suitable for MMR gene activation therapy. After procedure 300, the method proceeds to procedure 302.

In procedure 302, VOC emission data of the VOCs emitted in the breath samples and/or body fluids samples is acquired. With reference to FIG. 1, analysis device 102 acquires VOC emission data of the breath samples and/or body fluids samples. From procedure 302, the method proceeds to procedure 348.

In procedure 304, for each selected gene, target cells samples are acquired from the plurality of patients. From procedure 304, the method proceeds to procedure 308.

In procedure 306, for each selected gene, healthy cells samples, of the same type as the target cells are acquired from the same plurality of patients (i.e., a set of target cells and healthy cells is acquired from each patient in the plurality of patients for each selected gene). From procedure 306, the method proceeds to procedure 308.

In procedure 308, two target cells cultures sets and a healthy cells culture are produced from the target and healthy cells samples. For the sake of clarity of the explanation which follows, a first one of the target cells culture sets is referred to as 'cultures set A' and a second one of the target cells culture sets is referred to as 'cultures set B'. From procedure 308, the method proceeds to procedure 310.

In procedure 310, pre-treatment VOC emission data relating to cells in the two target cells cultures sets (i.e., cultures set A and cultures sets B) and the healthy cells cultures is acquired. With reference to FIG. 1, analysis device 102 acquires VOC emission data relating to the two target cell cultures and the healthy cells cultures. From procedure 310, the method proceeds to procedures 312, 328, 330, 331.

In procedure 312, the gene sequence of the target cells in both the target cells cultures sets (i.e., in cultures set A and in cultures set B) and of the healthy cells in the healthy cells cultures is verified. When determining a Dynamic Differential VOC profile for MMR gene activation therapy, the gene sequence of the target cells are already known and should only be verified, the healthy cells cultures are gene sequenced to insure the absence or determine the level of a pathological process or condition. From procedure 312, the method proceeds to procedure 314.

In procedure 314, a pre-treatment target cells VOC profile respective of the target cells and a pre-treatment healthy cells VOC profile respective of the healthy cells are determined by comparing the target cells cultures VOC emission data of both target cells cultures sets (i.e., of cultures set A and of cultures set B), with the healthy cells cultures VOC emission data of the healthy cells cultures. With reference to FIG. 1, processor 106 determines a pre-treatment target VOC profile and a pre-treatment healthy VOC profile. From procedure 314, the method proceeds to procedures 316, 318, 320, 340.

In procedure 316, a selected MMR gene activation treatment is applied to the cells in a first one of the two target cells cultures sets (i.e., cultures set A). From procedure 316, the method proceeds to procedure 322.

In procedure 318, Massive Cell Death is induced on the cells on in the second one of the two target cells culture sets (i.e., cultures set B), which was not expose to any treatment, in way that does not generate residual VOC artifacts (e.g., by employing flash freeze techniques, or Ultra Violet—UV light techniques to the target cells cultures). From procedure 318, the method proceeds to procedure 324.

In procedure 320, MMR gene activation therapy is applied to the cells in the healthy cells culture. From procedure 320, the method proceeds to procedure 326.

In procedure 322, post-treatment target cells cultures VOC emission data relating to the target cells in the first set of target cells cultures (i.e., cultures set A) is acquired after the application of the selected MMR gene activation treatment. With reference to FIG. 1, analysis device 102 acquires post-treatment target cells cultures VOC emission data relating to the target cells in cultures set A, after the application of the MMR gene activation treatment. After procedure 322, the method proceeds to procedure 328.

In procedure 324, post-MCD target cells cultures VOC emission data, relating to the target cells in the second set of target cells cultures (i.e., cultures set B) is acquired after the induction of MCD. With reference to FIG. 1, analysis device 102 acquires post-MCD target cells cultures VOC emission data relating to the target cells in cultures set B, after the induction of MCD. After procedure 324, the method proceeds to procedure 330.

In procedure 326, post-treatment healthy cells cultures VOC emission data relating to the healthy cells cultures is acquired after the selected MMR gene activation treatment. With reference to FIG. 1, analysis device 102 acquires post-treatment healthy cells cultures VOC emission data relating to the healthy cells cultures, after the application of the MMR gene activation treatment. After procedure 326, the method proceeds to procedure 332.

In procedure 328, producing an MMR gene activation target VOC profile by comparing the pre-treatment target cells cultures VOC emission data of the target cells acquired from target cells in the first set of target cells cultures (i.e., cultures set A), with the post-treatment target cells cultures VOC emission data of the target cells acquired from target cells in the first set of target cells cultures (i.e., cultures set A). The MMR gene activation target VOC profile relates to the VOCs emitted by the target cells cultures when the selected MMR gene activation treatment was applied. With reference to FIG. 1, processor 106 produces an MMR gene activation target VOC profile by comparing the pre-treatment target cells cultures VOC emission data of the target cells acquired from target cells in the first set of target cells cultures' with the post-treatment target cells cultures VOC emission data of the target cells acquired from the target cells in the first set of target cells cultures after being subjected to a selected MMR gene activation therapy. After procedure 328, the method proceeds to procedure 334.

In procedure 330, a post-MCD VOC profile is produced by comparing the pre-treatment target cells cultures VOC emission data of the target cells acquired from target cells in the second set of target cell cultures (i.e., culture set B), with post-MCD target cells cultures VOC emission data of the target cells acquired from target cells in the second set of target cells cultures (i.e., cultures set B) after MCD was induced. The post-MCD target cells VOC profile relates to the VOCs emitted by the target cells culture 'B' when MCD was induced in a way that does not generate residual VOCs. With reference to FIG. 1, processor 106 produces a post-MCD target cells VOC profile by comparing the pre-treatment target cells culture VOC emission data of the target cells acquired from target cells in the second set of target cultures before MCD with the post-MCD target cells cultures VOC emission data of the target cells acquired from the target cells in the second set of target cells cultures after inducing MCD. After procedure 330, the method proceeds to procedure 336.

In procedure 332, an MMR gene activation healthy cells VOC profile is produced by comparing the pre-treatment healthy cells cultures VOC emission data of the healthy cells, with the post-treatment VOC emission data of the healthy cells. The MMR gene activation healthy cells VOC profile relates to the VOCs emitted by the healthy cells cultures when the MMR gene activation treatment was applied. With reference to FIG. 1, processor 106 produces a MMR gene activation healthy cells VOC profile by comparing the pre-treatment healthy cells cultures VOC emission data of the healthy cells with the post-treatment healthy cells cultures VOC emission data of the healthy cells. After procedure 332, the method proceeds to procedure 338.

In procedure 334, a predicted MMR gene activation target cells VOC profile is determined by predicting the VOC concentration levels in the breath and body fluids from MMR gene activation target cells VOC profile. The VOC concentration levels are predicted by using a diffusion model such as the Farhi equation or a modified Farhi's model, both further elaborated below. With reference to FIG. 1, processor 106 determines a predicted MMR gene activation target cells VOC profile. After procedure 334, the method proceeds to procedure 342.

In procedure 336, a predicted post-MCD target cells VOC profile is determined by predicting the VOC concentration levels in the breath and body fluids from the post-MCD target cells VOC profile. The VOC concentration levels are predicted by using a diffusion model such as the Farhi equation or a modified Farhi's model, both further elaborated below. With reference to FIG. 1, processor 106 determines a predicted post-MCD target cells VOC profile. After procedure 336, the method proceeds to procedure 342.

In procedure 338, a predicted MMR gene activation healthy cells VOC profile is determined by predicting the VOC concentration levels in the breath and body fluids from MMR gene activation healthy cells VOC profile. The VOC concentration levels are predicted by using a diffusion model such as the Farhi equation or a modified Farhi's model, both further elaborated below. With reference to FIG. 1, processor 106 determines a predicted MMR gene activation healthy cells VOC profile. After procedure 338, the method proceeds to procedure 342.

In procedure 342, the patients MMR gene activation treatment is commenced. After procedure 342, the method proceeds to procedure 344.

In procedure 344, at least one of breath samples and body fluid samples are acquired from a plurality of patients during and/or after at least one selected phase of the selected MMR gene activation treatment. After procedure 344, the method proceeds to procedure 346.

In procedure 346, VOC emission data, of the VOCs emitted in the breath samples and/or body fluid samples of patients, is acquired at the at least one selected phase of the selected MMR gene activation treatment. With reference to FIG. 1, analysis device 102 acquires VOC emission data of the VOCs emitted in the breath samples and/or body fluid samples of patients during and/or after at least one selected phase of the selected MMR gene activation treatment. After procedure 346, the method proceeds to procedure 348.

In procedure 348, a Dynamic Differential VOC profile for each selected gene mutation is produced from the predicted MMR gene activation target cells VOC profile, predicted MCD target cells VOC profile, predicted MMR gene activation healthy cells VOC profile and the breath and/or body fluids VOC emission data of a plurality of patients before treatment and after treatment. It should be noted that for every patient breath and/or body fluids VOC emission data from a sample taken before a MMR gene activation treatment, a breath and/or body fluids VOC emission data from a sample taken during or after treatment has to be taken from the same patient. With reference to FIG. 1, processor 106 produces a Dynamic Differential VOC profile from the predicted MMR gene activation target cells VOC profile, predicted MCD target cells VOC profile, predicted MMR gene activation healthy cells VOC profile and the VOC emission data of a plurality of patients before being treated and during or after being treated with MMR gene activation therapy. After procedure 348, the method proceeds to procedure 350.

In procedure 350, the VOC profiles are stored in a database. With reference to FIG. 1, processor 106 stores the VOC profiles in database 104.

Figure 7A:
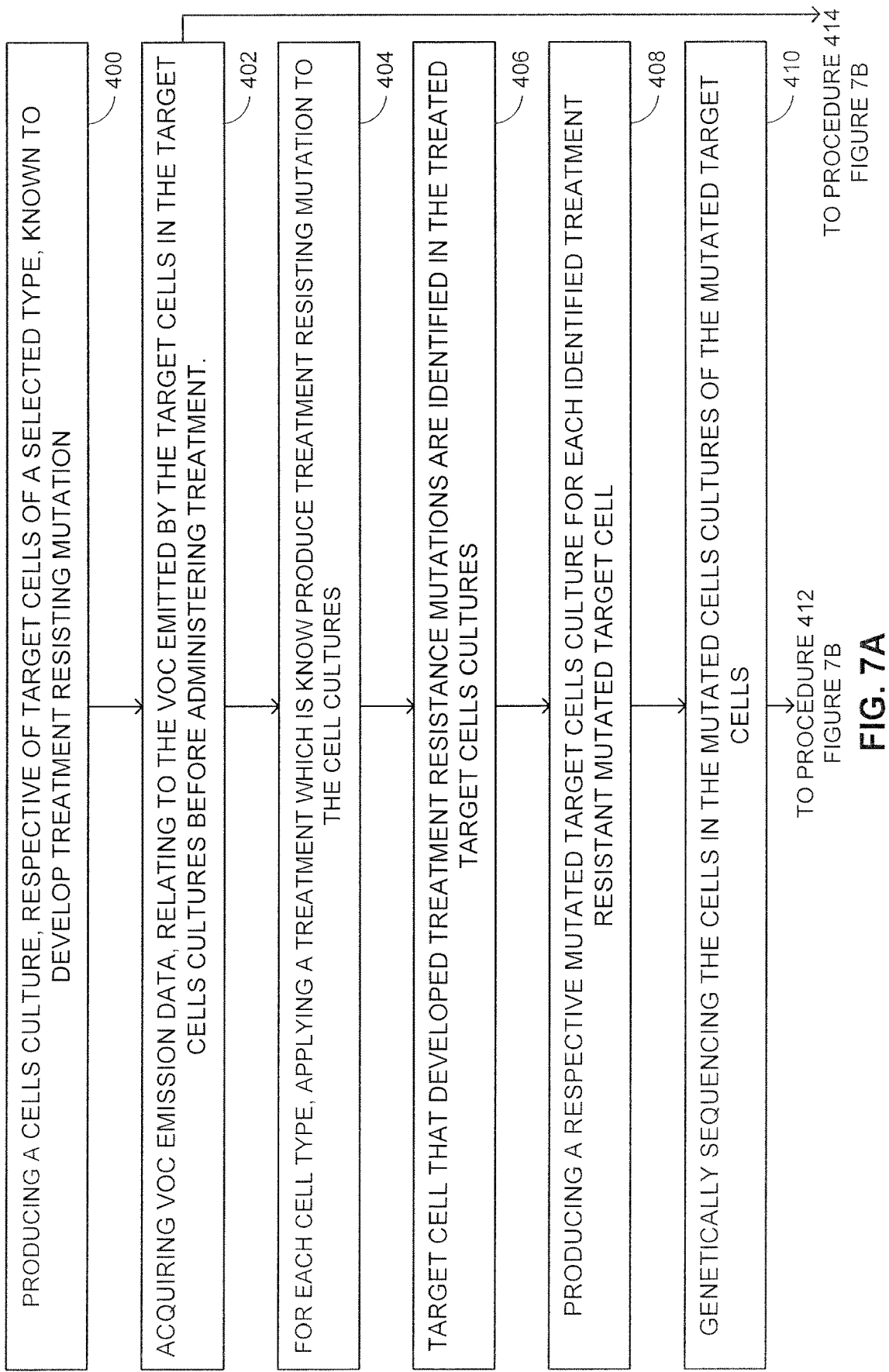
FIGS. 7A and 7B are a schematic illustration of a method for determining a VOC profile of target cells, which developed treatment resistant mutations from a selected treatment, operative in accordance with a further embodiment of the disclosed technique.
Figure 7B:
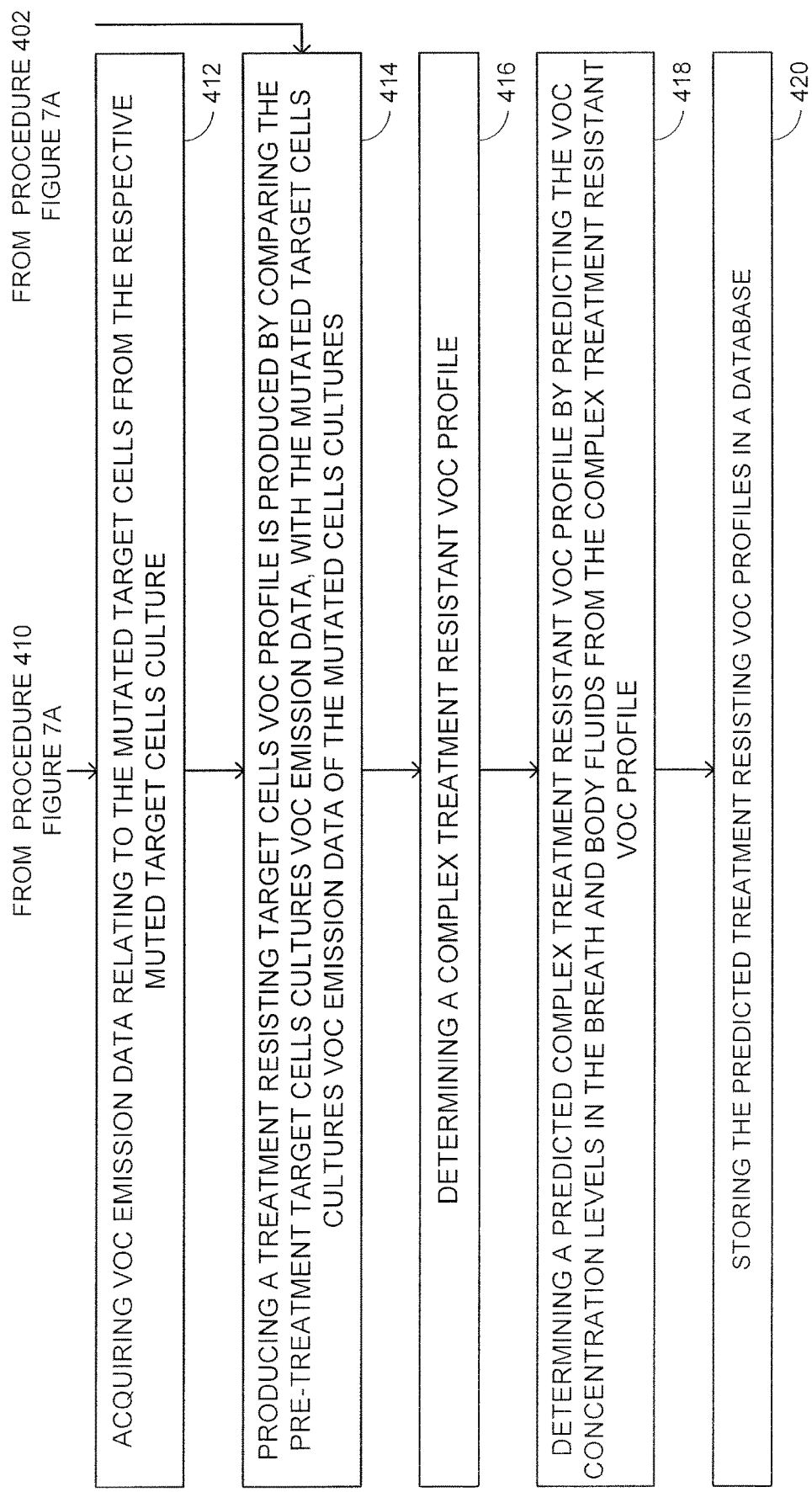

Measuring the VOCs may also be employed for determining if target cells have developed a treatment resistant mutation or mutations. Moreover, mutated target cells may give rise to other mutations when subjected to the same treatment or a different treatment. A different treatment may be the same type of treatment (e.g., chemotherapy, radiation therapy or antibiotics) with a different dosage of the therapeutic agent or a different type of treatment). In other words, treatments may give rise to generations of mutations. For example, a TP-53 type target cell of lung cancer may mutate to KSR type target cell when subjected to one treatment. The KSR type target cell may mutate to another type off target cell of lung cancer when subjected to the same or another treatment. To that end, the VOC emission data of target cells cultures, which are known to develop treatment resistant mutation or mutations, are acquired before and after been subjected to a treatment known to trigger development of treatment resistant mutation or mutations. The cultures before treatment and after treatment are the same cultures. The VOC emission data of target cells cultures that developed one or more treatment resistant mutations (verified by gene sequencing) are compared with the VOC emission data of the cultures prior to applying the treatment. This process may be repeated several times for the same treatment and/or several times for different treatments. A complex treatment resistant target cells VOC profile is produced which includes the target cells VOC profiles of all or selected ones of the mutation generations. The term 'type' of target cells herein relates to target cells, which may or may not have mutated from other target cells or to target cells which have or have not been previously treated. Reference is now made to FIGS. 7A and 7B, which are a schematic illustration of a method for determining a VOC profile of target cells, which developed treatment resistant mutations from a selected treatment, operative in accordance with a further embodiment of the disclosed technique.

In procedure 400, a cells culture, respective of target cells of a selected type, known to develop treatment resisting mutation, is produced. After procedure 400, the method proceeds to procedure 402.

In procedure 402, VOC emission data, relating to the VOC emitted by the target cells in the target cells cultures is acquired before administering treatment. With reference to FIG. 1, analysis device 102 acquires VOC emission data relating to the VOC emitted by the target cells before being treated from the target cells cultures. After procedure 402 the method proceeds to procedure 404 and to procedure 414.

In procedure 404, a treatment, which is known to produce treatment resistant mutation or mutations, is applied to the target cells cultures. After procedure 404, the method proceeds to procedure 406.

In procedure 406, Identifying in the treated target cells cultures, target cells that developed treatment resistance, for example by employing microscopical scan. After procedure 406, the method proceeds to procedure 408.

In procedure 408, a respective mutated target cells culture is produced for each identified treatment resistant mutated target cell (i.e., after applying the selected treatment). In other words, new cultures of these treatment resistant mutated target cells are created separately, such that the selected treatment can be applied thereto in order to identify additional treatment resistant mutations. After procedure 408, the method proceeds to procedure 410.

In procedure 410, the target cells identified to developed treatment resistant mutations are genetically sequenced to determine the mutation or mutations (i.e., if existed) and to identify the molecular classification of the post treatment target cells. After procedure 410, the method proceeds to procedure 412.

In procedure 412, VOC emission data relating to the mutated target cells is acquired from the respective muted target cells culture. With reference to FIG. 1, analysis device 102 acquires VOC emission data from the mutated target cells cultures. After procedure 412, the method proceeds to procedure 414.

In procedure 414, producing a treatment resisting target cells VOC profile is produced by comparing the pre-treatment target cells cultures VOC emission data (i.e., of the target cells cultures before the treatment), with the mutated target cells cultures VOC emission data of the mutated cells cultures. With reference to FIG. 1, processor 106 produces a treatment resistant VOC profile by comparing the VOC emission data of the target cells cultures before any treatment with the target cells cultures VOC emission data of the mutated target cells cultures. After procedure 414, the method proceeds to procedure 416.

In procedure 416, a complex treatment resistant VOC profile is determined. A complex treatment resistant VOC profile includes information from the treatment resisting target cells VOC profiles of a selected number of generations of mutations. With reference to FIG. 1, processor 106 determines the complex treatment resistant VOC profile. After procedure 416, the method proceeds to procedure 418.

In procedure 418, a predicted complex treatment resistant VOC profile is determined by predicting the VOC concentration levels in the breath and body fluids from the complex treatment resistant VOC profile. The VOC concentration levels are predicted by using a diffusion model such as the Farhi equation or a modified Farhi's model, both further elaborated below. With reference to FIG. 1, processor 106 determines a predicted complex treatment resistant VOC profile. After procedure 418, the method proceeds to procedure 420.

In procedure 420, the predicted treatment resistant VOC profiles are stored in a database. With reference to FIG. 1, processor 106 stores the predicted treatment resistant VOC profiles in database 104.

It is noted that the method described in FIGS. 7A and 7B may be repeated for a selected number of treatments or mutations or both. The complex a complex treatment resistant VOC profile incorporates the information from each of these repetitions. The above stored treatment resistant VOC profiles may be employed to identify a personal treatment resistant VOC profile of an individual.

Determining VOC Profiles for an Individual

Similar to determining VOC profiles for general populations, VOC profiles may be determined for individuals. As mentioned above, according to the disclosed technique, the VOC emissions from the body of a patient or patients can be associated, for example, with a corresponding cancer type, which results from cell gene mutation or mutations. Following are examples of associating VOC emission from a body of an individual patient, with a corresponding cancer type, which results from a cell gene mutation. Nevertheless, the techniques may be applied to any form and type of cells.

Figure 8A:
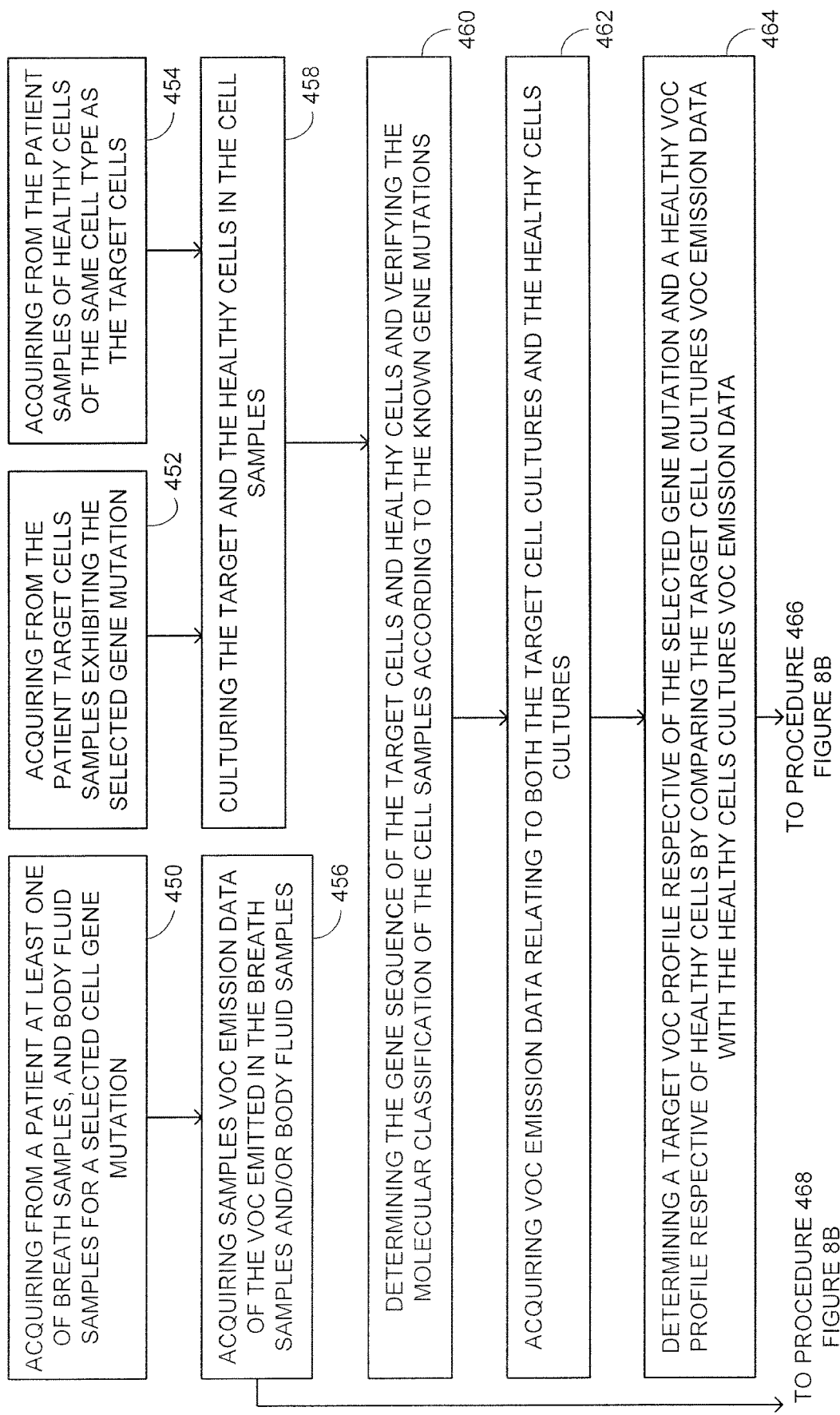
FIGS. 8A and 8B are a schematic illustration of an exemplary method for associating VOC emissions with a corresponding abnormal or pathological cells in an individual patient, operative in accordance with another embodiment of the disclosed technique.
Figure 8B:
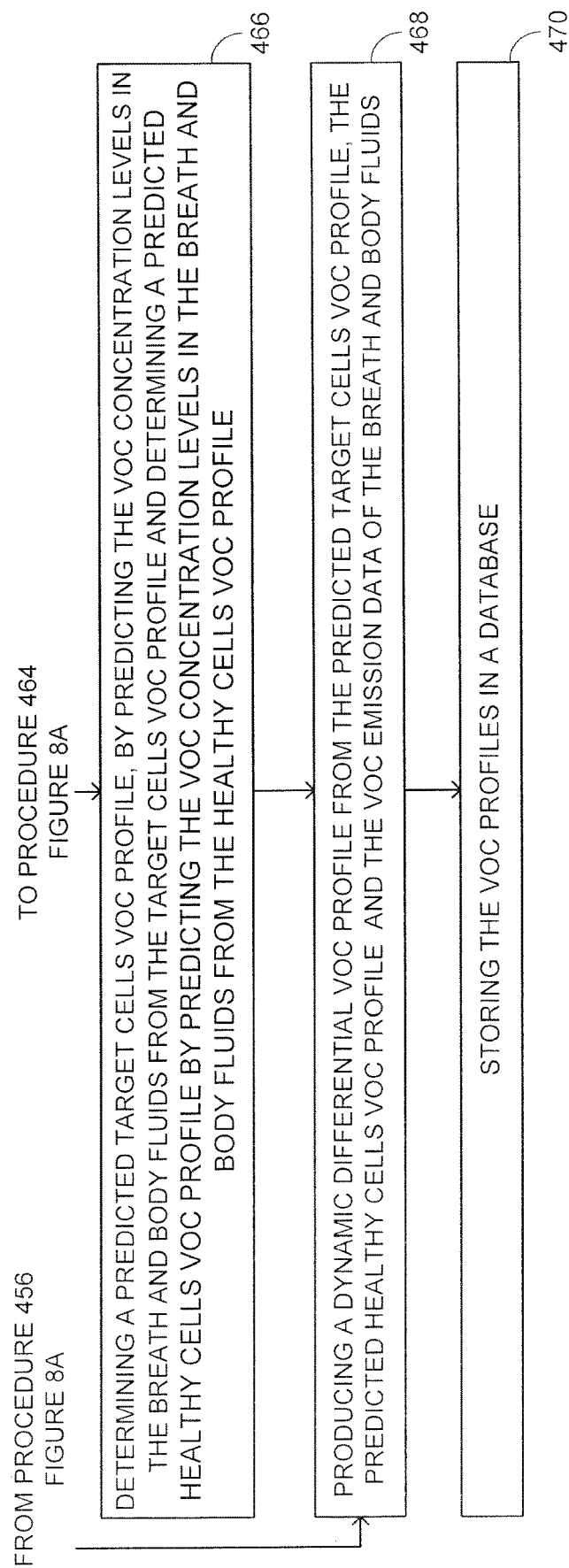

Reference is now made to FIGS. 8A and 8B, which are a schematic illustration of an exemplary method for associating VOC emissions with a corresponding abnormal or pathological cells in an individual patient, operative in accordance with another embodiment of the disclosed technique. In FIGS. 8A and 8B, the exemplary pathological cells are a form of cancer type.

In procedure 450, at least one of breath and body fluid (e.g., blood, urine or sweat) samples are acquired from the patient for a selected cell gene mutation. The cell gene mutation may be associated with a cancer type. The term 'cancer type' relates to the type of cancer (e.g., ovarian, breast, bladder, skin, colon, etc.) as well as to the genetic subtype of the cancer (e.g., $HER2_+$, HER triple negative, etc.). The cancer type and the genetic mutation causing this cancer is known before the samples are acquired. The acquired breath and body fluid sample are associated with that cancer type. After procedure 450, the method proceeds to procedure 456.

In procedure 452, target cells samples exhibiting the selected gene mutation are acquired from the patient. In the example brought forth in FIGS. 8A and 8B, the target cells are carcinogenic cells of a respective cancer type exhibiting a respective gene mutation. These target cells are acquired, for example, by a biopsy procedure. After procedure 452, the method proceeds to procedure 458.

In procedure 454, samples of healthy cells of the same type as the target cells are acquired from the patient. These healthy cells may also be acquired, for example, by a biopsy procedure. After procedure 454, the method proceeds to procedure 458.

In procedure 456, VOC emission data of the at least one of breath and body fluid samples is acquired. With reference to FIG. 1, analysis device 102 acquires emission data of at least one of the breath and body fluids. After procedure 456, the method proceeds to procedure 468.

In procedure 458, the target and the healthy cells in the cell samples are cultured. After procedure 458, the method proceeds to procedure 460.

In procedure 460, the gene sequence of the cultured target cells and healthy cells is determined. Then, the molecular classification of the cell samples is verified according to the known gene mutations. Since in general, the classification of the genetic mutation of the target cells of the patient is known before the target cells are sampled, this classification needs only to be verified. For example, there are currently over 315 related mutations. This procedure is also referred to as molecular classification. After procedure 460, the method proceeds to procedure 462.

In procedure 462, VOC emission data, relating to both target cells and healthy cells is acquired. With reference to FIG. 1, analysis device 102 acquires emission data relating to both target and healthy cells. After procedure 462, the method proceeds to procedure 464.

In procedure 464, a target cells VOC profile respective of the selected gene mutation (and thus with the respective cancer type), and a healthy cells VOC profile respective of healthy cells are determined by comparing the target cells cultures VOC emission data is compared with the healthy cells cultures VOC emission data. With reference to FIG. 1, processor 106 produces a target cells VOC profile and a healthy cells VOC profile by comparing the target cells cultures VOC emission data with the healthy cells cultures VOC emission data to. After procedure 464, the method proceeds to procedure 466.

In procedure 466, a predicted target cells VOC profile is determined by predicting the VOC concentration levels in the breath and body fluids from the target cells VOC profile and a predicted healthy cells VOC profile is determined by predicting the VOC concentration levels in the breath and body fluids from the healthy cells VOC profile. The VOC concentration levels are predicted by using a diffusion model such as the Farhi equation or a modified Farhi's model, both further elaborated below. Since the target cells VOC profile is associated with the selected gene mutation, the predicted target cells VOC profile is also associated with that same gene mutation. With reference to FIG. 1, processor 106 determines the predicted target cells VOC profile and the predicted healthy cells VOC profile from the target cells VOC profile and the healthy cells VOC profile. After procedure 466, the method proceeds to procedure 468.

In procedure 468, a Dynamic Differential VOC profile is produced from the predicted target cells VOC profile, the predicted healthy cells VOC profile and the VOC emission data of the breath and body fluids. This Dynamic Differential VOC profile is produced by minimizing the error between the predicted target cells VOC profile and the VOC emission data of the breath and body fluid samples. Since the predicted target cells VOC profile is associated with corresponding gene mutations, the Dynamic Differential VOC profile is also associated with that gene mutation. With reference to FIG. 1, processor 106 determines a Dynamic Differential VOC profile. After procedure 468, the method proceeds to procedure 470.

In procedure 470, the Dynamic Differential VOC profiles are stored in a database. With reference to FIG. 1, processor 106 stores the VOC profiles in database 104.

Figure 9A:
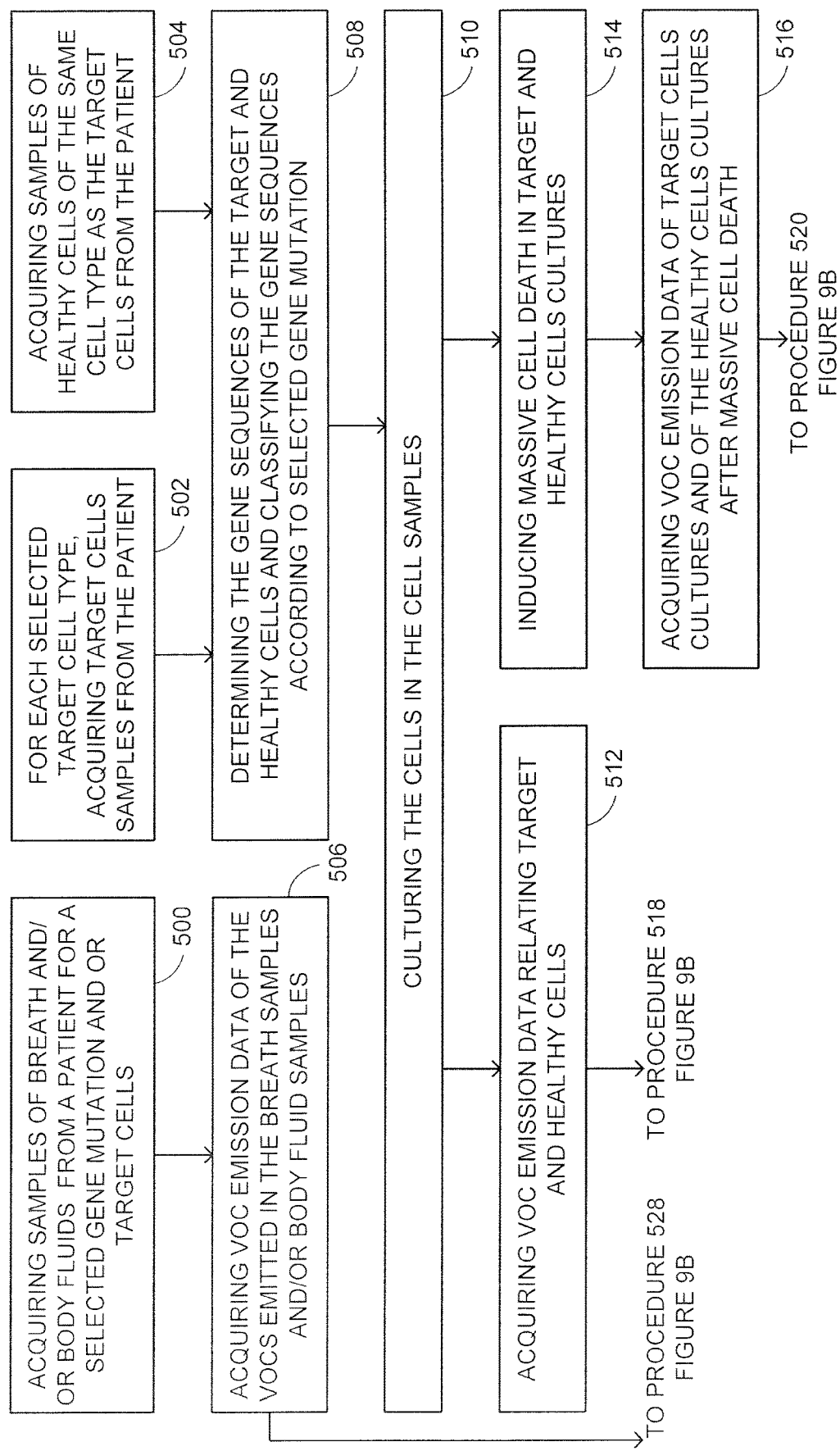
FIGS. 9A and 9B are schematic illustrations of a method for associating VOC emissions with corresponding target cells (e.g., carcinogenic cells), before and after MCD, in an individual patient, operative in accordance with a further embodiment of the disclosed technique.
Figure 9B:
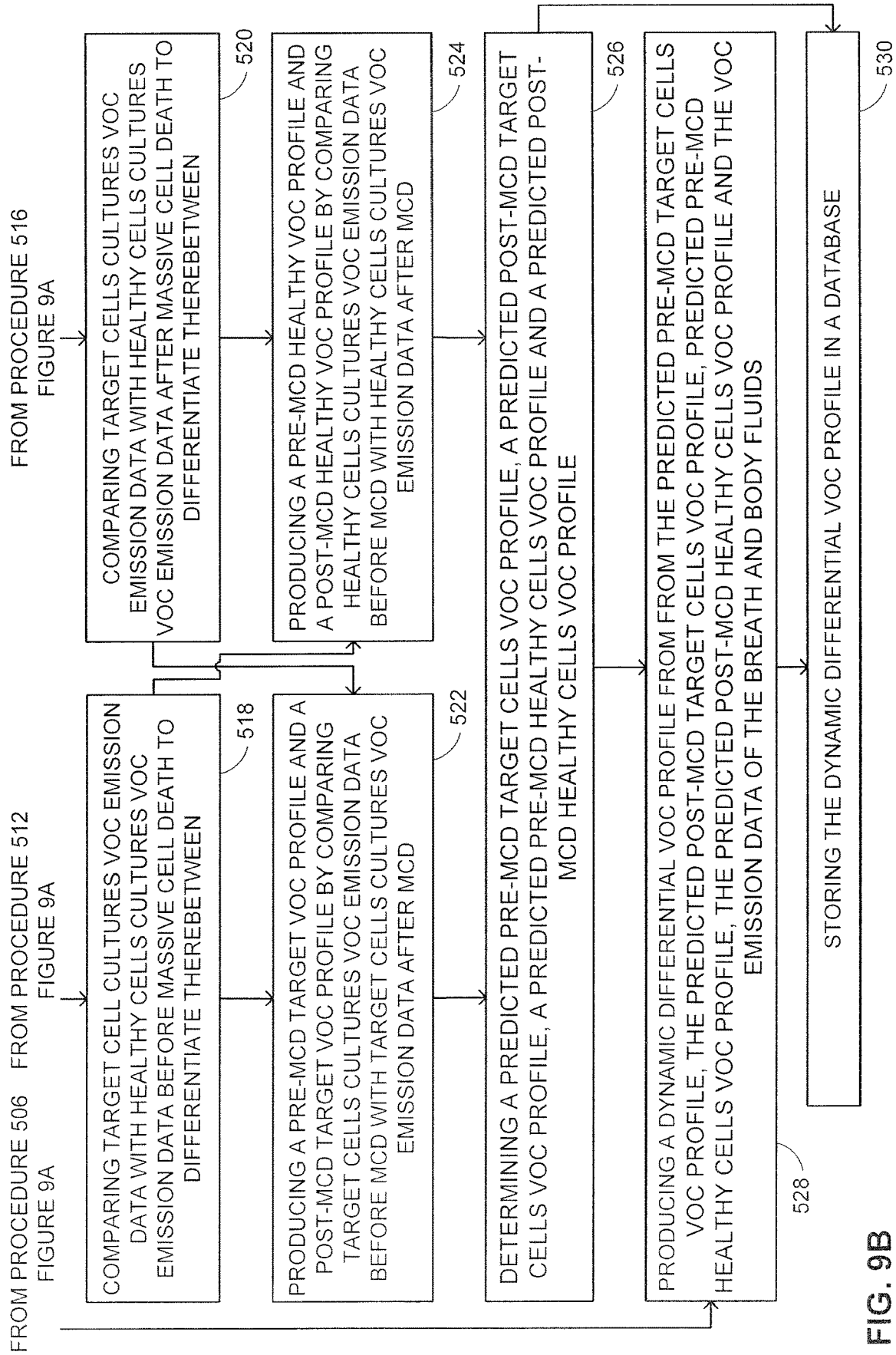

VOC profiles may be employed to determine treatment efficacy in an individual patient. However, to determine treatment efficacy, the influence of the treatment (e.g., chemotherapy, radiation therapy) which induces Massive Cell Death (MCD), on the VOCs emitted by the patient, needs to be determined. This influence is determined by inducing MCD in a cells cultures in such a way that does not generate VOC artifacts (e.g., by employing flash freeze techniques or UV light techniques) and associating between VOC emissions with corresponding target cells in an individual patient, before and after MCD. Reference is now made to FIGS. 9A and 9B, which are schematic illustrations of a method for associating VOC emissions with corresponding target cells (e.g., carcinogenic cells), before and after MCD, in an individual patient, operative in accordance with a further embodiment of the disclosed technique.

In procedure 500, at least one of breath and body fluid (e.g., blood, urine or sweat) samples are acquired from the patient for a selected target cell and/or cell gene mutation. Similar to as described above, the target cell-type and the genetic mutation causing a pathologic condition are known before the samples are acquired. The acquired breath and body fluid sample are associated with that target cell type. After procedure 500, the method proceeds to procedure 506.

In procedure 502, for each selected target cell type, target cells samples are acquired from the patient. The target cells types may be target cells exhibiting a selected gene mutation or causing a pathologic condition. In the example brought forth in FIGS. 9A and 9B, the target cells are carcinogenic cells of a respective cancer type exhibiting a respective gene mutation. Nevertheless, the method described in FIGS. 9A & 9B can be applied to any target cells. These target cells are acquired, for example, by a biopsy procedure. After procedure 502, the method proceeds to procedure 508.

In procedure 504, samples of healthy cells of the same type of the target cells are acquired from the patient. These healthy cells may also be acquired, for example, by a biopsy procedure. After procedure 504, the method proceeds to procedure 508.

In procedure 506, VOC emission data of the at least one of breath and body fluid samples is acquired. With reference to FIG. 1, analysis device 102 acquires emission data of at least one of the breath and body fluids. After procedure 506, the method proceeds to procedure 528.

In procedure 508, the gene sequence of the target cells and healthy cells is determined. Then, the gene sequence is classified according to the known carcinogenic gene mutations of the selected cancer type. This procedure is also referred to as molecular classification. After procedure 508, the method proceeds to procedure 510.

In procedure 510, the target and the healthy cells in the cell samples are cultured. After procedure 510, the method proceeds to procedure 512 and 514.

In procedure 512, VOC emission data, relating to both healthy cells and target cells is acquired. With reference to FIG. 1, analysis device 102 acquires emission data relating to both healthy and target cells. After procedure 512, the method proceeds to procedure 518.

In procedure 514, MCD is induced in the target and healthy cells cultures. Preferably the MCD is induced in a manner that does not generate VOC artifacts (e.g., by employing flash freeze techniques or UV light techniques). It should be noted that the MCD is induced in the same target cells cultures and healthy cells cultures that were used to acquire the pre-MCD VOC emission data. After procedure 514, the method proceeds to procedure 516.

In procedure 516, VOC emission data relating to the target cells cultures and VOC emission data relating to the healthy cells cultures, are acquired after MCD was induced in target cells and healthy cells cultures. With reference to FIG. 1, analysis device 102 acquires VOC emission data from both target cells cultures and healthy cells cultures after MCD After procedure 516, the method proceeds to procedure 520.

In procedure 518, target cells cultures VOC emission data is compared with healthy cells cultures VOC emission data before MCD, to differentiate therebetween. With reference to FIG. 1, processor 106 compares the VOC emission data of target cells cultures with the VOC emission data of healthy cells cultures before MCD to differentiate therebetween. After procedure 518, the method proceeds to procedure 522 and 524.

In procedure 520, target cell cultures VOC emission data is compared with healthy cells cultures VOC emission data after MCD to differentiate therebetween. With reference to FIG. 1, processor 106 compares the VOC emission data of target cells cultures with the VOC emission data of healthy cells cultures after MCD to differentiate therebetween. After procedure 520, the method proceeds to procedure 522 and 524.

In procedure 522, producing a pre-MCD target cells VOC profile and a post-MCD target cells VOC profile, by comparing the target cell cultures VOC emission data before MCD, with target cell cultures VOC emission data after MCD. With reference to FIG. 1, processor 106 produces a pre-MCD target cells VOC profile and a post-MCD target cells VOC profile by comparing target cell cultures VOC emission data before MCD with target cell cultures VOC emission data after MCD. After procedure 522, the method proceeds to procedure 526.

In procedure 524 producing a pre-MCD healthy cells VOC profile and a post-MCD healthy cells VOC profile by comparing healthy cell cultures VOC emission data before MCD, with healthy cell cultures VOC emission data after MCD. With reference to FIG. 1, processor 106 produces a pre-MCD healthy cells VOC profile and a post-MCD healthy cells VOC profile by comparing the healthy cell cultures VOC emission data before MCD with healthy cell cultures VOC emission data after MCD. After procedure 524, the method proceeds to procedure 526.

In procedure 526, a predicted pre-MCD target cells VOC profile, a predicted post-MCD target cells VOC profile, a predicted pre-MCD healthy cells VOC profile and a predicted post-MCD healthy cells VOC profile are determined. The predicted pre-MCD target cells VOC profile and the predicted post-MCD target cells VOC profile are determined by predicting the VOC concentration levels in the breath and body fluids from the pre-MCD target cells VOC profile and the post-MCD target cells VOC profile. The predicted pre-MCD healthy cells VOC profile and the predicted post-MCD healthy cells VOC profile are determined by predicting the VOC concentration levels in the breath and body fluids from the pre-MCD healthy cells VOC profile and the post-MCD healthy cells VOC profile. The VOC concentration levels are predicted by using a diffusion model such as the Farhi equation f or a modified Farhi's model, both further elaborated below. Since the pre-MCD target cells VOC profile and the post-MCD are associated with the selected gene mutation, the predicted pre-MCD target cells VOC profile and the predicted post-MCD target cells VOC profile are also associated with that same gene mutation. With reference to FIG. 1, processor 106 determines the predicted VOC concentration levels in the breath and body fluids from the pre-MCD target cells VOC profile, post-MCD target cells VOC profile, pre-MCD healthy cells VOC profile and post-MCD healthy cells VOC profile. From procedure 526, the method proceeds to procedure—528.

In procedure 528, a Dynamic Differential VOC profile is produced from the predicted pre-MCD target cells VOC profile, the predicted post-MCD target cells VOC profile, predicted pre-MCD healthy cells VOC profile, the predicted post-MCD healthy cells VOC profile and the VOC emission data of the breath and body fluids. This Dynamic Differential VOC profile is produced by minimizing the error between the predicted pre-MCD target cells VOC profile, post-MCD target cells VOC profile and the VOC emission data of the breath and body fluid samples. Since the predicted pre-MCD target cells VOC profile and post-MCD target cells VOC profile are associated with corresponding gene mutations, the Dynamic Differential VOC profile is also associated with those gene mutations. With reference to FIG. 1, processor 106 determines a Dynamic Differential VOC profile. After procedure 528, the method proceeds to procedure 530.

In procedure 530, the Dynamic Differential VOC profiles are stored in a database. With reference to FIG. 1, processor 106 stores the Dynamic Differential VOC profile in database 104.

Figure 10A:
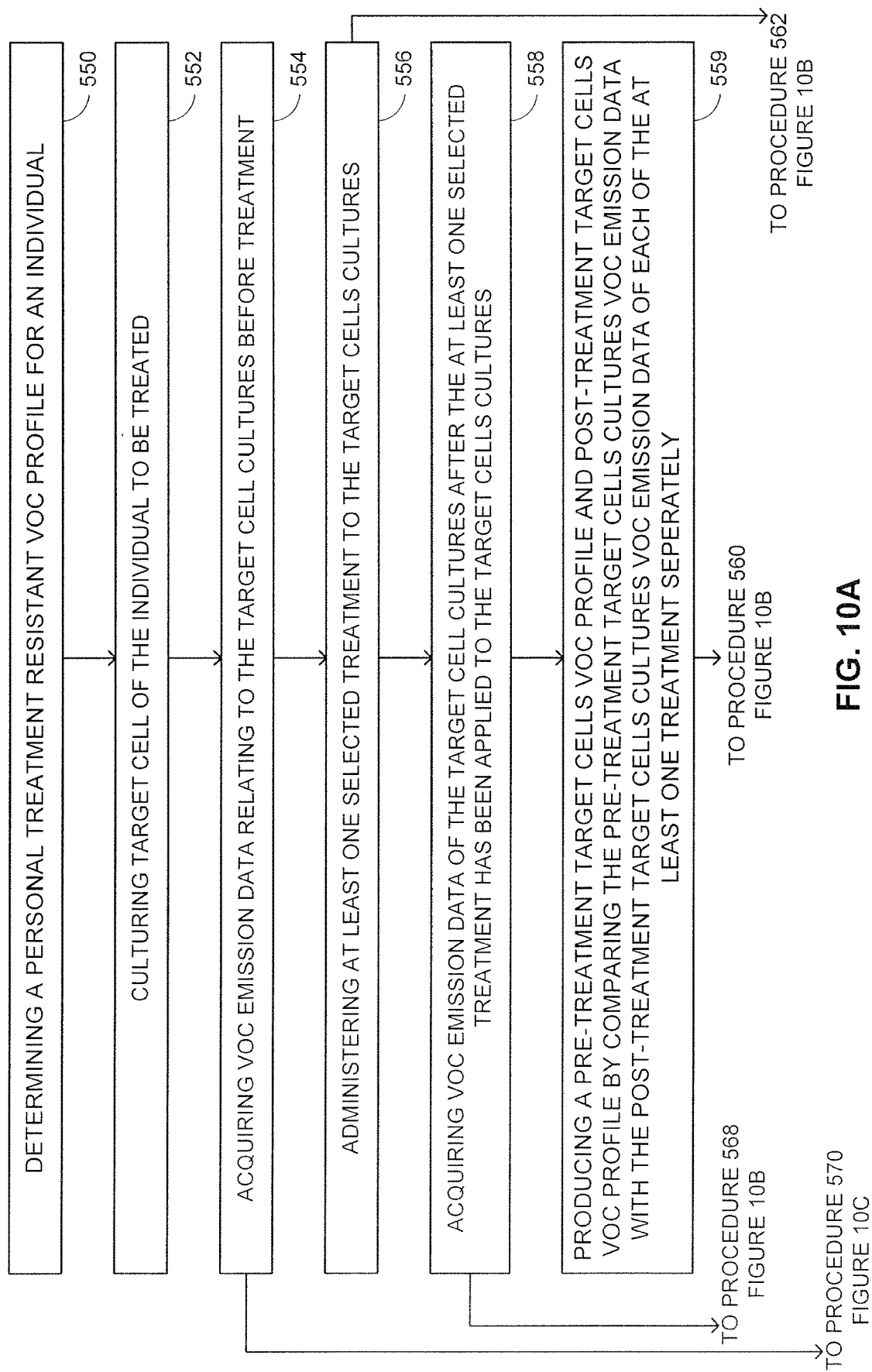
Figure 10C:
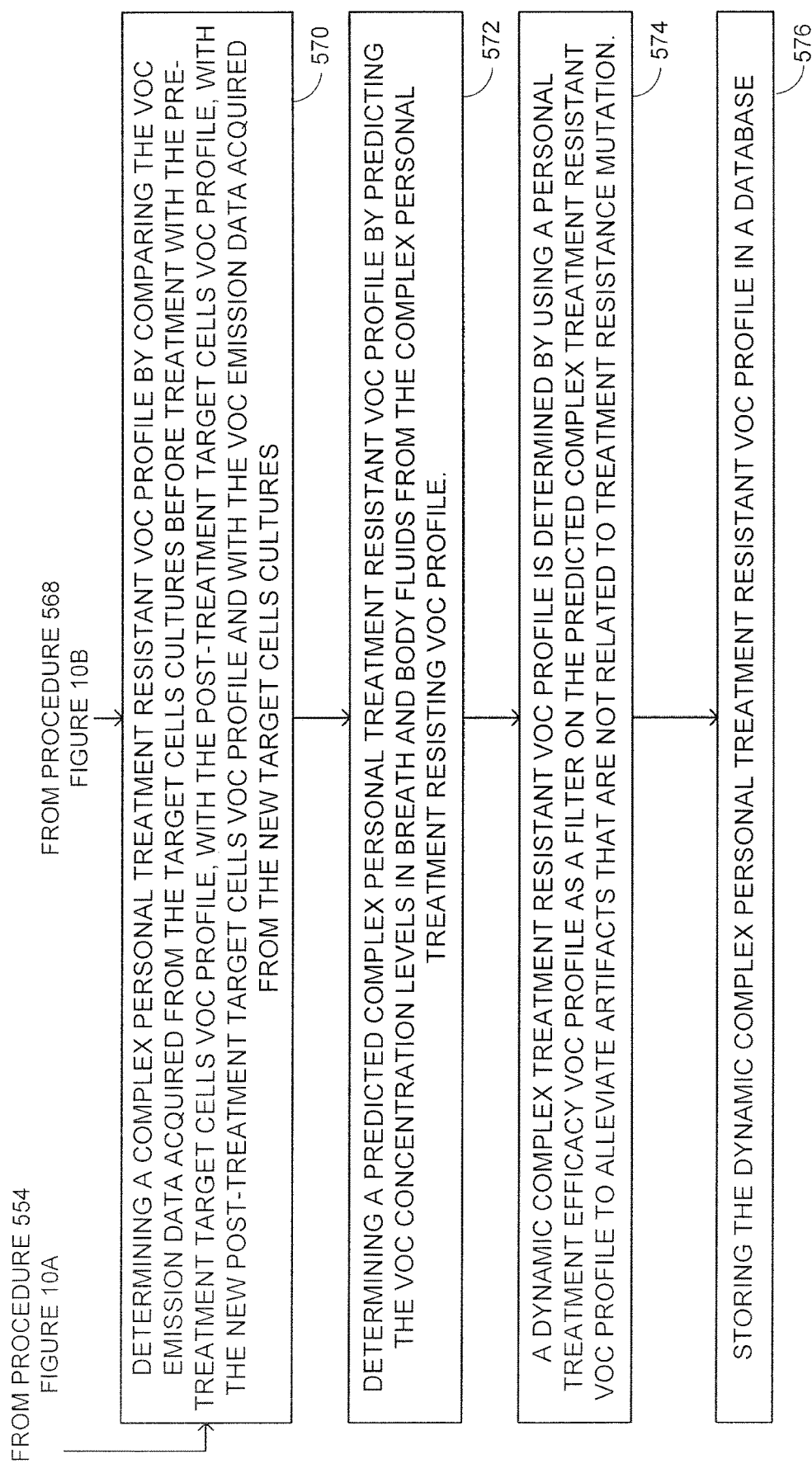

Reference is now made to FIGS. 10A, 10B and 10C, which are a schematic illustration of a method for identifying a personal treatment resistant VOC profile of an individual for a selected treatment, operative in accordance with another embodiment of the disclosed technique. In procedure 550, a personal treatment resistant VOC profile is determined for an individual, for example, according to the method described herein below in conjunction with FIGS. 13A, 13B, 13C, 13D and 13E herein below. After procedure 550, the method proceeds to procedure 552.

In procedure 552, target cells of the individual to be treated, are cultured. After procedure 552, the method proceeds to procedure 554.

In procedure 554, VOC emission data relating to the target cells cultures is acquired before treatment. With reference to FIG. 1, analysis device 102 acquires VOC emission data relating to the target cells cultures before treatment. After procedure 554 the method proceeds to procedure 556 and procedure 570.

In procedure 556, at least one selected treatment is administered to the target cells cultures. When the selected treatment or treatments include more than one drug and/or therapy, these selected treatments are applied separately and conjointly to different sets of the respective target cells cultures. After procedure 556 the method proceeds to procedure 558 and to procedure 562.

In procedure 558, VOC emission data of the target cells cultures is acquired after at least one selected treatment has been applied to the target cells cultures. With reference to FIG. 1 analysis device 102, acquires VOC emission data of the target cells cultures after at least one selected treatment. After procedure 558 the method proceeds to procedure 559 and to procedure 568.

In procedure 559, producing a pre-treatment target cells VOC profile and post-treatment target cells VOC profile by comparing the pre-treatment target cells cultures VOC emission data with the post-treatment target cells cultures VOC emission data of each of the at least one treatment separately. With reference to FIG. 1, processor 106 producing pre-treatment target cells VOC profile and post-treatment target cells VOC profile by comparing the pre-treatment target cells cultures VOC emission data with the post-treatment target cells cultures VOC emission data. After procedure 559 the method proceeds to procedure 560.

In procedure 560, identifying treatment resistant mutations by comparing the pre-treatment target cells VOC profile and the post-treatment target cells VOC profile are compared with stored predicted complex treatment resistant VOC profiles (e.g., profiles such as those determined in accordance with the method described hereinabove in conjunction with FIGS. 7A and 7B). With reference to FIG. 1, process 106 compares the pre-treatment target cells VOC profile and the post-treatment target cells VOC profile with stored predicted complex treatment resistant VOC profiles in order to identify treatment resistant mutations. After procedure 560 the method proceeds to procedure 562.

In procedure 562, target cells that were identified to produce treatment resistant mutation, with a corresponding post-treatment target cells VOC profile and that does not appear in the stored predicted complex treatment resistant VOC profiles, are cultured separately to produce new target cells cultures. After procedure 562, the method proceeds to procedure 566.

In procedure 564, the separately cultured target cells, that exhibit treatment resistant mutation (i.e., that were identified in the cultures but were not identified when there post-treatment target cells VOC profile was compared with the stored predicted complex treatment resistant VOC profile), are gene sequenced and undergo molecular identification in order to identify and classify the treatment resistant mutation. After procedure 564, the method proceeds to procedure 566.

In procedure 566, VOC emission data of the new target cells cultures is acquired. With reference to FIG. 1, analysis device 102 acquires VOC emission data of the new target cells cultures. After procedure 566, the method proceeds to procedure 568.

In procedure 568, a new post-treatment target cells VOC profile is determined by comparing the pre-treatment target cells cultures VOC emission data with the new post-treatment target cells cultures VOC emission data. With reference to FIG. 1, processor 106 determines a new post-treatment target cells VOC profile is determined by comparing the pre-treatment target cells cultures VOC emission data with the new post-treatment target cells cultures VOC emission data. After procedure 568 the method proceeds to procedure 570.

In procedure 570, a complex personal treatment resistant VOC profile is determined by comparing the VOC emission data acquired from the target cells cultures before treatment with the pre-treatment target cells VOC profile with the post-treatment target cells VOC profile (i.e., relating to treatment resistant mutation identified using the stored predicted complex treatment resistant VOC profiles), with the new post-treatment target cells VOC profile (i.e., relating to mutation identified using gene sequencing and molecular identification) and with the VOC emission data acquired from the new target cells cultures (i.e., relating to the target cells that developed treatment resistance). With reference to FIG. 1, processor 106 determines a complex personal treatment resistant VOC profile by comparing the VOC emission data acquired from the target cells cultures before treatment with the pre-treatment target cells VOC profile, with the post-treatment target cells VOC profile, with the new post-treatment target cells VOC profile and with the VOC emission data acquired from the new target cells cultures. After procedure 570, the method proceeds to procedure 572.

In procedure 572, a predicted complex personal treatment resistant VOC profile is determined by predicting the VOC concentration levels in breath and body fluids from the complex personal treatment resistant VOC profile. The VOC concentration levels are predicted by using a diffusion model such as the Farhi equation or a modified Farhi's model, both further elaborated below. With reference to FIG. 1, process 106 determines the predicted complex personal treatment resistant profile. After procedure 572, the method proceeds to procedure 574.

In procedure 574, a dynamic complex treatment resistant VOC profile is determined by using the personal treatment efficacy VOC profile as a filter on the predicted complex treatment resistant VOC profile to alleviate artifacts that are not related to treatment resistance mutation. With reference to FIG. 1, process 106 employs a stored personal treatment efficacy to alleviate artifacts that are not related to treatment resistance mutation on a predicted complex treatment resistant VOC profile and determines a dynamic complex treatment resistant VOC profile. After procedure 574, the method proceeds to procedure 576.

In procedure 576, the dynamic complex personal treatment resistant VOC profile is stored in a database. With reference to FIG. 1, processor 106 stores the dynamic complex personal treatment resistant VOC profile in database 104.

Uses of Stored VOC Profiles

One use for VOC profiles is to determine if a person is carrying a carcinogenic genetic mutation and to further identify which carcinogenic genetic mutation is active in a person. To that end, VOC emission data of breath and/or body fluids is sampled from the person. This VOC emission data is then compared with stored Dynamic Differential VOC profiles (e.g., Dynamic Differential VOC profiles determined according to the method described in conjunction with FIGS. 3A, 3B and 3C). As mentioned above each of these stored Dynamic Differential VOC profiles is associated with a respective genetic mutation. When a match between the VOC emission data and at least one stored Dynamic Differential VOC profile is detected, that patient is identified as carrying a carcinogenic genetic mutation. Furthermore, the gene mutation associated with the Dynamic Differential VOC profile that best matches the acquired VOC emission data is identified as the active gene mutation.

The VOC profiles stored in the database may be employed to determine the efficacy of a treatment administered to a patient. Thus, even during a prolonged treatment which may include a plurality of phases (e.g., chemotherapy, radiation therapy, medication), the efficacy of the treatment may be determined by acquiring VOC emission data from the patient's breath and/or body fluids before the treatment and establishing which of the Dynamic Differential or predicted VOC profiles stored in the database corresponds with the acquired VOC emission data. VOC emission data of the breath and/or body fluids is also acquired after at least one selected phase of the selected treatment (i.e., between at least one of the treatment phases or at the end of the treatment or any combination thereof). The VOC emission data acquired after at least one selected phase of the selected treatment is also compared with both the stored Dynamic Differential or predicted VOC profiles and the VOC emission data acquired prior to the treatment to ascertain the efficacy of the administered treatment. In cases where VOC emission data is acquired for more than one phase of treatment, they are compared with each other, the VOC emission data prior to the treatment, and the stored Dynamic Differential or predicted VOC profiles. In cases were a treatment of a patient has already started, the efficacy of the treatment can be determined by acquiring VOC emission data of the patient's breath and/or body fluids before and after a selected phase of the treatment. The VOC emission data acquired before the selected phase of the treatment is compared with the VOC emission data acquired after the selected phase of the treatment, and the stored Dynamic Differential or predicted VOC profile to determine treatment efficacy.

Furthermore, as mentioned above, MCD is employed when determining VOC profiles. As shall be further elaborated below, employing MCD in a manner that does not generate VOC artifacts is also employed in determining treatment efficacy. In general, the VOCs emitted by target cells before and after a treatment or after a phase of a treatment may differ from patient to patient, from one condition to another, as well as from the time at which the VOCs where acquired. For example, VOCs and the concentration levels thereof acquired during a menstruating woman, shall be different from the VOCs and concentration levels thereof acquired when that woman is not menstruating. As a further example, a patient may be afflicted with another medical condition (i.e., other than the one being treated). As such, the VOCs emitted by the target cells of such a patient, as well as the concentration levels of these VOCs, may be different from a patient which is not afflicted by another medical condition.

Since VOCs emitted by target cells before and after a treatment or after a phase of a treatment may differ from patient to patient, from one condition to another, as well as from the time at which the VOCs where acquired, it is beneficial to obtain information relating to the expected VOCs emissions (i.e., which VOCs are emitted and what are the concentrations thereof) after a treatment or a phase of an administered treatment. When cells die, their membrane disintegrates. When the membrane disintegrates, VOCs that were "trapped" within the cell are released. Therefore, when a target cell has been treated and died, the concentration levels of the VOCs that were "trapped" within the cell expected to rise. Inducing MCD in a manner that does not generate VOC artifacts on target cells destroys these target cells. Measuring the concentrations levels of the VOCs emitted by these destroyed cells provides the expected results of the treatment for the specific patient, with the respective genome and medical condition at the time of the treatment. An optimal treatment is expected to destroy all the target cells in a patient. Thus, the concentration values of VOCs associated with MCD (i.e., the VOCs that were "trapped" within the cells) rise when the treatment is effective. As such, comparing the VOCs concentration values of the VOCs obtained from target cells after treatment or after a phase of the treatment, with the VOC concentration values of the VOCs obtained after MCD was induced, provides an indication if the treatment achieved the expected results. As an additional indication of the efficacy of the treatment, the concentration values of VOCs associated with target cells decrease when a treatment is effective. Furthermore, the concentration values of VOCs associated with healthy cells remains unchanged when a treatment is effective. A treatment is further effective when no treatment resistance or mutation potential is determined as further elaborated below.

Figure 11:
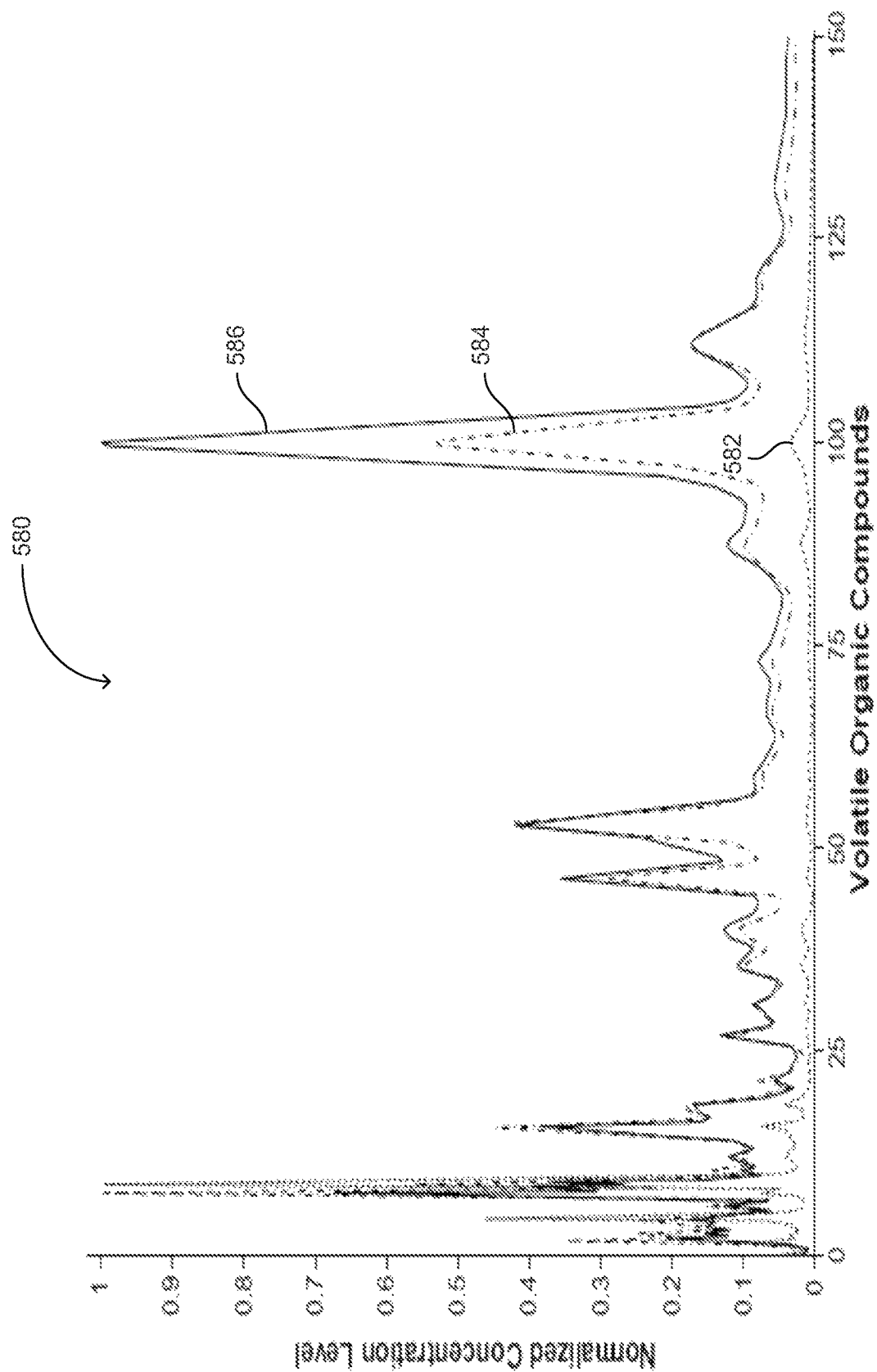
FIG. 11 is a schematic illustration of a graph of exemplary three VOC emission data associated with breast cancer of a specific patient, in accordance with a further embodiment of the disclosed technique.

Reference is now made to FIG. 11, which is a schematic illustration of a graph, generally referenced 580, of exemplary three VOC emission data 582, 584 and 586, associated with breast cancer of a specific patient, in accordance with a further embodiment of the disclosed technique. In the example brought forth in FIG. 11, the VOC emission data 582, 584 and 586 relate to a specific patient with breast cancer. VOC emission data 582 depicts VOC emissions of selected VOCs of healthy cells after MCD (i.e., either directly to the patient or to a culture—as further explained below). VOC emission data 584 depicts VOC emissions, of selected VOCs of target cells before MCD, and VOC emission data 586 depicts VOC emissions, of selected VOCs of target cells after MCD. As seen in FIG. 11, VOC designated 100 exhibits a greater concentration value in VOC emission data 586 (i.e., after MCD) than the concentration values in VOC emission data 584 (i.e., before MCD). Specifically, in the exemplary case depicted in FIG. 11, VOC designated 100 is 3-methylhexane. Accordingly, an optimal treatment in case of breast cancer of the specific patient to which graph 580 relates would show an increase in the concentration values of 3-methylhexane as well as other VOCs as depicted in FIG. 11. Other VOCs measured in FIG. 11 are, for example, 2-ethylhexanol, 5-ethyl-3-methyloctane, acetone, ethanol, ethyl acetate, ethylbenzene, isononane, isoprene, nonanal, styrene, toluene and undecane.

Figure 12:
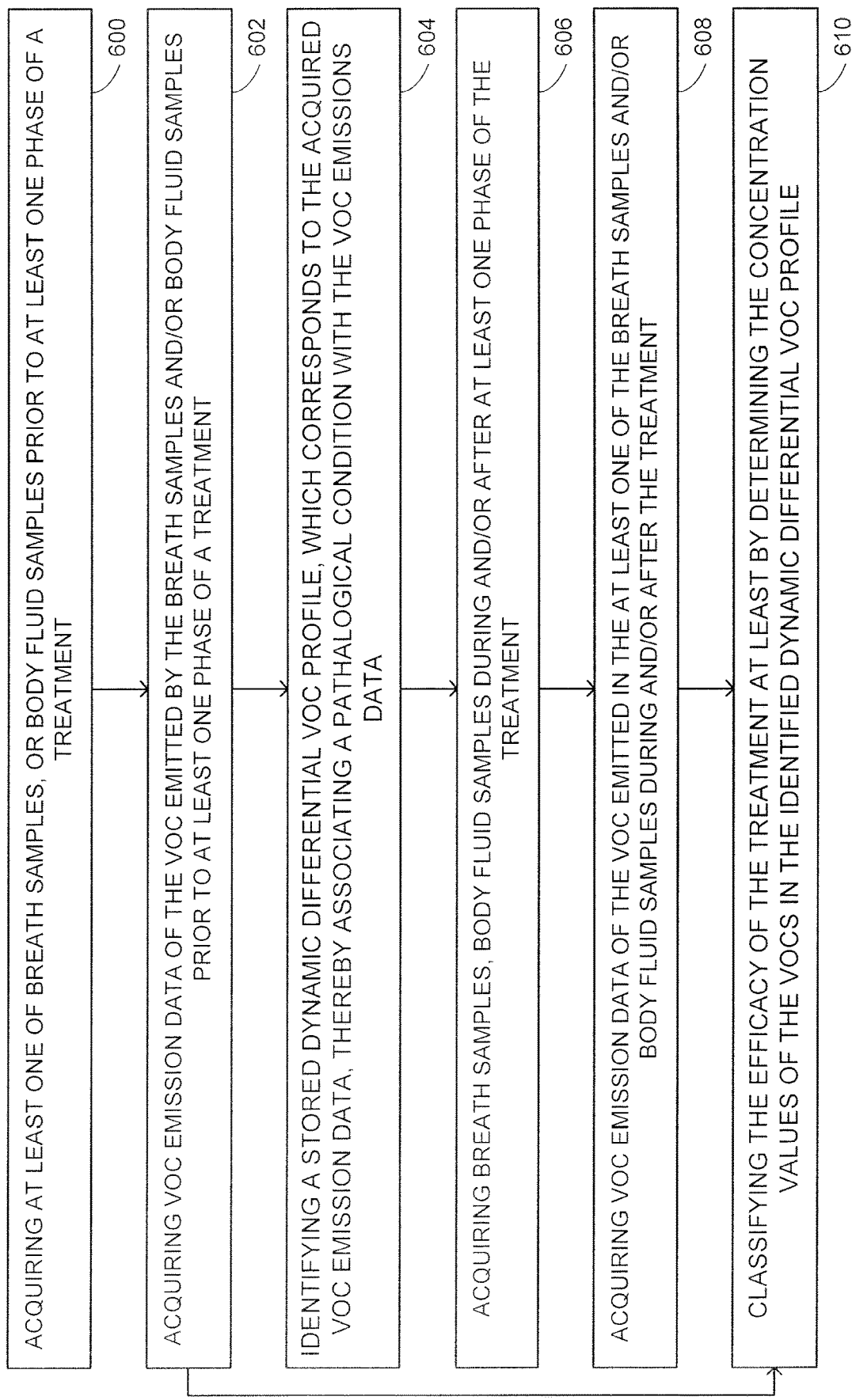
FIG. 12 is a schematic illustration of a method for determining treatment efficacy, operative in accordance with a further embodiment of the disclosed technique.
Figure 13A:
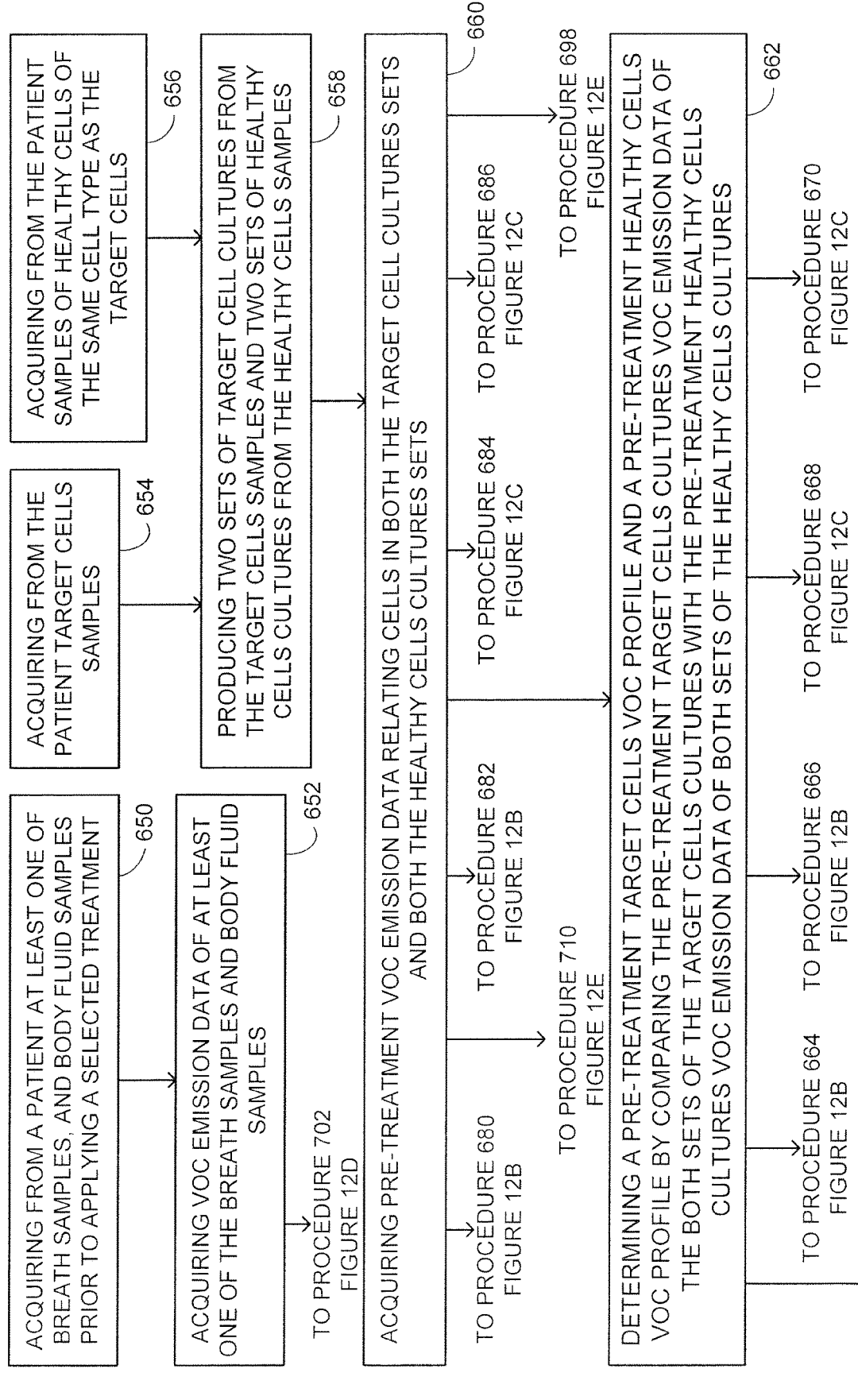
FIGS. 13A-13E are a schematic illustration of a method for determining treatment efficacy for an individual, operative in accordance with another embodiment of the disclose technique.
Figure 13B:
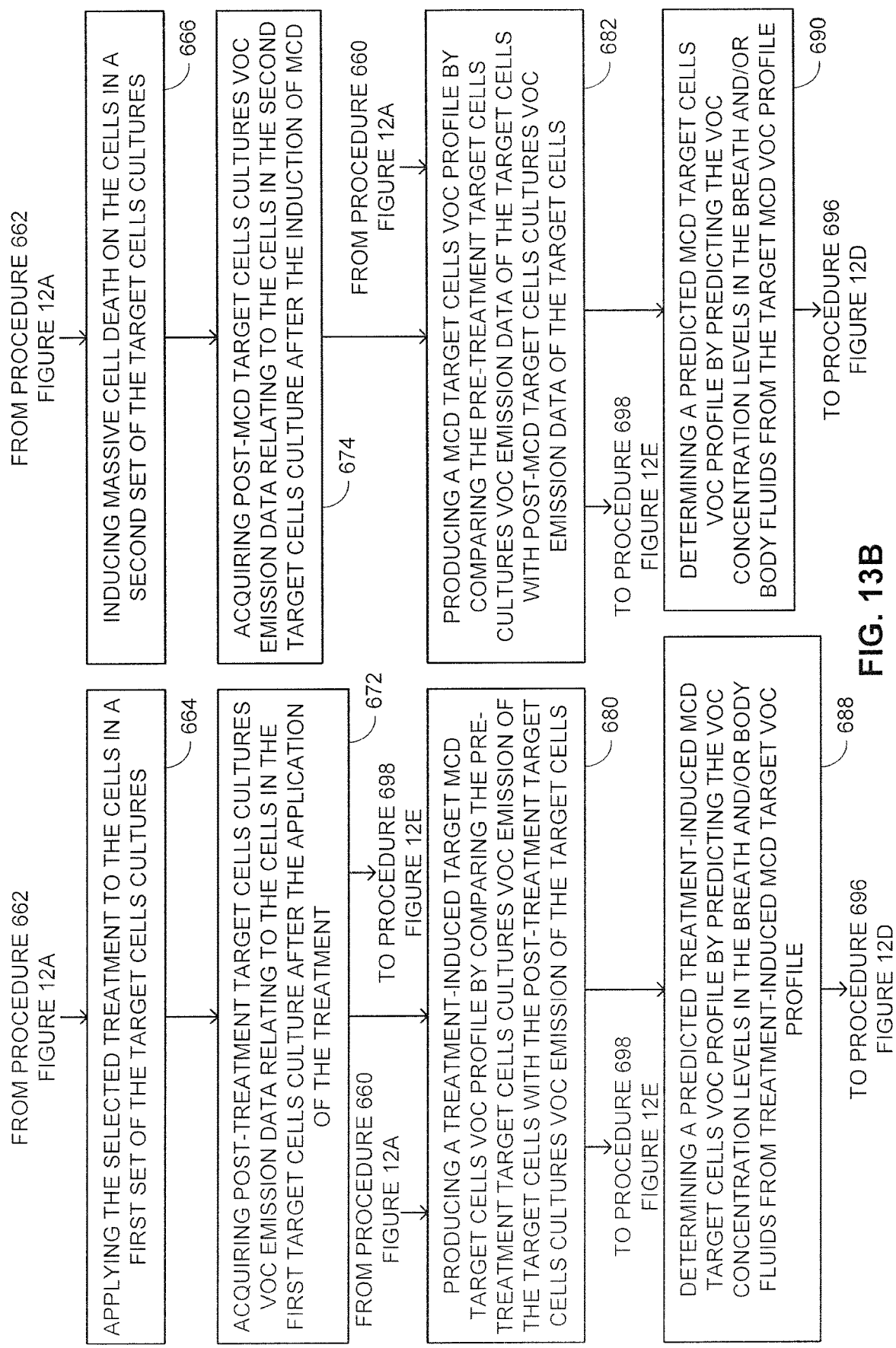
Figure 13C:
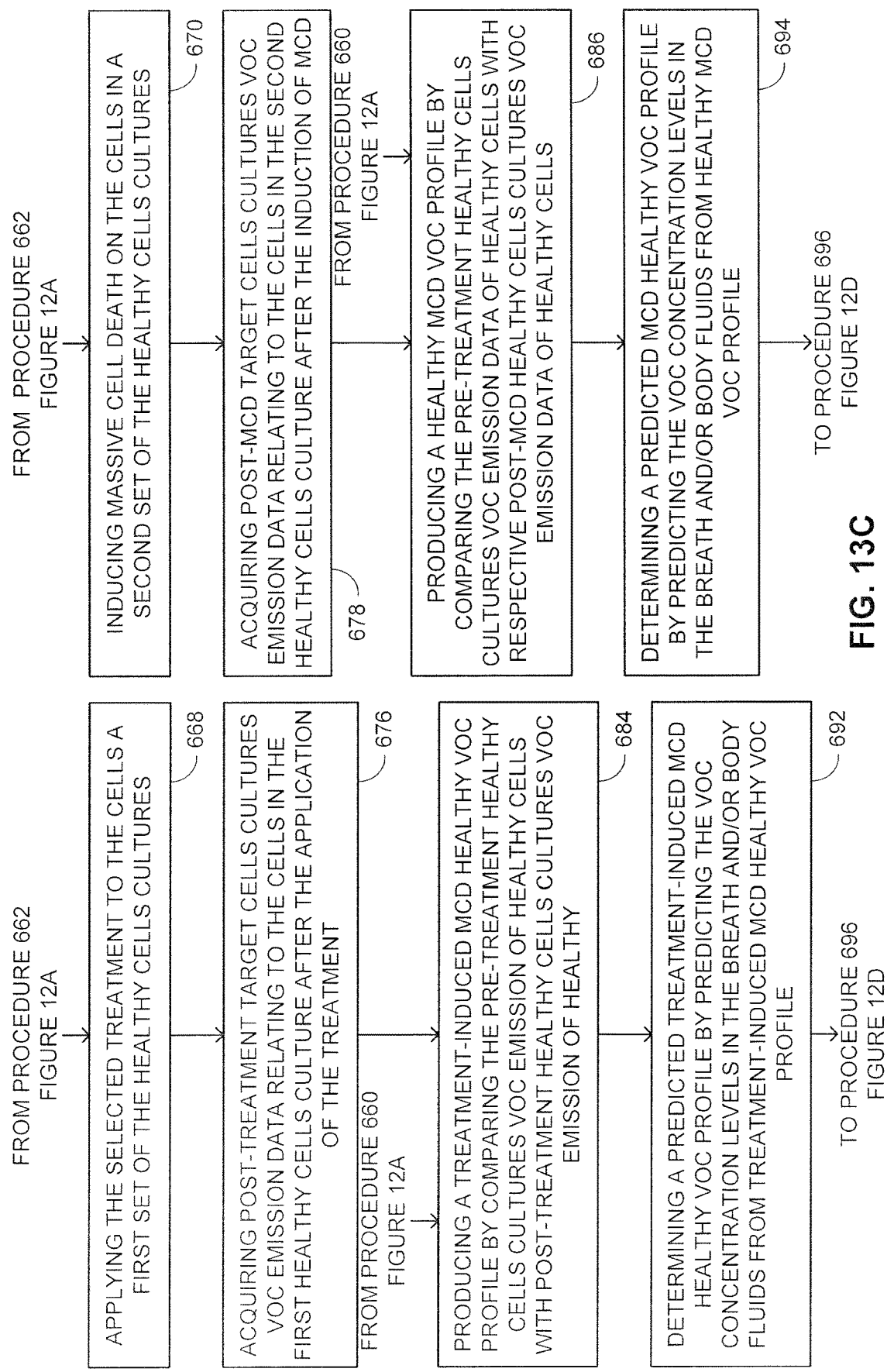
Figure 13D:
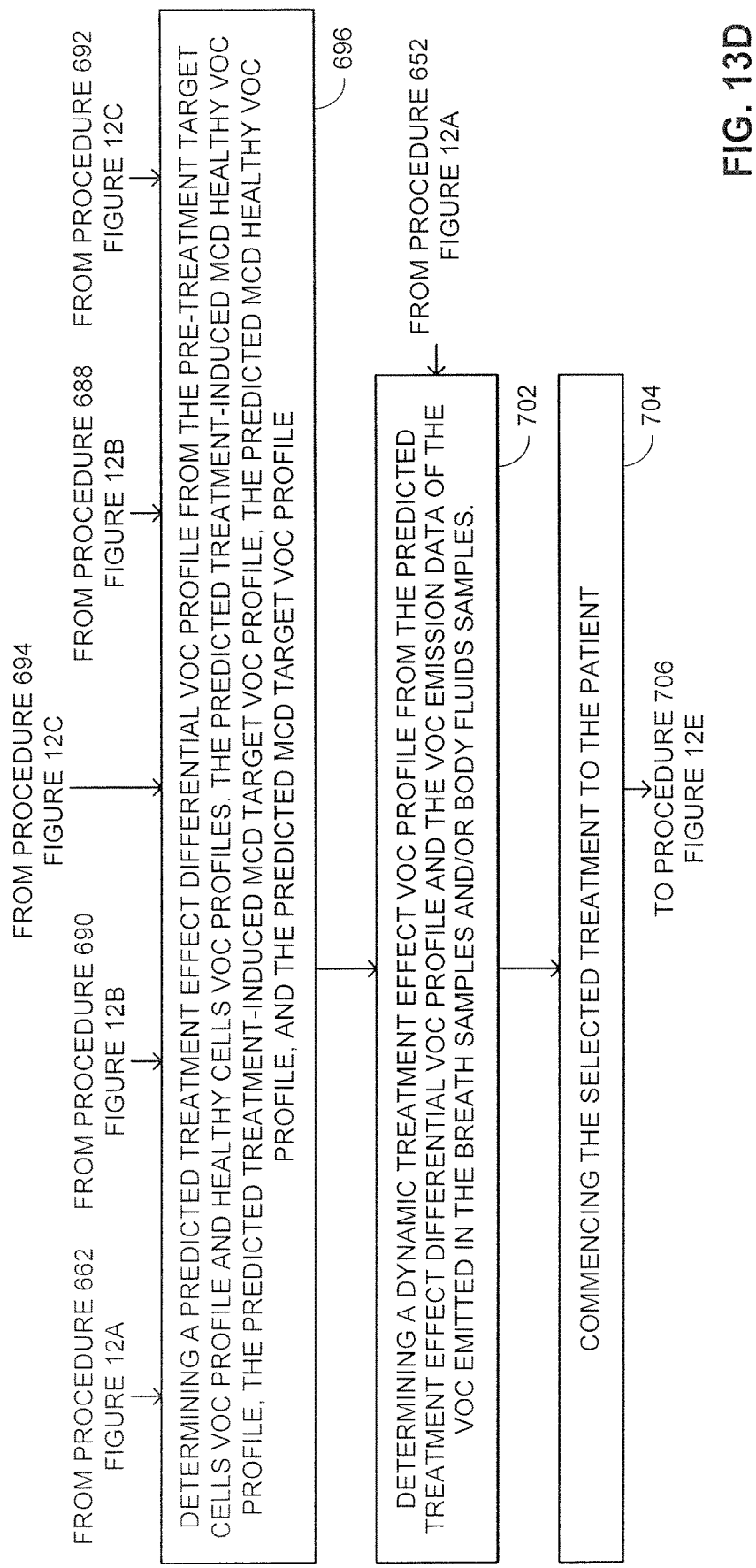
Figure 13E:
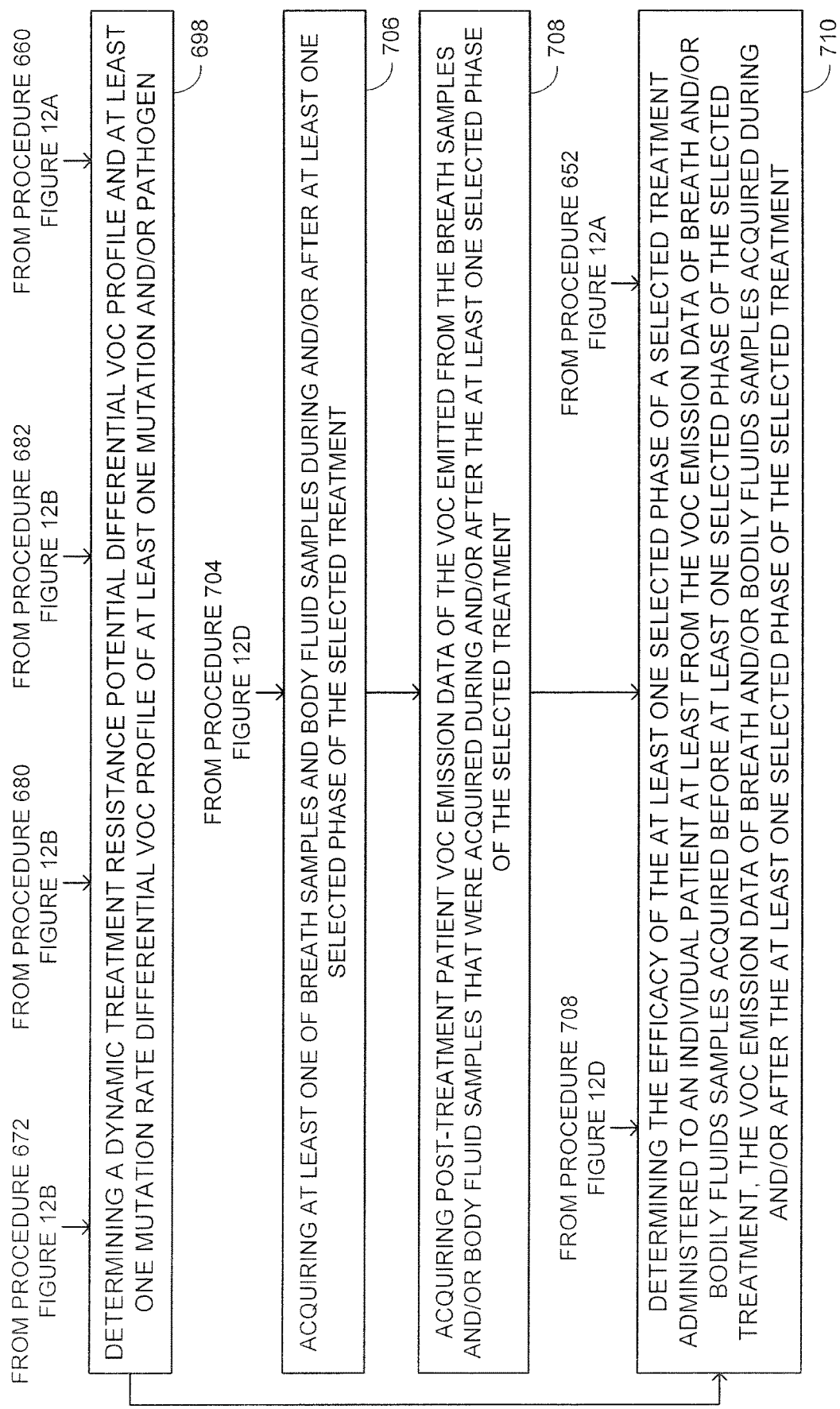

Reference is now made to FIG. 12 which is a schematic illustration of a method for determining treatment efficacy, operative in accordance with a further embodiment of the disclosed technique.

In procedure 600, breath samples and/or body fluid samples are acquired from a patient prior to at least one phase of a treatment. After procedure 600, the method proceeds to procedure 602.

In procedure 602, VOC emission data of the VOC emitted by the breath samples and/or body fluid samples is acquired prior to at least one phase of a treatment. With reference to FIG. 1, analysis device 102 acquires VOC emission data of the VOC emitted by the breath samples and/or body fluid samples. After procedure 602, the method proceeds to procedure 604 and 610.

In procedure 604, a stored Dynamic Differential VOC profile (e.g., as determined in conjunction with FIGS. 4A-4D, 5A-5C, 6A-6D and 7A-7B), which corresponds to the acquired VOC emission data is identified, thereby associating a pathological condition with the VOC emissions data. Since the identified stored Dynamic Differential VOC profile is associated with a corresponding pathological condition, the acquired VOC emission data is also associated with that pathological condition (e.g., a corresponding carcinogenic gene mutation or a pathological condition which results from pathogens). In general, following the description above, a stored Dynamic Differential VOC profile is composed of at least one target cells VOC profile and may further be composed of a plurality of additional VOC profiles. With reference to FIG. 1, processor 106 identifies a Dynamic Differential VOC profile corresponding to the acquired VOC emission data. After procedure 604 the method proceeds to procedure 606.

In procedure 606 breath samples and/or body fluid samples are acquired during and/or after the at least one selected phase of the selected treatment. After procedure 606 the method proceeds to procedure 608.

In procedure 608, VOC emission data, of the VOCs emitted in the breath samples and/or body fluid samples is acquired during and/or after the at least one selected phase of the selected treatment. With reference to FIG. 1, analysis device 102 acquires VOC emission data, of the VOCs emitted in the breath samples and/or body fluid samples after the treatment. After procedure 608 the method proceeds to procedure 610.

In procedure 610, the efficacy of the treatment is classified at least by determining the concentration values of the VOCs in the identified Dynamic Differential VOC profile acquired before said at least one phase of said treatment with the concentration values of the VOCs in the identified Dynamic Differential VOC profile acquired during and/or after the at least one phase of the treatment. For example, when the concentration values of the VOCs in the identified Dynamic Differential VOC profile during and/or after the treatment are reduced relative to the concentration values of the VOCs in the identified Dynamic Differential VOC profile before the treatment, the treatment may be classified as successful. Otherwise, the treatment may be classified as un-successful. To detect if a new mutation occurred, the VOC emission data acquired before treatment and during and/or after treatment are compared with other Dynamic Differential VOC profiles stored in a database. If a new mutation did not occur (i.e., other Dynamic Differential VOC profiles were not identified in the database), than the treatment may be considered successful. With reference to FIG. 1, processor 106 determines treatment efficacy.

As mentioned above, VOC profiles may be employed to determine treatment efficacy at selected phases of a selected treatment and to detect the development of mutations that could render the treatment ineffective. For example, these VOC profiles may be employed to determine the efficacy of chemotherapy. Moreover, in the case of cancer treatment, the VOC profiles may be employed to determine if the cells have mutated to another cancer sub-type during treatment, thereby rendering the treatment ineffective.

Reference is now made to FIGS. 13A-13E, which are a schematic illustration of a method for determining treatment efficacy for an individual, operative in accordance with another embodiment of the disclose technique.

In procedure 650, at least one of breath samples and body fluids samples are acquired from a patient prior to applying a selected treatment. After procedure 650 the method proceeds to procedure 652.

In procedure 652, VOC emission data of the at least one of breath and body fluid samples is acquired before the at least one selected phase of the selected treatment. VOC emission data of breath and/or body fluid samples, acquired before the at least one selected phase of the selected treatment, is referred to as pre-treatment patient VOC emission data. With reference to FIG. 1, analysis device 102 acquires emission data of at least one of the breath samples and/or body fluids samples. From procedure 652, the method proceeds to procedure 702.

In procedure 654, target cells samples are acquired from the patient. From procedure 654, the method proceeds to procedure 658.

In procedure 656, healthy cells samples, of the same type as the target cells are acquired from the patient. From procedure 656, the method proceeds to procedure 658.

In procedure 658, two sets of target cells cultures (i.e., target cells cultures 'A' and target cells cultures 'B') and two sets of healthy cells cultures (i.e., healthy cells cultures 'A' and healthy cells cultures 'B') are produced from the target cells samples and from the healthy cells samples respectively. Each set includes at least one culture. From procedure 658, the method proceeds to procedure 660.

In procedure 660, pre-treatment target cells cultures VOC emission data, relating to both target cells cultures sets (i.e., target cells cultures set 'A' and target cells cultures set 'B') and pre-treatment healthy cells cultures VOC emission data relating to both healthy cells cultures (i.e., healthy cells cultures set 'A' and healthy cells cultures set 'B') are acquired. With reference to FIG. 1, analysis device 102 acquires VOC emission data relating to the both target cells cultures and the both healthy cells cultures. From procedure 660, the method proceeds to procedures 662, 680, 682, 684, 686 and 698.

In procedure 662, a pre-treatment target cells VOC profile and a pre-treatment healthy cells VOC profile are determined by comparing the pre-treatment target cells cultures VOC emission data of the both sets of the target cells cultures (i.e., target cells cultures set 'A' and target cells cultures set 'B') with the pre-treatment healthy cells cultures VOC emission data of both sets of the healthy cells cultures (i.e., healthy cells cultures set 'A' and healthy cells cultures set 'B'). With reference to FIG. 1, processor 106 determines the pre-treatment target cells VOC profile and the pre-treatment healthy cells VOC profile. From procedure 662, the method proceeds to procedures 680 and 698.

In procedure 664, the selected treatment is applied to the target cells in a first set of target cells cultures (e.g., target cells cultures set 'A'). From procedure 664, the method proceeds to procedure 672.

In procedure 666, massive cell death is induced on the target cells in second set of the target cells cultures (i.e., target cells culture set 'B') in way that does not generate residual VOC artifacts (e.g., by employing flash freeze techniques, or Ultra Violet—UV light techniques to the target cells cultures). From procedure 666, the method proceeds to procedure 674.

In procedure 668, the selected treatment is applied to the healthy cells in a first set of healthy cells cultures (i.e., healthy cells cultures set 'A'). From procedure 668, the method proceeds to procedure 676.

In procedure 670, massive cell death is induced on the healthy cells in a second set of healthy cells cultures (i.e., healthy cells cultures set 'B'), in a way that does not generate residual VOC artifacts (e.g., by employing flash freeze techniques, or Ultra Violet—UV light techniques to the healthy cells cultures). From procedure 670, the method proceeds to procedure 678.

In procedure 672, post-treatment target cells cultures VOC emission data relating to the target cells in the first set of target cells cultures (i.e., target cells cultures set 'A') is acquired after the application of the treatment. With reference to FIG. 1, analysis device 102 acquires post-treatment target cells cultures VOC emission data relating to the target cells in the first set of target cells cultures after the application of the treatment. After procedure 672, the method proceeds to procedure 680 and 698.

In procedure 674, post-MCD target cells cultures VOC emission data relating to the target cells in the second target cells culture (i.e., target cells cultures set 'B') is acquired after the induction of MCD. With reference to FIG. 1, analysis device 102 acquires post-MCD target cells cultures VOC emission data relating to the target cells in the second target cells culture, after the induction of MCD. After procedure 674, the method proceeds to procedure 682.

In procedure 676, post-treatment healthy cells cultures VOC emission data relating to the cells in the first set of healthy cells culture (i.e., healthy cells cultures set 'A') is acquired after the application of the treatment. With reference to FIG. 1, analysis device 102 acquires post-treatment healthy cells cultures VOC emission data relating to the healthy cells the first set of healthy cells culture after the application of the treatment. After procedure 676, the method proceeds to procedure 684.

In procedure 678, post-MCD healthy cells cultures VOC emission data relating to the cells in the second set of healthy cells cultures (i.e., healthy cells cultures set 'B') is acquired after the induction of MCD. With reference to FIG. 1, analysis device 102 acquires post-MCD healthy cells cultures VOC emission data relating to the healthy cells in the second set of healthy cells cultures, after the induction of MCD. After procedure 678, the method proceeds to procedure 686.

In procedure 680, a treatment-induced MCD target cells VOC profile is produced by comparing the pre-treatment target cells cultures VOC emission data of the target cells in the first set of target cells cultures (i.e., target cells cultures set 'A') with the post-treatment target cells cultures VOC emission data of the target cells in the first set of target cells cultures (i.e., target cells cultures set 'A'). The treatment-induced MCD target cells VOC profile relates to the VOCs emitted by the target cells cultures set 'A' when MCD was induced by the selected treatment. With reference to FIG. 1, processor 106 produces a treatment-induced MCD target cells VOC profile by comparing the pre-treatment target cells cultures VOC emission data of the target cells in the first set of target cells cultures' with the post-treatment target cells cultures VOC emission data of the target cells in the first set of target cells cultures. After procedure 680, the method proceeds to procedure 688 and 698.

In procedure 682, a MCD target cells VOC profile is produced by comparing the pre-treatment target cells cultures VOC emission data of the target cells in the second set of target cells cultures (i.e., target cells cultures set 'B') with post-MCD target cells cultures VOC emission data of the target cells in the second set of target cells cultures (i.e., target cells cultures set 'B'). The MCD target cells VOC profile relates to the VOCs emitted by the target cells cultures 'B' when MCD is induced in a way that does not generate residual VOC artifacts (e.g., by employing flash freeze techniques, or Ultra Violet—UV light techniques). With reference to FIG. 1, processor 106 produces a MCD target cells VOC profile by comparing the pre-treatment target cells cultures VOC emission data of the target cells in the second set of target cells cultures with the post-MCD target cells cultures VOC emission data of the target cells in the second set of target cells cultures. After procedure 682, the method proceeds to procedure 690 and 698.

In procedure 684, a treatment-induced MCD healthy cells VOC profile is produced by comparing the pre-treatment healthy cells cultures VOC emission data of the healthy cells in the first set of healthy cells cultures (i.e., healthy cells cultures set 'A') with the post-treatment healthy cells cultures VOC emission data of the healthy cells in the first set of healthy cells cultures (i.e., healthy cells cultures set 'A'). The treatment-induced MCD healthy cells VOC profile relates to the VOCs emitted by the healthy cells cultures 'A' when MCD was induced by the selected treatment. With reference to FIG. 1, processor 106 produces a treatment-induced MCD healthy cells VOC profile by comparing the pre-treatment healthy cells cultures VOC emission data of the healthy cells in the first set of healthy cells cultures with the post-treatment healthy cells cultures VOC emission data of the healthy cells in the first set of healthy cells cultures.

In procedure 686, a MCD healthy cells VOC profile is produced by comparing the pre-treatment healthy cells cultures VOC emission data of the healthy cells in the second set of healthy cells cultures (i.e., healthy cells cultures set 'B') with post-MCD healthy cells cultures VOC emission data of the healthy cells in the second set of healthy cells cultures (i.e., healthy cells cultures set 'B'). The MCD healthy cells VOC profile relates to the VOCs emitted by the healthy cells cultures 'B' when MCD is induced in a way that does not generate residual VOC artifacts (e.g., by employing flash freeze techniques, or Ultra Violet—UV light techniques). With reference to FIG. 1, processor 106 produces a MCD healthy cells VOC profile by comparing the pre-treatment healthy cells cultures VOC emission data of the healthy cells in the second set of healthy cells cultures with the post-MCD healthy cells cultures VOC emission data of the healthy cells in the second set of healthy cells cultures. After procedure 686, the method proceeds to procedure 694.

In procedure 688, a predicted treatment-induced MCD target cells VOC profile is determined by predicting the VOC concentration levels in the breath and/or body fluids from a treatment-induced MCD target cells VOC profile. The VOC concentration levels are predicted by using a diffusion model such as the Farhi equation or a modified Farhi's model, both further elaborated below. With reference to FIG. 1, processor 106 determines a predicted treatment-induced MCD target cells VOC profile. After procedure 688, the method proceeds to procedure 696.

In procedure 690, a predicted MCD target cells VOC profile is determined by predicting the VOC concentration levels in the breath and/or body fluids from the MCD target cells VOC profile. The VOC concentration levels are predicted by using a diffusion model such as the Farhi equation or a modified Farhi's model, both further elaborated below. With reference to FIG. 1, processor 106 determines a predicted MCD target cells VOC profile. After procedure 690, the method proceeds to procedure 696.

In procedure 692, a predicted treatment-induced MCD healthy cells VOC profile is determined by predicting the VOC concentration levels in the breath and/or body fluids from a treatment-induced MCD healthy cells VOC profile. The VOC concentration levels are predicted by using a diffusion model such as the Farhi equation or a modified Farhi's model, both further elaborated below. With reference to FIG. 1, processor 106 determines a predicted treatment-induced MCD healthy cells VOC profile. After procedure 692, the method proceeds to procedure 696.

In procedure 694, a predicted healthy MCD VOC profile is determined by predicting the VOC concentration levels in the breath and body fluids from the MCD healthy cells VOC profile. The VOC concentration levels are predicted by using a diffusion model such as the Farhi equation or a modified Farhi's model, both further elaborated below. With reference to FIG. 1, processor 106 determines a predicted MCD healthy cells VOC profile. After procedure 694, the method proceeds to procedure 696.

In procedure 696, a predicted treatment effect differential VOC profile is determined from the pre-treatment target cells VOC profile, the pre-treatment healthy cells VOC profile, the predicted treatment-induced MCD healthy cells VOC profile, the predicted treatment-induced MCD target cells VOC profile, the predicted MCD healthy cells VOC profile, and the predicted MCD target cells VOC profile. With reference to FIG. 1, processor 106 determines a predicted treatment effect differential VOC profile. From procedure 696, the method proceeds to procedure 702.

In procedure 698, a dynamic treatment resistance potential differential VOC profile and at least one mutation rate differential VOC profile of at least one mutation and/or pathogen are determined. Initially, the post-treatment target cells cultures VOC emission data of the target cells in target cells culture set 'A' is filtered with the MCD target cells VOC profile and with treatment-induced MCD target cells VOC profile, to alleviate cell death related VOCs. The filtered post-treatment target cells cultures VOC emission data is compared with the pre-treatment target cells VOC profile to determine a dynamic treatment resistance potential profile. The concentration levels of the VOCs in this treatment resistance potential profile are indicative of the portion of the cells that survived the treatment and did not mutate.

The filtered post-treatment target cells cultures VOC emission data is further filtered with the pre-treatment target cells VOC profile. The twice filtered post-treatment target cells cultures VOC emission data is compared with stored Dynamic Differential VOC profiles (e.g., such as determined herein above in conjunction with FIGS. 3A-3C, 5A-5C and 6A-6D) to determine a mutation rate differential VOC profile or profiles of various mutations and/or pathogens. The concentration levels of the VOCs in these mutation rate differential VOC profiles are indicative of the mutation rate of various mutations and pathogens (i.e., the portion of the cells that mutated during the treatment and the number of new mutations that appeared after the treatment). With reference to FIG. 1, processor 106 determines a dynamic treatment resistance potential profile and a mutation rate differential VOC profile or profiles of various mutations and/or pathogens. After procedure 698 the method proceeds to procedure 710.

In procedure 702, a dynamic treatment effect VOC profile is determined from the predicted treatment effect differential VOC profile and the VOC emission data of the VOCs emitted in the breath samples and/or body fluids samples. With reference to FIG. 1, processor 106 determines a dynamic treatment effect VOC profile. After procedure 702, the method proceeds to procedure 704.

In procedure 704, the selected treatment to the patient is commenced. After procedure 704, the method proceeds to procedure 706.

In procedure 706, at least one of breath samples and/or body fluid samples are acquired from the patient during and/or after at least one selected phase of the selected treatment. Breath samples and/or body fluid samples acquired from the patient during and/or after at least one selected phase of the selected treatment are referred to herein as post-treatment patient VOC emission data. After procedure 706, the method proceeds to procedure 708.

In procedure 708, post-treatment patient VOC emission data, of the VOC emitted in the breath samples and/or body fluid samples that were acquired during and/or after at least one selected phase of the selected treatment. With reference to FIG. 1, analysis device 102 acquires the VOC emission data of the VOCs emitted in the breath samples and/or body fluid samples during and/or after at least one selected phase of the selected treatment. After procedure 708, the method proceeds to procedure 710.

In procedure 710, the efficacy of at least one selected phase of a selected treatment administered to an individual patient (i.e., individual personal treatment efficacy) is determined at least from the VOC emission data of breath and/or bodily fluids samples acquired before at least one selected phase of the selected treatment, and the VOC emission data of breath and/or bodily fluids samples acquired during and/or after at least one selected phase of the selected treatment (i.e., pre-treatment patient VOC emission data and the post-treatment patient VOC emission data). To determine the efficacy of the selected phase of the selected treatment, the following are determined:

Concentration values of the VOCs in the pre-treatment target cells VOC profile, before the selected phase of the selected treatment, from pre-treatment patient VOC emission data.

The concentration values of the VOCs in the pre-treatment target cells VOC profile, during and/or after the selected phase of the selected treatment, from the post-treatment patient VOC emission data.

The concentration values of the VOCs in the predicted treatment-induced MCD target cells VOC profile, before the selected phase of the selected treatment, from the pre-treatment patient VOC emission data.

The concentration values of the VOCs in the predicted treatment-induced MCD target cells VOC profile, during and/or after the selected phase of the selected treatment, from the post-treatment patient VOC emission data.

The concentration values of the VOCs in the predicted MCD target cells VOC profile before the selected phase of the selected treatment, from the pre-treatment patient VOC emission data.

The concentration values of the VOCs in the predicted MCD target cells VOC profile during and/or after the selected phase of the selected treatment, from the post-treatment patient VOC emission data.

The selected phase of the selected treatment is determined as effective when concentration values of the VOCs in the predicted MCD target cells VOC profile during and/or after the selected phase of the treatment from the the-treatment patient VOC emission data associated with at least one of breath samples and body fluid samples is greater than concentration values of the VOCs in the predicted MCD target cells VOC profile before the selected phase of the treatment from the pre-treatment patient VOC emission data associated with at least one of breath samples and body fluid samples The treatment is further determine as effective when concentration values from the VOC emission data of pre-treatment target cells cultures, of VOCs associated with the pre-treatment target cells VOC profile, are greater than concentration values from the VOC emission data of post-treatment target cells cultures, of VOCs associated with the pre-treatment target cells VOC profile.

The treatment is further determined as effective when concentration values of the VOCs associated with the pre-dicted treatment-induced MCD target cells VOC profile, from the post-treatment patient VOC emission data associated with at least one of breath samples and body fluid samples are greater than concentration values of the VOCs associated with the predicted treatment-induced MCD target cells VOC profile the pre-treatment patient VOC emission data associated with at least one of breath samples and body fluid samples.

Further, to determine the efficacy of the selected phase of the selected treatment, the following is also determined:
- The concentration values of the VOCs in the pre-treatment healthy cells VOC profile relating to the healthy cells, before the selected phase of the selected treatment, from pre-treatment patient VOC emission data.
- The concentration values of the VOCs in the pre-treatment healthy cells VOC profile, during and/or after the selected phase of the selected treatment, are determined from the post-treatment patient VOC emission data.
- The concentration values of the VOCs in the predicted treatment-induced MCD healthy cells VOC profile, before the selected phase of the selected treatment, from the pre-treatment patient VOC emission data.
- The concentration values of the VOCs in the predicted treatment-induced MCD healthy cells VOC profile, during and/or after the selected phase of the selected treatment, from the post-treatment patient VOC emission data.
- The concentration values of the VOCs in the predicted MCD healthy cells VOC profile before the selected phase of the selected treatment from the pre-treatment patient VOC emission data.
- The concentration values of the VOCs in the predicted MCD healthy cells VOC profile during and/or after the selected phase of the selected treatment, from the post-treatment patient VOC emission data.

The treatment is determined as effective when the concentration values of from said post-treatment patient VOC emission data associated with at least one of breath samples and body fluid samples of VOCs in said predicted treatment-induced MCD healthy VOC remain unchanged (e.g., the difference between the values is within a pre-determined threshold) to concentration values from said pre-treatment patient VOC emission data associated with at least one of breath samples and body fluid samples, of VOCs in said predicted treatment-induced MCD healthy VOC The efficacy of a selected phase of a selected treatment may further be determined from the concentration values of the VOCs in the dynamic patient treatment resistance potential differential VOC profile and the concentration values of the VOCs in the mutation rate differential VOC profile before the selected phase of the selected treatment and during and/or after the selected phase of the selected treatment. The concentration values of the VOCs in the dynamic patient treatment resistance potential differential VOC profile and in the mutation rate differential VOC profile before the treatment are determined from the pre-treatment patient VOC emission data.

The concentration values of the VOCs in the dynamic patient treatment resistance potential differential VOC profile and in the mutation rate differential VOC profile during and/or after the selected phase of the selected treatment are determined from the post-treatment patient VOC emission data. The selected phase of the selected treatment is determined as effective when concentration values of the VOCs in the dynamic patient treatment resistance potential differential VOC profile before the selected phase of the selected treatment and during and/or after the selected phase of the selected treatment, remain unchanged. Also, the selected phase of the selected treatment is determined as effective when concentration values of the VOCs in the mutation rate differential VOC profile, during and/or after at least one selected phase of the selected treatment, remain un-changed relative to the concentration values of these VOCs before the selected phase of the selected treatment.

Furthermore, the selected phase of the selected treatment is determined as effective when no new mutations are identified. A new mutation or mutations are identified by comparing the post-treatment patient VOC emission data with stored dynamic differential VOC profiles. Prior to the attempt to identify a new mutation or mutations, the post-treatment patient VOC emission data is filtered with the pre-treatment target cells VOC profile, with the treatment-induced MCD target cells VOC profile, and with the MCD target cells VOC profile thereby alleviating information relating to the VOCs associated with the pre-treatment target cells VOC profile, the treatment-induced MCD target cells VOC profile, and the MCD target cells VOC profile.

With reference to FIG. 1, processor 106 determines the efficacy of at least one selected phase of a selected treatment administered to an individual patient.

Figure 14:
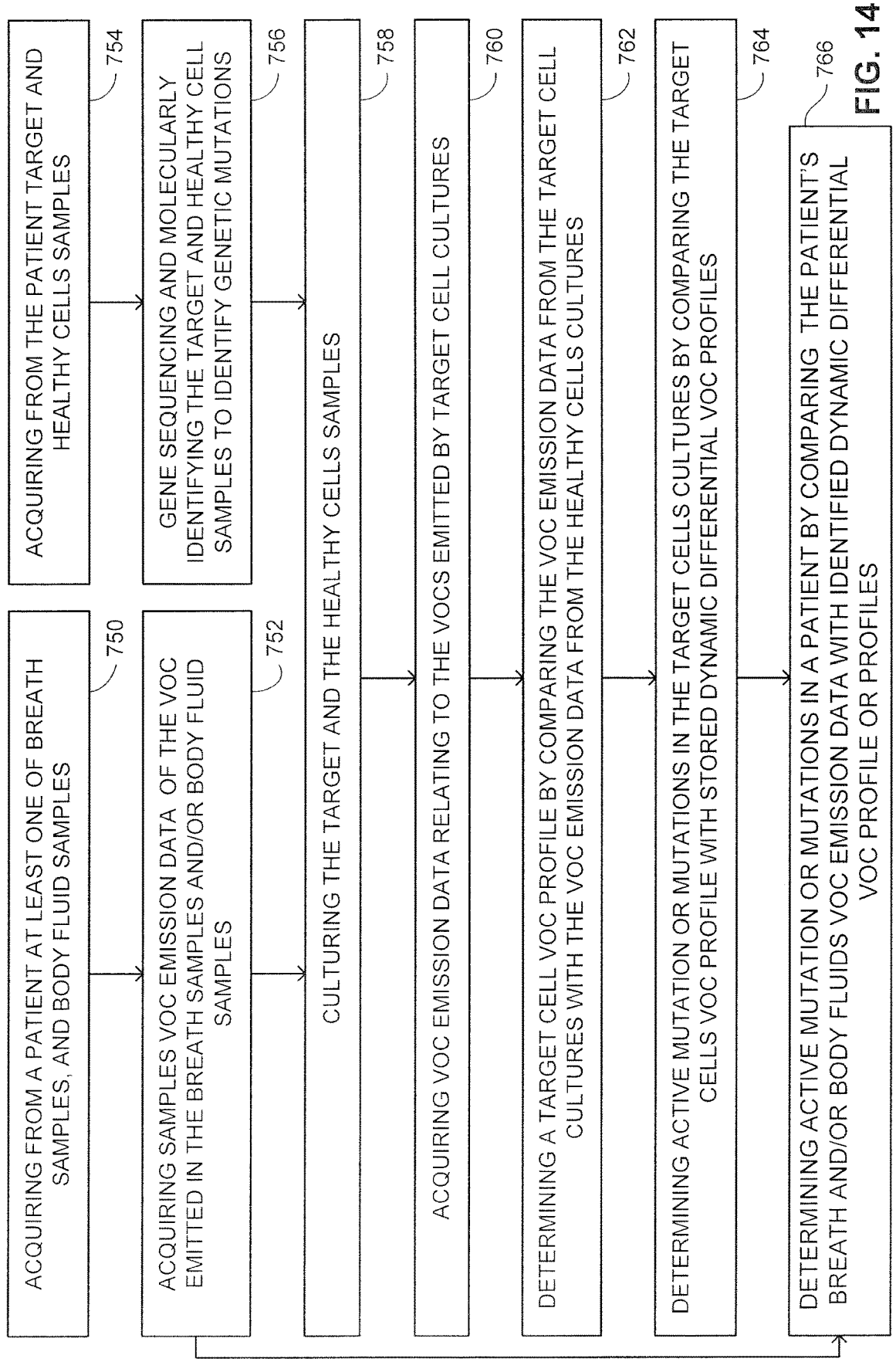
FIG. 14 is a schematic illustration of a method for distinguishing between active and inactive mutations in a patient and/or cultures, operative in accordance with a further embodiment of the disclosed technique.

Another use of stored VOC profiles is to distinguish between active and inactive mutations in a patient and/or cultures. Reference is now made to FIG. 14, which is a schematic illustration of a method for distinguishing between active and inactive mutations in a patient and/or cultures, operative in accordance with a further embodiment of the disclosed technique.

In procedure 750 at least one of breath samples and/or body fluid samples are acquired from the patient. After procedure 750, the method proceeds to procedure 752.

In procedure 752, VOC emission data of the VOCs emitted in the breath samples and/or body fluid samples are acquired. With reference to FIG. 1, analysis device 102 acquires VOC emission data of the VOCs emitted in the breath samples and/or body fluid samples. After procedure 752, the method proceeds to procedure 766.

In procedure 754, target and healthy cells samples are acquired from a patient. After procedure 754, the method proceeds to procedure 756.

In procedure 756, the target cells and the healthy cells are gene sequenced and undergo molecular identification to identify genetic mutations. After procedure 756, the method proceeds to procedure 758.

In procedure 758, the target and the healthy cells samples are cultured. After procedure 758, the method proceeds to procedure 760.

In procedure 760, VOC emission data, relating to the VOCs emitted by target and healthy cells cultures, is acquired. With reference to FIG. 1, analysis device 102 acquires VOC emission data relating to the VOCs emitted by target and healthy cells cultures. After procedure 760, the method proceeds to procedure 762.

In procedure 762, a target cell VOC profile is determined by comparing the VOC emission data from the target cells cultures with the VOC emission data from the healthy cells cultures. With reference to FIG. 1, processor 106 determines a target cell VOC profile by comparing the VOC emission data from the target cells cultures with the healthy cells cultures. After procedure 762, the method proceeds to procedure 764.

In procedure 764, active mutation or mutations in the target cells cultures is determined by comparing the target cells VOC profile with stored dynamic differential VOC profiles, determined as described hereinabove in conjunction with FIGS. 3A-3C, 5A-5C, 7A-7B, 8A-8B and 10A-10C.

With reference to FIG. 1, process 106 determines the active mutation or mutations in the target cells cultures from the list of mutations received by gene sequencing by comparing the target cells VOC profile with the VOC profiles in database 104. After procedure 764, the method proceeds to procedure 766.

In procedure 766, active mutation or mutations in a patient are determined by comparing the patient's breath and/or body fluids VOC emission data with identified Dynamic Differential VOC profile or profiles (i.e., identified Dynamic Differential VOC profile or profiles relates to Dynamic Differential VOC profile that were identified by comparing the target cells VOC profile with stored Dynamic Differential VOC profile). Further, the breath and/or body fluid VOC emission data is filtered with the target cells VOC profile. Furthermore, the filtered breath and/or body fluid VOC emission data is compared with stored dynamic differential VOC profiles, determined as described hereinabove in conjunction with FIGS. 3A-3C, 5A-5C, 7A-7B, 8A-8B and 10A-10C. With reference to FIG. 1, processor 106 determines the active mutation or mutations in the patient.

Figure 15A:
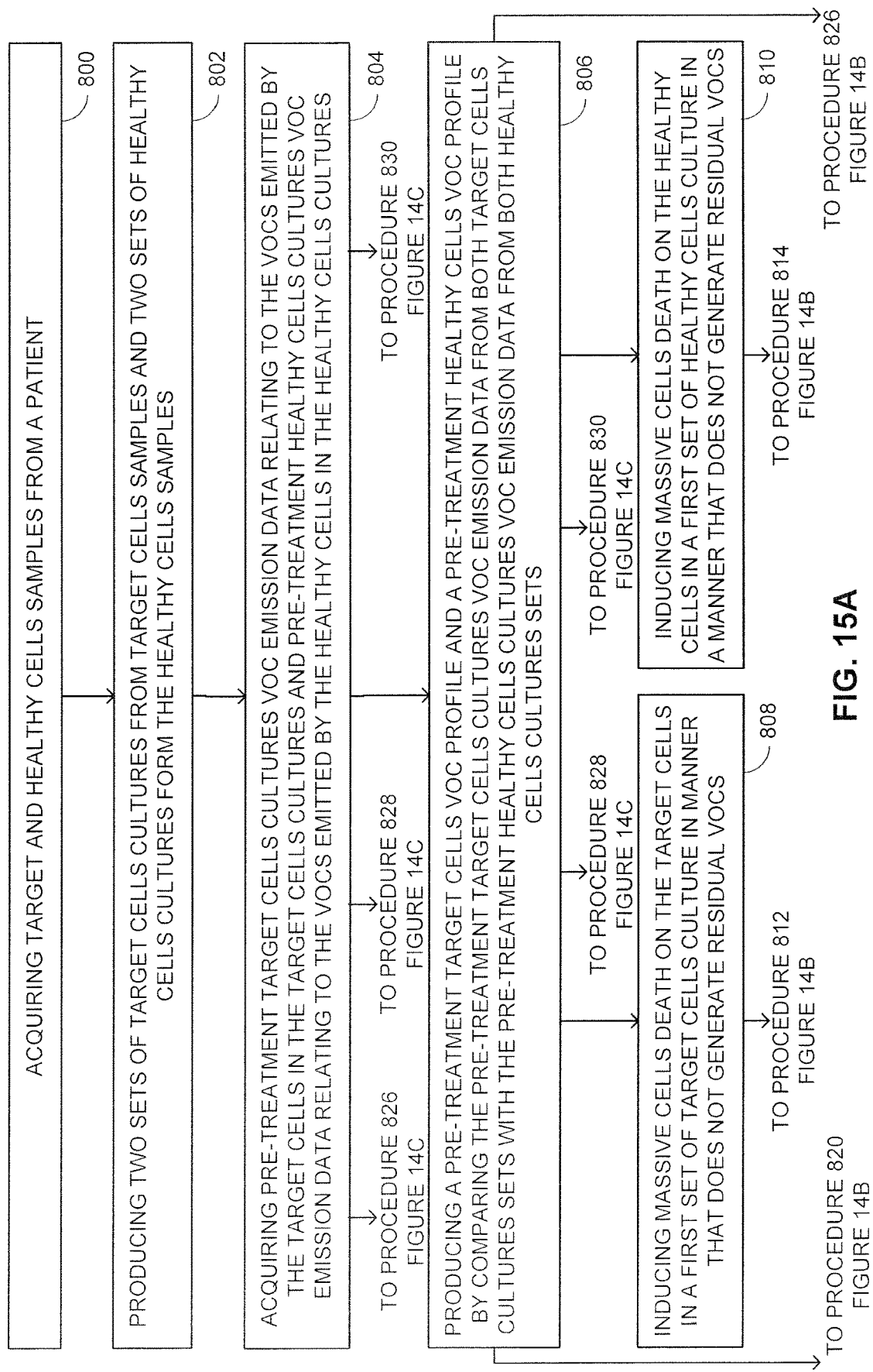
FIGS. 15A-15C are schematic illustrations of a method for determining an optimal treatment for a patient, operative in accordance with another embodiment of the disclosed technique.
Figure 15B:
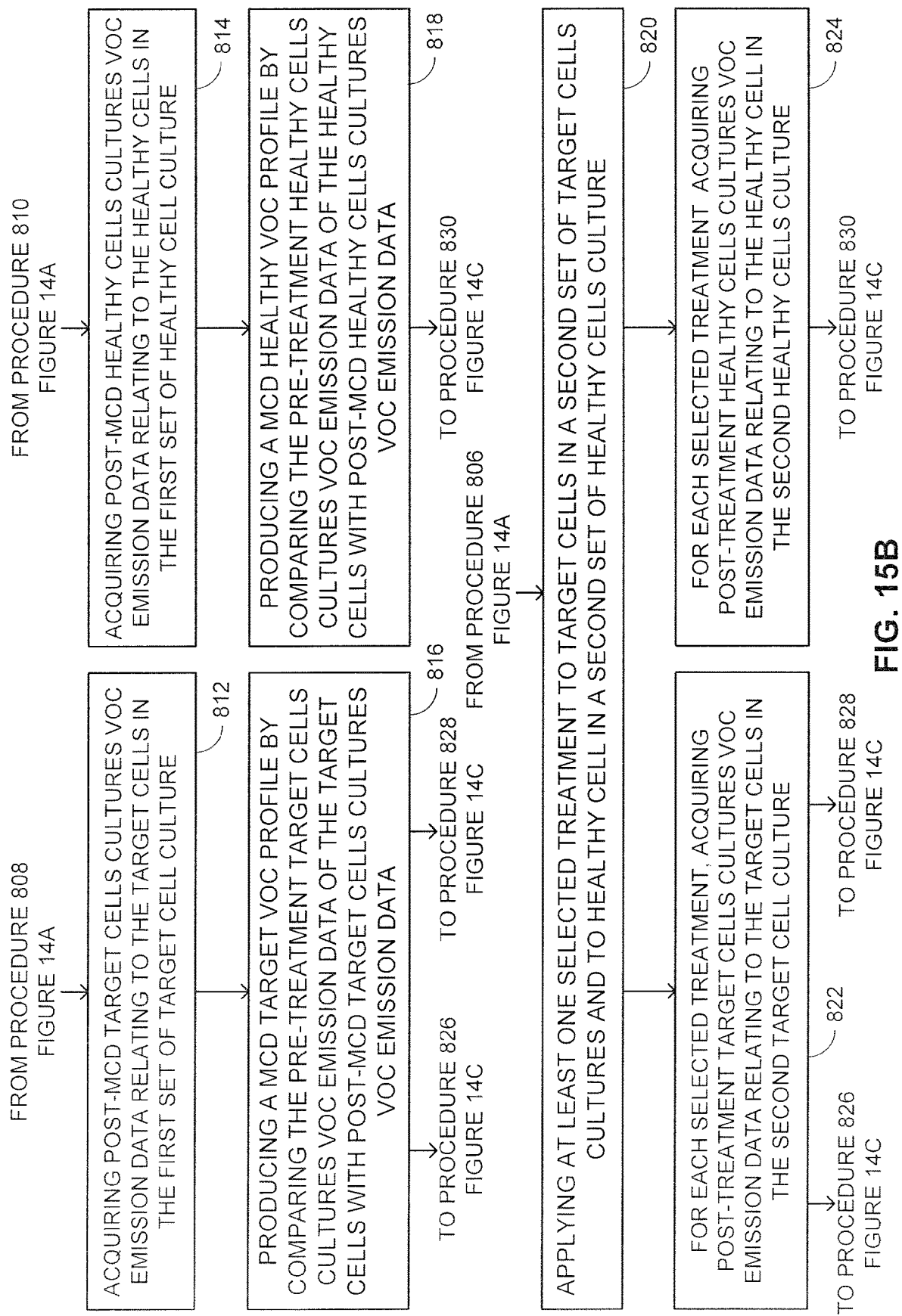
Figure 15C:
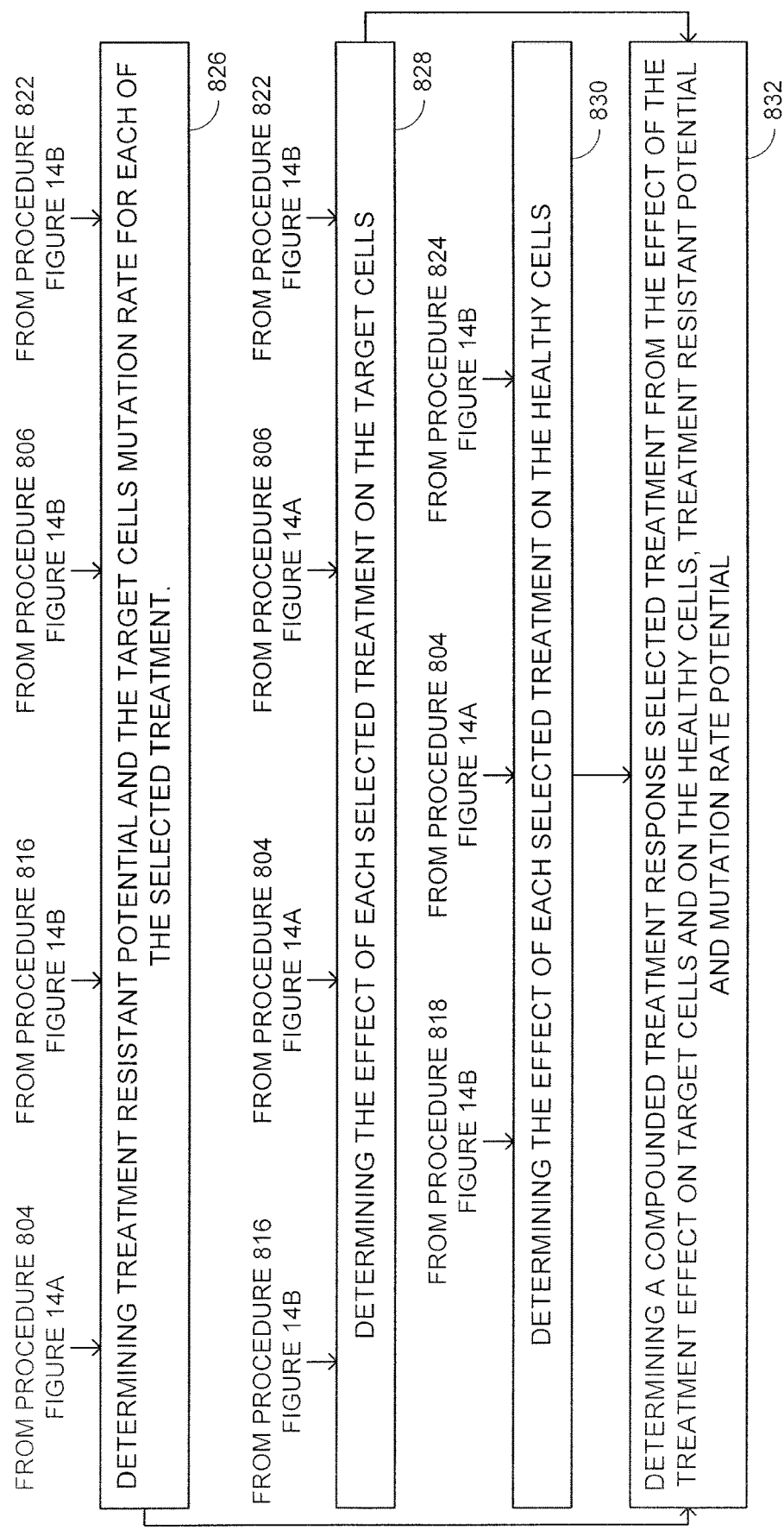

Another use of stored VOC profiles is to determine optimal treatment for a patient. Reference is now made to FIGS. 15A and 15B, which are a schematic illustration of a method for determining an optimal treatment for a patient, operative in accordance with another embodiment of the disclosed technique.

In procedure 800, target and healthy cells samples are acquired from a patient. After procedure 800, the method proceeds to procedure 802.

In procedure 802, two sets of target cells cultures (i.e., target cells cultures set 'A' and target cells cultures set 'B') and two sets of healthy cells cultures (i.e., healthy cells cultures set 'A' and healthy cells cultures set 'B') are produce from the target and healthy cells samples respectively. Each set includes at least one culture. After procedure 802, the method proceeds to procedure 804.

In procedure 804, pre-treatment target cells cultures VOC emission data relating to the VOCs emitted by the target cells in both target cells cultures sets (i.e., in target cells cultures set 'A' and in target cells cultures 'B'), and pre-treatment healthy cells cultures VOC emission data relating to the VOCs emitted by the healthy cells in both healthy cells cultures sets (i.e., in healthy cells cultures set 'A' and in healthy cells cultures set 'B') is acquired. With reference to FIG. 1, analysis device 102 acquires pre-treatment target cells cultures VOC emission data relating to the VOCs emitted by the target cells from the target cells in both target cells cultures sets as well as pre-treatment healthy cells cultures VOC emission data relating to the VOCs emitted by the healthy cells from the healthy cells in both healthy cells cultures sets. After procedure 804, the method proceeds to procedure 806, 826, 828 and 830.

In procedure 806, a pre-treatment target cells VOC profile and a pre-treatment healthy cells VOC profile are produced by comparing the pre-treatment target cells cultures VOC emission data from both target cells cultures sets (i.e., target cells cultures set 'A' and in target cells cultures 'B') with the pre-treatment healthy cells cultures VOC emission data from both healthy cells cultures sets (i.e., in healthy cells cultures set 'A' and in healthy cells cultures set 'B'). With reference to FIG. 1, processor 106 determines a pre-treatment target cell VOC profile and a pre-treatment healthy cells VOC profile by comparing the target cells cultures VOC emission data from the target cells cultures in both target cells cultures sets with the healthy cells cultures VOC emission data from the healthy cells cultures in both healthy cells cultures sets. After procedure 806, the method proceeds to procedure 808, 810, 820, 826, 828 and 830.

In procedure 808, massive cells death is induced on the target cells in a first set target cells cultures (i.e., target cells cultures set 'A') in a manner that does not generate VOC artifacts (e.g., by employing flash freeze techniques or UV light techniques). From procedure 808, the method proceeds to procedure 812.

In procedure 810, massive cells death is induced on the healthy cells in a first set of healthy cells cultures (i.e., healthy cells cultures set 'A') in a manner that does not generate residual VOCs in a manner that does not generate VOC artifacts (e.g., by employing flash freeze techniques or UV light techniques). From procedure 810, the method proceeds to procedure 814.

In procedure 812, post-MCD target cells cultures VOC emission data relating to the target cells in the first set of target cells culture (i.e., target cells cultures set 'A') is acquired. With reference to FIG. 1, analysis device 102 acquires post-MCD target cells cultures VOC emission data relating to the target cells in target cells culture 'A' after the induction of MCD. After procedure 812, the method proceeds to procedure 816.

In procedure 814, post-MCD healthy cells cultures VOC emission data relating to the healthy cells in the first set of healthy cells culture (i.e., healthy cells cultures set 'A') is acquired. With reference to FIG. 1, analysis device 102 acquires post-MCD healthy cells cultures VOC emission data relating to the healthy cells in healthy cells culture 'A' after the induction of MCD. After procedure 814, the method proceeds to procedure 818.

In procedure 816, a MCD target cells VOC profile is produced by comparing the pre-treatment target cells cultures VOC emission data with the post-MCD target cells cultures VOC emission data. The MCD target cells VOC profile relates to the VOCs emitted by the target cells in the first set of target cells cultures (i.e., target cells cultures set 'A') when MCD was induced in a way that does not generate residual VOC artifacts (e.g., by employing flash freeze techniques or UV light techniques). With reference to FIG. 1, processor 106 produces a MCD target cells VOC profile by comparing the pre-treatment target cells cultures VOC emission data of the target cells in the first set of target cells cultures with the post-MCD target cells cultures VOC emission data of the target cells in the first set of target cells culture. After procedure 816, the method proceeds to procedures 826 and 828.

In procedure 818, a MCD healthy cells VOC profile is produced by comparing the pre-treatment healthy cells cultures VOC emission data of the healthy cells in the first set of healthy cells cultures (i.e., healthy cells cultures set 'A'), with post-MCD healthy cells cultures VOC emission data of the healthy cells in the first set of healthy cells culture set (i.e., healthy cells cultures set 'A'). The MCD healthy cells VOC profile relates to the VOCs emitted by the healthy cells culture 'A' when MCD is induced in a way that does not generate residual VOC artifacts (e.g., by employing flash freeze techniques or UV light techniques). With reference to FIG. 1, processor 106 produces a MCD healthy cells VOC profile by comparing the pre-treatment healthy cells cultures VOC emission data of the healthy cells in the first set of healthy cells cultures with the post-MCD healthy cells cultures VOC emission data of the healthy cells in the first set of healthy cells culture. After procedure 818, the method proceeds to procedure 830.

In procedure 820, at least one selected treatment is applied to target cells in a second set of target cells cultures (i.e., target cells cultures set 'B') and to healthy cell in a second set of healthy cells (i.e., target cells cultures set 'B'). In cases when more than one treatment is applied, the treatments are employed as a comparison reference to one another. From procedure 820, the method proceeds to procedure 824.

In procedure 822, for each selected treatment, post-treatment target cells cultures VOC emission data relating to the target cells in the second set of target cells cultures (i.e., target cells cultures set 'B'), is acquired. With reference to FIG. 1, analysis device 102 acquires post-treatment target cells cultures VOC emission data relating to the target cells in the second set of target cells culture for each selected treatment. After procedure 822, the method proceeds to procedure 826 and 828.

In procedure 824, for each selected treatment, a post-treatment healthy cells cultures VOC emission data relating to the healthy cell in the second set of healthy cells culture (i.e., healthy cells cultures set 'B') is acquired after the application of the selected treatment. With reference to FIG. 1, analysis device 102 acquires post-treatment healthy cells cultures VOC emission data relating to the healthy cell in the second set of healthy cells culture for each selected treatment, after the application of the selected treatment. After procedure 824, the method proceeds to procedure 830.

In procedure 826, the treatment resistant potential and the target cells mutation rate are determined for each of the selected treatment. Treatment resistance potential and target cell mutation rate are both employed to determine if the selected treatment is effective or not (i.e., the effect of the treatment). Initially, the concentration values of VOCs in the pre-treatment target cells VOC profile are determined from the pre-treatment target cells cultures VOC emission data relating to target cells culture 'B' (i.e., determining the concentration levels of the relevant VOCs before the treatment). Then the post-treatment target cells cultures VOC emission data is filtered with the MCD target cells VOC profile, to alleviate cell death related VOCs. The concentration values of the VOCs in the pre-treatment target cells VOC profile are determined from the filtered post-treatment target cells cultures VOC emission data (i.e., determining the concentration levels of the relevant VOCs during and/or after the treatment). The treatment resistant potential of the selected treatment is determined by comparing the concentration values of the VOCs in the pre-treatment target cells VOC profile before the selected treatment with the concentration values of the VOCs in the pre-treatment target cells VOC profile during and/or after the selected treatment. The change in concentration levels of the relevant VOCs is indicative of the portion of the cells that survived the selected treatment and did not mutate. The selected treatment is determined effective when the concentration values of the VOCs in the pre-treatment target cells VOC profile reduce. The selected treatment may be rendered most effective when the concentration values of the VOCs in the pre-treatment target cells VOC profile are zero.

The filtered post-treatment target cells cultures VOC emission data is further filtered with the pre-treatment target cells VOC profile. The mutation rate potential is determined by comparing the twice filtered post-treatment target cells cultures VOC emission data with stored Dynamic Differential VOC profiles (e.g., such as determined herein above in conjunction with FIGS. 3A-3C, 5A-5C and 6A-6D), thus identifying a stored Dynamic Differential VOC profile or profiles corresponding to the twice filtered post-treatment target cells cultures VOC emission data. Then, the concentration values of the VOCs in the identified stored Dynamic Differential VOC profile or profiles are determined from the twice filtered post-treatment target cells cultures VOC emission data. The concentration levels of the identified stored Dynamic Differential VOC profiles are indicative of the mutation rate of various mutations and pathogens (i.e., the portion of the cells that mutated during the selected treatment and the number of new mutations that appeared after the selected treatment). The selected treatment is determined as most effective when no new stored Dynamic Differential VOC profiles are identified from the twice filtered post-treatment target cells cultures VOC emission data. When more than one selected treatment is employed, the optimal treatment may be determined by selecting the treatment which exhibits the highest change in the concentration levels of the VOCs in the pre-treatment target cells VOC profile that indicate a reduction of the pre-treatment target cells VOC profile in the post-treatment target cells cultures VOC emission data (i.e.—optimal efficiency is indicated when the pre-treatment target cells VOC profile is no longer identified in the post-treatment target cells cultures VOC emission data) and stored Dynamic Differential VOC profiles are either not identified in the post-treatment target cells cultures VOC emission data or in cases where they are identified in all the selected treatments, the treatment that exhibit the least change in the concentration levels of the VOCs in the identified stored Dynamic Differential VOC profile within the post-treatment target cells cultures VOC emission data may be determined as the optimal treatment. With reference to FIG. 1, processor 106 determines treatment resistance potential and mutation rate. After procedure 826, the method proceeds to procedure 832.

In procedure 828, the effect of each selected treatment on the target cells is determined. To determine the effect of the selected treatment, the concentration values of the VOCs in the pre-treatment target cells VOC profile before and after the treatment and the concentration values of the VOCs in the MCD target cells VOC profile before and after the treatment are determined. To that end, the concentration levels of the VOCs in the pre-treatment target cells VOC profile are determined from the pre-treatment target cells cultures VOC emission data acquired from target cells culture 'B'. Also, the concentration values of the VOCs in the MCD target cells VOC profile are determined from the pre-treatment target cells cultures VOC emission data acquired from target cells culture 'A'. Furthermore, the concentration values of the VOCs in the pre-treatment target cells VOC profile are determined from the post-treatment target cells cultures VOC emission data acquired from target cells culture 'B' and the concentration values of the VOCs in the MCD target cells VOC profile are determined from the post-treatment target cells cultures VOC emission data acquired from target cells culture 'A'. A selected treatment is determined as effective when:

(a) concentration values from the VOC emission data of pre-treatment target cells cultures, of VOCs associated with the pre-treatment target cells VOC profile, are greater than concentration values from the VOC emission data of post-treatment target cells cultures, of VOCs associated with the pre-treatment target cells VOC profile; and (b) concentration values from the VOC emission data of post-treatment target cells cultures, of VOCs associated with the MCD target cells VOC profile, emitted by the post-treatment target cell cultures, are greater than concentration values from the VOC emission data of pre-treatment target cells cultures, of VOCs associated with the MCD target cells VOC profile.

According to another example, the ratio between concentration values from the VOC emission data of post-treatment target cells cultures, of VOCs associated with the MCD VOC profile, emitted by the post-treatment target cell cultures and the concentration values from the VOC emission data of post-treatment target cells cultures, of VOCs associated with the pre-treatment target cells VOC profile is larger than the ratio between the concentration values from the VOC emission data of pre-treatment target cells cultures, of VOCs associated with the MCD VOC profile and concentration values from the VOC emission data of pre-treatment target cells cultures, of VOCs associated with the pre-treatment target cells VOC profile.

When more than one selected treatment is employed, the optimal treatment is determined from the selected treatments by determining the treatment in which the concentration levels of VOCs in the MCD target cells VOC profile exhibit the largest increase and in which the concentration levels of VOCs in the pre-treatment target cells VOC profile exhibit the largest reduction. With reference to FIG. 1, processor 106 determines the effect of the selected treatment. After procedure 828, the method proceeds to procedure 832.

In procedure 830, the effect of each selected treatment on the healthy cells is determined. To determine the effect of a selected treatment, the concentration values of the VOCs in the pre-treatment healthy cells VOC profile before and after the selected treatment and in the MCD healthy cells VOC profile before and after the selected treatment are determined. To that end, the concentration values of the VOCs in the pre-treatment healthy cells VOC profile are determined from the pre-treatment healthy cells cultures VOC emission data acquired from healthy cells culture 'B'. Also, the concentration values of the VOCs in the MCD healthy cells VOC profile are determined from the pre-treatment healthy cells cultures VOC emission data acquired from healthy cells culture 'A'. Furthermore, the concentration values of the VOCs in the pre-treatment healthy cells VOC profile are determined from the post-treatment healthy cells cultures VOC emission data acquired from healthy cells culture 'B' and the concentration values of the VOCs in the MCD healthy cells VOC profile are determined from the post-treatment healthy cells cultures VOC emission data acquired from healthy cells culture 'A'. A selected treatment is determined as effective when:

(a) concentration values from the post-treatment healthy cells cultures VOC emission data, of the VOCs in the pre-treatment healthy cells VOC profile, remain unchanged relative to concentration values from the pre-treatment healthy cells cultures VOC emission data, of VOCs associated with the pre-treatment healthy cells VOC profile; and (b) concentration values from the post-treatment healthy cells cultures VOC emission data, of VOCs associated with the MCD healthy cells VOC profile remain unchanged relative to concentration values from the pre-treatment healthy cells cultures VOC emission data, of VOCs in the MCD healthy cells VOC profile.

According to another example,
concentration values from the post-treatment healthy cells cultures VOC emission data, of VOCs associated with the MCD healthy cells VOC profile and concentration values from the post-treatment healthy cells cultures VOC emission data, of the VOCs in the pre-treatment healthy cells VOC profile is equal to the concentration values from the pre-treatment healthy cells cultures VOC emission data, of VOCs in the MCD healthy cells VOC profile and concentration values from the pre-treatment healthy cells cultures VOC emission data, of VOCs associated with the pre-treatment healthy cells VOC profile.

When more than one selected treatment is employed, the optimal treatment is determined from the selected treatments by determining the treatment that exhibits the least change within the concentration levels of VOCs in the MCD healthy cells VOC profile and in the pre-treatment healthy cells VOC profile. With reference to FIG. 1, processor 106 determines the effect of the selected treatment. After procedure 830, the method proceeds to procedure 832.

In procedure 832, a compounded treatment response is determined for each selected treatment from the four treatment effect parameters (i.e., the effect of the treatment on target cells, the effect of the treatment of the healthy cells, the treatment resistant potential and the mutation rate potential). When the selected treatment is determined to be effective in all of these four parameters, the compounded treatment response is rendered as positive and the treatment may be rendered as optimal. When more than one selected treatment is employed, the treatment which has the highest positive response in all four treatment effect parameters may be determined as the optimal treatment from the selected treatments. With reference to FIG. 1, process 106 determines a compounded treatment response for each selected treatment from the four treatment effect parameters.

Diffusion Models

As described above, VOC concentration levels in the breath and body fluids are predicted by using a diffusion model of the VOCs from the target and healthy cells to the body fluids and the breath. Specifically, Dynamic Differential VOC profiles are determined from predicted target cells VOC profiles, predicted healthy cells VOC profiles and in some cases additional predicted profiles. The various predicted profiles are determined by predicting the VOCs concentration levels of VOCs of interest in breath and body fluids VOC emission data based upon the target cells, healthy cells and the control cells metabolic rate and the production rate in-vitro. During the determination of Dynamic Differential VOC profiles, breath and body fluids samples VOC emission data is also used to minimize possible error margin between various predicted profiles and actual results. One such model, which relates the alveolar VOC concentration (i.e., in the breath) to their underlying blood concentration is the Farhi equation, which takes the following form:

$$C_A(0) = \frac{C_{\bar{V}}(0)}{\lambda_{b:air} + \frac{\dot{V}_A}{\dot{Q}_C}} \quad (1)$$

$C_A(0)$ relates to the VOC concentration in alveolar in parts per billion, $C_{\bar{V}}(0)$ relates to the mixed concentration in the venous blood in parts per billion, $\lambda_{b:air}$ relates to the Blood-Gas partition coefficient, $\dot{V}_A$ relates to the ventilation in liters per minute and $\dot{Q}_C$ relates to the cardiac output in liters per minute.

The standard Farhi equation explained above refers only to possible VOC concentration in the alveolar (i.e., the lower part of the lungs) compartment. This model may lead to erroneous results.

Figure 16:
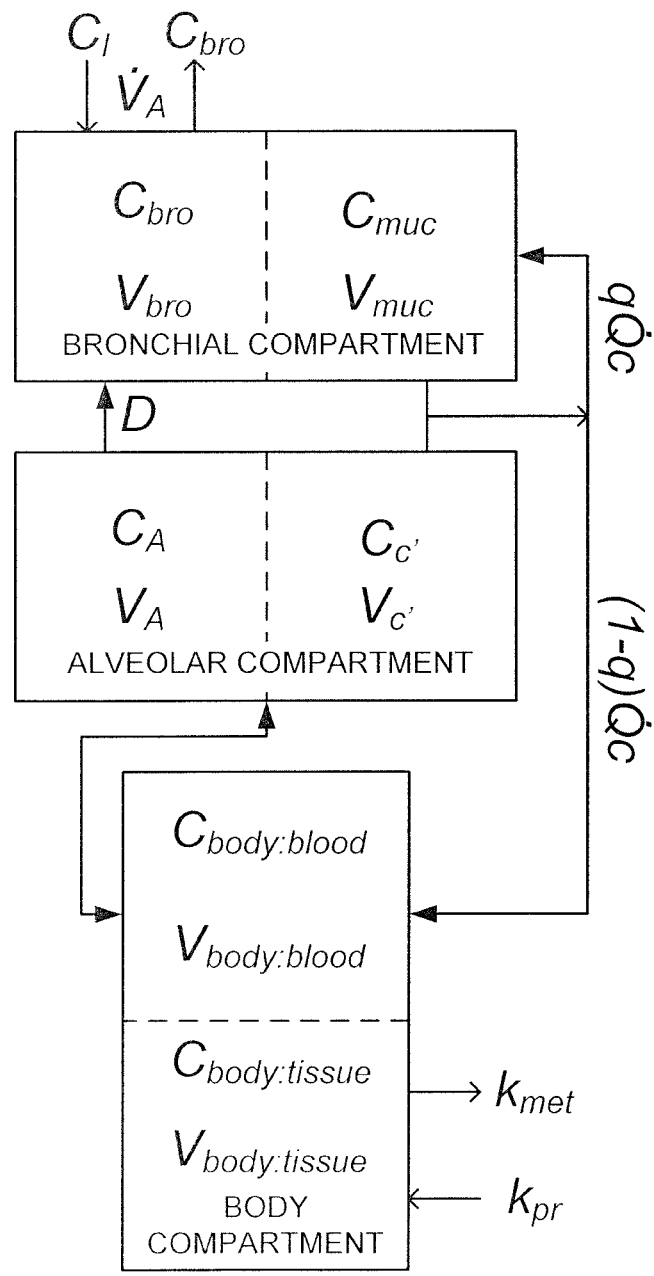
FIG. 16 is a schematic illustration of an extended Farhi's model, operative in accordance with a further embodiment of the disclosed technique.

The model described herein below, extends the standard Farhi equation (a two compartment model to a three compartment model (i.e., an extended Farhi's model). Reference is now made to FIG. 16 which is a schematic illustration of the extended Farhi's model, generally referenced 840, operative in accordance with a further embodiment of the disclosed technique. As depicted in FIG. 16, extended Farhi's model 840 includes three compartments, the bronchial compartment 842, the alveolar compartment 844 and the body compartment 846. The bronchial compartment 842, the alveolar compartment 844 relate to the lung. Body compartment 844 (i.e., metabolism and production) combines the body's blood and tissue compartment (i.e., any form of target cells, healthy cells, or control cells from within the body) into one compartment with an effective Volume $\tilde{V}$. Since the body's blood compartment and the tissue compartment are assumed to be in equilibrium, and therefore can be combined into one single body compartment 844 (i.e., the body's blood and target cells, healthy cells, or control cells compartment) with an effective volume given by:

$$\tilde{V}_B = V_{body\ blood} + \lambda_{B:b} V_{cell\ tissue} \quad (2)$$

The usage of the three compartment model may be employed to produce more accurate Dynamic Differential VOC profiles. The three compartments model incorporates the influence of the upper airways (bronchial) and exhaled VOC concentrations in order to resolve known issues with the standard Farhi equation. The three compartments model detailed herein below also takes into consideration the influence of inhaled VOCs (environmental polluters) on exhaled breath concentrations for VOCs with higher Henry constants. The bronchial compartment 842 is considered a separate compartment which is separated into a gas phase and a mucus membrane, which is assumed to inherit the physical properties of water and acts as a reservoir. The part of the VOCs dissolve in this layer is transferred to the bronchial circulation, whereby the major fraction of the associated venous drainage is postulated to join the pulmonary veins via the post capillary anastomoses. The amount of the VOCs transported at a time 't', via exhalation and inhalation to bronchial compartment 842 therefore equals:

$$\dot{V}_A(C_I - C_{bro}) \quad (3)$$

where $\dot{V}_A$ denotes the ventilation $C_I$ denotes the concentration in the inhaled air (normally assumed to be zero), and $C_{bro}$ the bronchial air concentration. The contribution of the blood flow through the preliminary veins via the post capillary osmosis is given by:

$$q\dot{Q}_c\left(C_a - \frac{\lambda_{muc:air}}{\lambda_{muc:b}} C_{bro}\right) \quad (4)$$

where $\dot{Q}$ denotes the fractional blood flow through the bronchioles, $\dot{Q}_c$ denotes the cardiac output, denotes $C_a$ the arterial blood concentration, $\lambda_{muc:b}$ denotes the mucus:blood partition coefficient and $\lambda_{muc:air}$ denotes the temperature depended mucus:air partition coefficient. Then the arterial blood concentration $C_a$ is given by:

$$C_a = (1-q)\lambda_{b:air} C_A + q\frac{\lambda_{muc:air}}{\lambda_{muc:b}} C_{bro} \quad (5)$$

with $\lambda_{b:air}$ denoting the blood:air partition coefficient and $C_A$ the alveolar concentration.

The decrease of solubility in the mucosa with increasing temperature can be described in the ambient temperature range by a Van't Hoff type equation:

$$\log_{10}\lambda_{muc:air}(T) = -A + \frac{B}{T + 273.15} \quad (6)$$

where A and B (in Kelvin) are proportional to the entropy and enthalpy of volatilization, respectively. $\lambda_{b:air}$ always refers to 37° C. Similarly, the partition coefficient between mucosa and blood $\lambda_{muc:b}$ is treated as a constant defined by:

$$\lambda_{muc:b} := \lambda_{muc:air}(37°\ C.)/\lambda_{b:air} \quad (7)$$

The exchange between the bronchial compartment 842 and the alveolar compartment 844 is modeled as a diffusion process:

$$D(C_A - C_{bro}) \quad (8)$$

with a diffusion constant D which takes values between zero and infinity.

The total mass balance for bronchial compartment 842 is given by:

$$\tilde{V}_{bro}\frac{dC_{bro}}{dt} = \dot{V}_A(C_I - C_{bro}) + D(C_A - C_{bro}) + q\dot{Q}_c\left(C_a - \frac{\lambda_{muc:air}}{\lambda_{muc:b}} C_{bro}\right) \quad (9)$$

The mass balance for alveolar compartment 844 is given by:

$$\tilde{V}_A \frac{dC_A}{dt} = D(C_{bro} - C_A) + (1-q)\dot{Q}_c(C_{\bar{v}} - \lambda_{b:air} C_A) \quad (10)$$

and the mass balance for body compartment 846 is given by:

$$\tilde{V}_B \frac{dC_B}{dt} = (1-q)\dot{Q}_c(C_a - C_{\bar{v}}) - \lambda_{b:B} k_{met} C_B + k_{pr} \quad (11)$$

where $k_{met}$ denotes the total metabolic rate of the body and $k_{pr}$ denotes the production rate. $\tilde{V}_{bro}$, $\tilde{V}_A$, and $\tilde{V}_B$ denote the effective volume of the bronchioles, alveoli, and the body, respectively. Also, $C_B$ is the concentration in the body which is connected to the mixed venous concentration $C_{\bar{v}}$ by Henry's law $C_{\bar{v}} = \lambda_{b:B} C_B$ where $\lambda_{b:B}$ denotes the blood:body tissue partition coefficient.

Summing up the three linear differential equations (9), (10) and (11) yields the total change of mass of a VOC ($m_{tot}$):

$$\tilde{V}_{bro}\frac{dC_{bro}}{dt} + \tilde{V}_A\frac{dC_A}{dt} + \tilde{V}_B\frac{dC_B}{dt} = \quad (12)$$

$$\frac{dm_{tot}}{dt} = \dot{V}_A C_I - \dot{V}_A C_{bro} + k_{pr} - k_{met} C_{\bar{v}}$$

The total change of mass of a VOC is given by what is inhaled minus what is exhaled plus what is produced by the body minus what is eliminated by metabolism (metabolism includes all loses, e.g., by liver, urine, skin, etc.), so that the total mass balance is fulfilled.

VOC Filter

In the description above, all of the VOC emission data acquired either from the breath and/or body fluids and/or from cells cultures, and the comparisons therebetween, may be employed to detect common VOCs therein. These common VOCs may be employed to define a VOCs filter. Such a VOCs filter may be employed to filter the common VOCs when acquiring new VOC emission data of breath and/or body fluids and/or cells cultures. Such a VOCs filter may also be employed to filter the common VOCs in VOC profiles. The filters are constructed by comparing healthy VOC emission data of the same type of healthy cells from a plurality of patients and identifying the VOCs related to the normal activity of these healthy cells. A diffusion equation (e.g., the Farhi equation discussed above) is employed to produce a range of VOC concentration levels related to the normal activities. These VOC concentration levels related to the normal activities are employed to filter out these VOCs from VOC emission data to identify abnormal concentrations.

VOC Profile Comparison

In the embodiments described above, VOC profiles are compared one with the other. According to one alternative, the VOC profiles are compared by comparing polygons defined by the VOC profiles. A VOC profile may be considered as a two dimensional Euclidean space where the horizontal axis is defined by the VOCs and the vertical axis is defined by the concentration levels. In a VOC profile space, a polygon is defined by a reference point and the peak values of selected VOCs. The reference point may be the zero coordinates of the two dimensional space. When comparing two VOC profiles, the same polygon or polygons are defined in the two VOC profiles (i.e., employing the same reference point and the same selected VOCs). These two polygons are then compared one with the other, for example, by using the $L^p$ distance between the turning functions of the two polygons.

Increasing VOC Concentration

When determining the VOC emission data in breath samples, it may be desirable to increase the VOCs in the lungs prior to sampling the breath. To that end, prior to sampling the patients are requested to exhale their breath to their maximum ability. Thereafter, the patients inhale and hold their breath for a predetermined time duration (e.g., 5, 10, 20, 30 seconds, 1 minute), and exhales into the breath samples collector. The time duration each patient holds their breath is measured in order to correlate between breath samples acquired with different breath holding durations.

Figure 17B:
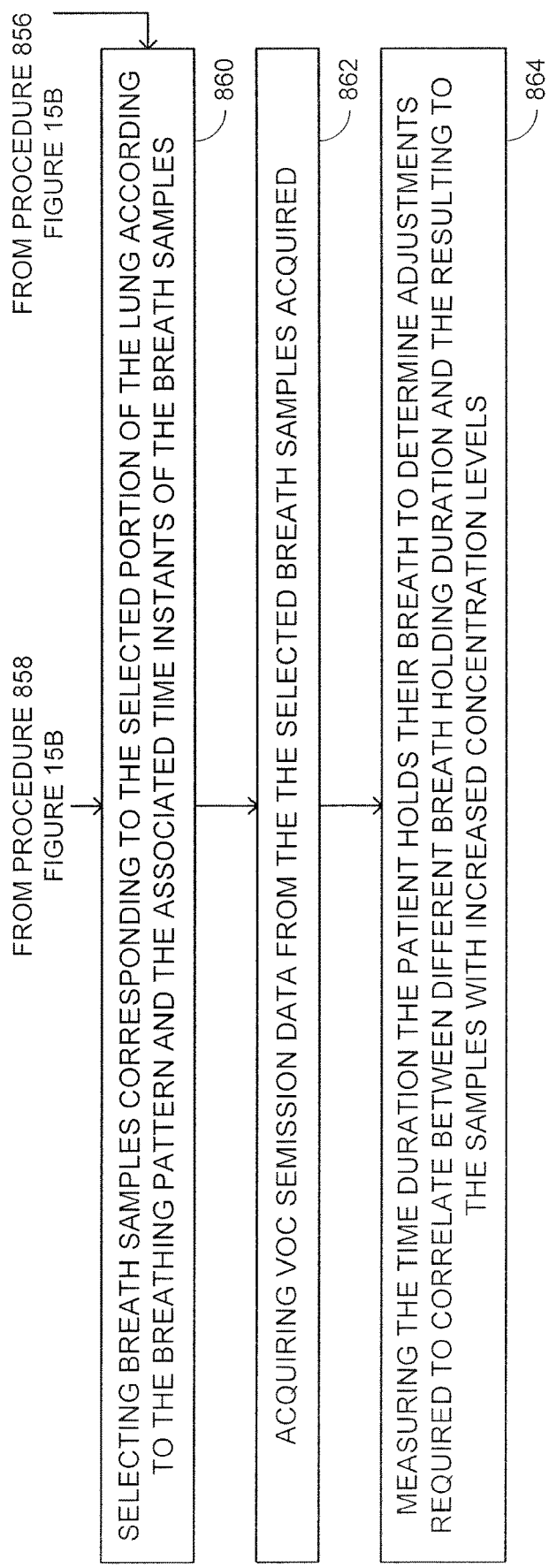

Furthermore, the method detailed above for increasing the VOCs concentration levels in the breath prior to sampling a breath may be combined with a known method in the art for sampling a quantified amount of exhaled air from selected portions of the lungs (e.g., bronchial, alveolar, the whole lungs), thereby increasing the VOCs concentration levels of VOCs typically found in the breath below the detection limit of the analysis devices to a level where they can be detected, identified and quantified. Reference is now made to FIGS. 17A and 17B, which are a schematic illustration of a method for increasing the VOCs concentration prior to sampling and sampling a quantified amount of air from a selected portion of the lungs, operative in accordance with another embodiment of the disclosed technique.

In procedure 850, the portion of the lungs from which air is to be sampled and the volume of air to be sampled are selected. After procedure 850, the method proceeds to procedure 852.

In procedure 852, the inhale flow rate, the exhale flow rate and the Carbon Dioxide ($CO_2$) concentration levels are measured when the patient is breathing normally over a duration of time (e.g., several breaths). The inhale and exhale flow rates and the $CO_2$ concentration may be measured with a spirometer, which includes a flow meter and $CO_2$ sensor. After procedure 852, the method proceeds to procedure 854.

In procedure 854, the inhale flow rate, the exhale flow rate and the $CO_2$ concentration levels are measured when the patient exhales and inhales to the maximum capability thereof. After procedure 854, the method proceeds to procedure 856.

In procedure 856, a breathing pattern, differentiating between the bronchial part in the exhaled breath and the alveolar part of the exhaled breath is determined. After procedure 856, the method proceeds to procedures 858 and 860.

In procedure 858, breath samples are acquired when the patient exhales to the maximum capability thereof, after the patient exhaled to the maximum capability thereof, inhaled to the maximum capability thereof and held their breath at least for a predetermined time period. Each breath sample is associated with a respective time instant in the determined breathing pattern. After procedure 858, the method proceeds to procedure 860.

In procedure 860, breath samples corresponding to the selected portion of the lung are selected according to the breathing pattern and the associated time instants of the breath samples. After procedure 858, the method proceeds to procedure 862.

In procedure 862, VOC emission data is acquired from the selected breath samples acquired. With reference to FIG. 1, analysis device 102 acquires VOC emission data from the selected breath samples. After procedure 862, the method proceeds to procedure 864.

In procedure 864, the time duration the patient holds their breath is measured to determine adjustments that may be required to correlate between different breath holding durations and the resulting increased concentration levels within the acquired samples (i.e., normalization).

In some cases, the selected volume of air cannot be acquired in a single iteration. As such procedure 858 may be repeated until the selected volume of air is acquired, while the patient holds their breath for the same time duration, in each iteration.

It will be appreciated by persons skilled in the art that the disclosed technique is not limited to what has been particularly shown and described hereinabove. Rather the scope of the disclosed technique is defined only by the claims, which follow.

What is claimed is:

1. A method for determining an efficacy of a treatment of a metabolic, anabolic, catabolic, genetic and/or medical condition administered to a patient, comprising procedures of:
    acquiring pre-treatment patient volatile organic compound (VOC) emission data of the VOCs emitted from at least one of breath samples and body fluid samples prior to at least one selected phase of said treatment;
    acquiring VOC emission data of pre-treatment target cells cultures;
    producing a predicted massive cell death (MCD) target cells VOC profile by:
        (a) inducing massive cell death on non-treated target cells cultures thereby producing post-MCD target cells cultures;
        (b) acquiring VOC emission data of said post-MCD target cells cultures; and (c) predicting concentration levels of the VOCs in the breath and/or body fluids employing a diffusion model;

applying the selected treatment to said patient;

acquiring post-treatment patient VOC emission data of the VOCs emitted from at least one of breath samples and body fluid samples that were acquired during and/or after at least one selected phase of said treatment;

applying said selected treatment at least to healthy cells cultures;

producing a predicted treatment-induced MCD healthy cells VOC profile by:

(a) acquiring VOC emission data of the VOCs associated with treated healthy cells cultures; and (b) predicting the concentration levels of said VOCs in the breath and/or body fluids employing a diffusion model, and determining the efficacy of the selected treatment, said treatment is determined as effective when concentration values of the VOCs in said predicted MCD target cells VOC profile during and/or after said selected phase of said treatment from said post-treatment patient VOC emission data associated with at least one of breath samples and body fluid samples, are greater than concentration values of the VOCs in said predicted MCD target cells VOC profile before said selected phase of said treatment from said pre-treatment patient VOC emission data associated with at least one of breath samples and body fluid samples, and when the concentration values from said post-treatment patient VOC emission data associated with at least one of breath samples and body fluid samples of VOCs in said predicted treatment-induced MCD healthy cells VOC profile remain unchanged to concentration values from said pre-treatment patient VOC emission data associated with at least one of breath samples and body fluid samples of VOCs in said predicted treatment-induced MCD healthy cells VOC profile, wherein said predicted MCD target cells VOC profile represents a range of VOC emission data of VOCs emitted from said post-MCD target cells cultures.

2. The method according to claim 1, further comprises:

producing a pre-treatment target cells VOC profile from said VOC emission of said pre-treatment target cells cultures;

applying said at least one selected treatment at least to target cells cultures;

producing a predicted treatment-induced MCD target cells VOC profile by:

(a) acquiring VOC emission data of the VOCs associated with said post-MCD target cells cultures; and (b) predicting the concentration levels of the VOCs in the breath and/or body fluids employing a diffusion model, wherein said treatment is further determined as effective when concentration values of the VOCs associated with said predicted treatment-induced MCD target cells VOC profile, from said post-treatment patient VOC emission data associated with at least one of breath samples and body fluid samples are greater than concentration values of the VOCs associated with said predicted treatment-induced MCD target cells VOC profile, from said pre-treatment patient VOC emission data associated with at least one of breath samples and body fluid samples.

3. The method according to claim 1, further comprising a procedure of determining individual personal treatment efficacy, comprising sub procedures of:

producing a pre-treatment target cells VOC profile from said VOC emission of said pre-treatment target cells cultures;

producing an MCD target cells VOC profile by:

(a) inducing massive cell death on non-treated target cells cultures thereby producing post-MCD target cells cultures; and (b) acquiring VOC emission data of said post-MCD target cells cultures;

applying said at least one selected treatment at least to target cells cultures;

for each selected treatment, acquiring VOC emission data of post-treatment target cells cultures, wherein said treatment is further determined as effective when concentration values from said VOC emission data of pre-treatment target cells cultures, of VOCs associated with said pre-treatment target cells VOC profile, are greater than concentration values from said VOC emission data of post-treatment target cells cultures, of VOCs associated with said pre-treatment target cells VOC profile.

4. The method according to claim 3, wherein said procedure of determining individual personal treatment efficacy includes the sub-procedures of:

determining at least one of dynamic treatment resistance potential differential VOC profiles and at least one mutation rate differential VOC profile of at least one mutation and/or pathogen, from stored Dynamic Differential VOC profiles and the post-treatment patient VOC emission data; and determining concentration values of the VOCs in said dynamic patient treatment resistance potential differential VOC profile and in said mutation rate differential VOC profile from said pre-treatment target cells cultures VOC emission data; and determining concentration values of the VOCs in said dynamic patient treatment resistance potential differential VOC profile and in said mutation rate differential VOC profile from said post-treatment patient VOC emission data.

5. The method according to claim 4, wherein said treatment is determined as effective when concentration values of the VOCs in said dynamic patient treatment resistance potential differential VOC profile and in said mutation rate differential VOC profile during and/or after said at least one phase of said treatment, remain un-changed relative to the concentration values of said VOCs before said at least one phase of said treatment.

6. The method according to claim 1, wherein said procedure of determining individual personal treatment efficacy includes sub-procedures of:

determining concentration values of the VOCs in said pre-treatment healthy cells VOC profile relating to said healthy cells, before said at least one phase of said treatment from said pre-treatment healthy cells cultures VOC emission data;

determining concentration values of said VOCs in said pre-treatment healthy cells VOC profile relating to said healthy cells, during and/or after said at least one phase of said treatment from said post-treatment patient VOC emission data;

determining concentration values of the VOCs in said predicted treatment-induced MCD healthy cells VOC profile, before said at least one phase of said treatment from said pre-treatment healthy cells cultures VOC emission data;

determining concentration values of the VOCs in said predicted treatment-induced MCD healthy cells VOC profile, during and/or after said at least one phase of said treatment from said post-treatment patient VOC emission data;

determining concentration values of the VOCs in said predicted MCD healthy cells VOC profile, before said at least one phase of said treatment from said pre-treatment healthy cells cultures VOC emission data; and determining concentration values of the VOCs in said predicted MCD healthy cells VOC profile, during and/or after said at least one phase of said treatment from said post-treatment patient VOC emission data.

7. The method according to claim 1, wherein prior to said procedure of determining a pre-treatment target cells VOC profile and pre-treatment healthy cells VOC profile, said method further includes the procedures of:

acquiring at least one of breath samples and body fluid samples from said patient, prior to administering said treatment;

acquiring VOC emission data of the VOCs emitted in said at least one of breath samples and body fluid samples;

acquiring from said patient target cells samples and healthy cells samples of the same cell type as said target cells, prior to administering said treatment;

producing two sets of target cell cultures from the target cells samples and two sets of healthy cells cultures from the healthy cells samples; and acquiring pre-treatment target cells cultures VOC emission data relating to said both target cells cultures sets and pre-treatment healthy cells cultures VOC emission data relating to said both healthy cells cultures sets, prior to administering said treatment.

8. The method according to claim 7, wherein after said procedure of determining a pre-treatment VOC profile and prior to said procedure of producing a predicted treatment-induced target MCD VOC profile, said method further includes the procedures of:

applying the selected treatment to the cells in a first one of said sets of target cells cultures and to a first one of said sets of healthy cells cultures;

acquiring post-treatment VOC emission data relating to said target cells cultures and to said healthy cells cultures after the application of said treatment;

inducing massive cell death to the cells in a second one of said sets target cells cultures and to a second one of said sets of healthy cells cultures; and acquiring post-MCD VOC emission data relating to said second set target cells cultures and to said second set healthy cells cultures, after the induction of MCD.

9. The method according to claim 1, wherein said at least one phase of said treatment is determined as effective when no new mutations are identified, wherein new mutation is identified by attempting to identify a stored Dynamic Differential VOC profile which corresponds to said post-treatment patient VOC emission data.

10. The method according to claim 9, wherein prior to said attempt to identify a new mutation, said post-treatment patient VOC emission data is filtered with said pre-treatment target cells VOC profile, with said treatment induced MCD target cells VOC profile, and with said MCD target cells VOC profile thereby alleviating information relating to the VOCs which result from said treatment.

\* \* \* \* \*